United States Patent
Rapraeger et al.

(10) Patent No.: US 10,220,073 B2
(45) Date of Patent: Mar. 5, 2019

(54) PEPTIDES OF SYNDECAN-1 FOR INHIBITING ANGIOGENESIS

(71) Applicant: Wisconsin Alumni Research Foundation, Madison, WI (US)

(72) Inventors: Alan C. Rapraeger, Madison, WI (US); DeannaLee M. Beauvais, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 7 days.

(21) Appl. No.: 15/347,934

(22) Filed: Nov. 10, 2016

(65) Prior Publication Data
US 2017/0056470 A1     Mar. 2, 2017

Related U.S. Application Data

(62) Division of application No. 13/734,302, filed on Jan. 4, 2013, now Pat. No. 9,522,944, which is a division of application No. 11/760,594, filed on Jun. 8, 2007, now abandoned.

(60) Provisional application No. 60/812,187, filed on Jun. 9, 2006.

(51) Int. Cl.
| | | |
|---|---|---|
| *A61K 38/17* | (2006.01) | |
| *C07K 14/705* | (2006.01) | |
| *C07K 7/06* | (2006.01) | |
| *C07K 7/08* | (2006.01) | |
| *C07K 14/47* | (2006.01) | |
| *A61K 45/06* | (2006.01) | |
| *A61K 38/00* | (2006.01) | |

(52) U.S. Cl.
CPC .......... *A61K 38/1709* (2013.01); *A61K 45/06* (2013.01); *C07K 7/06* (2013.01); *C07K 7/08* (2013.01); *C07K 14/4725* (2013.01); *C07K 14/705* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,504,191 A | 4/1996 | Pettit et al. | 530/330 |
| 5,851,993 A | 12/1998 | Jalkanen et al. | 514/12 |
| 6,982,265 B1 | 1/2006 | Hunt et al. | 514/243 |
| 2002/0032180 A1 | 3/2002 | Tanabe et al. | 514/179 |
| 2004/0224914 A1* | 11/2004 | Jackson | C12N 15/113 514/44 A |
| 2006/0134122 A1 | 6/2006 | Rapraeger et al. | 424/155.1 |
| 2007/0054332 A1 | 3/2007 | Rapraeger et al. | 435/7.23 |

OTHER PUBLICATIONS

English Language and Usage (retrieved from http://english.stackexchange.com/questions/7871/between-a-and-b-or-from-a-to-b on Dec. 22, 2014, 2 pages) (Year: 2014).*
Panchenko et al. ('Prediction of functional sites by analysis of sequence and structure conservation' Protein Science 2004 v13 pp. 884-892) (Year: 2004).*
Staton et al. ('A critical analysis of current in vitro and in vivo angiogenesis assays' International Journal of Experimental Pathology v90 2009 pp. 195-221) (Year: 2009).*
Di Stefano et al. ('Angiogenesis as Risk Factor for Plaque Vulnerability' Current Pharmaceutical Design v15 2009 pp. 1095-1106) (Year: 2009).*
Beauvais et al ('Syndecan-1 couples the insulin-like growth factor-1 receptor to inside-out integrin activation' Journal of Cell Science v123 2010 pp. 3796-3807).
English Language and Usage (retrieved from http://english.stackexchange.com/questions/7871/between-a-and-b-or-from-a-to-b on Dec. 22, 2014, 2 pages).
Beauvais et al (Matrix Biology v25 Nov. 26 p. s42 retrieved from http://www.sciencedirect.com/science?_ob=ArticleURL&_udi=B6VPM-4KKWTGS-42&_user=2502287&_rdoc=1&_fmt=&_orig=search&_sort=d&view=c&_acct=C0000055109&_version=1&_urlVersion=0&_userid=2502287&md5=2cc5925304cf90acd49802193d52b5c0 on Jan. 14, 2009, 2 pages).
Patent Board Decision in U.S. Appl. No. 11/760,594 dated Aug. 29, 2012, total of 16 pages.
Examiner's Answer to appeal brief in U.S. Appl. No. 11/760,594 dated Jun. 9, 2010, total of 16 pages.
Adams et al., "A Role for Syndecan-1 in Coupling Fascin Spike Formation by Thrombospondin-1," *J. Cell Biol.*, 152:1169-1182, 2000.
Alexander et al., „Syndecan-1 is required for Wnt-1-induced mammary tumorigenesis in mice, *Nat. Genet.*, 25:329-332, 2000.
Anttonen et al., "Syndecan-1 expression has prognostic significance in head and neck carcinoma," *Br. J. Cancer*, 79:558-564, 1999.
Bader et al., "Extensive vasculogenesis, angiogenesis, and organogenesis precede lethality in mice lacking all alpha v integrins," *Cell*, 95:507-519, 1998.
Barbareschi et al., "High syndecan-1 expression in breast carcinoma is related to an aggressive phenotype and to poorer prognosis," *Cancer*, 98:474-483, 2003.
Beauvais and Rapraeger, "Syndecan-1-mediated cell spreading requires signaling by alphavbeta3 integrins in human breast carcinoma cells," *Exp. Cell Res.*, 286:219-232, 2003.
Beauvais and Rapraeger, "Syndecans in tumor cell adhesion and signaling," *Reproductive Biology and Endocrinology*, 2:1-12, 2004.

(Continued)

*Primary Examiner* — Karlheinz R. Skowronek
*Assistant Examiner* — Ronald T Niebauer
(74) *Attorney, Agent, or Firm* — Boyle Fredrickson S.C.

(57) ABSTRACT

The present invention provides a peptide derived from the extracellular domain of syndecan-1 that inhibits angiogenesis.

15 Claims, 20 Drawing Sheets
Specification includes a Sequence Listing.

(56) References Cited

OTHER PUBLICATIONS

Beauvais and Rapraeger, "The Syndecan-1 Ectodomain is Required for $\alpha_v\beta_3$ Integrin-Dependent Signaling in Human Mammary Carcinoma Cell Spreading," *Molecular Biology of the Cell*, 14:272A, 2003.
Beauvais et al., "The syndecan-1 ectodomain regulates alphavbeta3 integrin activity in human mammary carcinoma cells," *J. Cell Biol.*, 167:171-181, 2004.
Becker-Hapak et al., "Tat-mediated protein transduction into mammalian cells," *Methods*, 24:247-256, 2001.
Bernfield et al., "Functions of cell surface heparan sulfate proteoglycans," *Annu. Rev. Biochem.*, 68:729-777, 1999.
Boettiger et al., "Activation of alpha(v)beta3-vitronectin binding is a multistage process in which increases in bond strength are dependent on Y747 and Y759 in the cytoplasmic domain of beta3," *Molec. Biol. Cell*, 12:1227-1237, 2001.
Boettiger et al., "Distinct ligand-binding modes for integrin alpha(v)beta(3)-mediated adhesion to fibronectin versus vitronectin," *J. Biol. Chem.*, 276:31684-31690, 2001.
Burbach et al., "Syndecan-1 accumulates in lysosomes of poorly differentiated breast carcinoma cells," *Matrix Biol.*, 22:163-177, 2003.
Conejo et al., "Syndecan-1 expression is up-regulated in pancreatic but not in other gastrointestinal cancers," *Int. J. Cancer*, 88:12-20, 2000.
Crescimanno et al., "Expression pattern alterations of syndecans and glypican-1 in normal and pathological trophoblast," *J. Pathol.*, 189:600-608, 1999.
Denicourt and Dowdy, "Protein transduction technology offers novel therapeutic approach for brain ischemia," *Trends Pharmacol. Sci.*, 24:216-218, 2003.
Dhodapkar et al., "Syndecan-1 Is a Multifunctional Regulator of Myeloma Pathobiology: Control of Tumor Cell Survival, Growth, and Bone Cell Differentiation," *Blood*, 91:2679-2688, 1999.
Felding-Habermann et al., "Integrin activation controls metastasis in human breast cancer," *Proceedings of the National Academy of Sciences of the United States of America*, 98:1853-1858, 2001.
Fujiya et al., "Reduced expression of syndecan-1 affects metastatic potential and clinical outcome in patients with colorectal cancer," *Jpn. J. Cancer Res.*, 92:1074-1081, 2001.
Gallo et al., "Syndecans-1 and-4 are induced during wound repair of neonatal but not fetal skin," *J. Invest. Dermatol.*, 107(5):676-683, 1996.
Gotte et al., "Role of syndecan-1 in leukocyte-endothelial interactions in the ocular vasculature," *Invest. Ophthal. Visual Sci.*, 43(4):1135-1141, 2002.
Hirabayashi et al., "Altered Proliferative and Metastatic Potential Associated with Increased Expression of Syndecan-1," *Tumor Biol.*, 19:454-463, 1998.
Hood et al., "Differential αv integrin—mediated Ras-ERK signaling during two pathways of angiogenesis," *Journal of Cell Biology*, 162:933-943, 2003.
Iba et al., "The cysteine-rich domain of human ADAM 12 supports cell adhesion through syndecans and triggers signaling events that lead to beta1 integrin-dependent cell spreading," *J. Cell Biol.*, 149:1143-1156, 2000.
Inki et al., "Association between syndecan-1 expression and clinical outcome in squamous cell carcinoma of the head and neck," *Br. J. Cancer*, 70:319-323, 1994.
Inki et al., "Immunohistochemical localization of syndecan-1 in normal and pathological human uterine cervix," *J. Pathol.*, 172:349-355, 1994.
Kainulainen et al., "Suppression of syndecan-1 expression in endothelial cells by tumor necrosis factor-alpha," *J. Biol. Chem.*, 271:18759-18766, 1996.
Kato et al., "Loss of cell surface syndecan-1 causes epithelia to transform into anchorage-independent mesenchyme-like cells," *Mol. Biol. Cell*, 6:559-576, 1995.
Kogan et al., A single amino acid residue can determine the ligand specificity of E-selectin, *J. Biol. Chem.*, 270:14047-14055, 1995.
Kumar-Singh et al., "Syndecan-1 expression in malignant mesothelioma: correlation with cell differentiation, WT1 expression, and clinical outcome," *J. Pathol.*, 186:300-305, 1998.
Kuntz, "Structure-based strategies for drug design and discovery," *Science*, 257:1078-1082, 1992.
Levy et al., "Oncogenic activation of p21ras or pp60c-src in human colonic Caco-2 cells induces post-translation alterations of syndecan-1," *Bull. Cancer*, 84:235-237, 1997.
Levy et al., "Syndecan-1 alterations during the tumorigenic progression of human colonic Caco-2 cells induced by human Ha-ras or polyoma middle T oncogenes," *Br. J. Cancer*, 74:423-431, 1996.
Liddington and Ginsberg, "Integrin activation takes shape," *J. Cell Biol.*, 158:833-839, 2002.
Liu et al., "Heparan sulfate proteoglycans as adhesive and anti-invasive molecules. Syndecans and glypican have distinct functions," *J. Biol. Chem.*, 273(35):22825-22832, 1998.
Mali et al., "Suppression of tumor cell growth by syndecan-1 ectodomain,"*J. Biol. Chem.*, 269:27795-27798, 1994.
Matsumoto et al., "Reduced expression of syndecan-1 in human hepatocellular carcinoma with high metastatic potential," *Int. J. Cancer*, 74:482-491, 1997.
McFall and Rapraeger, "Characterization of the high affinity cell-binding domain in the cell surface proteoglycan syndecan-4," *J. Biol. Chem.*, 273:28270-28276, 1998.
McFall and Rapraeger, "Identification of an adhesion site within the syndecan-4 extracellular protein domain," *J. Biol. Chem.*, 272:12901-12904, 1997.
McQuade and Rapraeger, "Syndecan-1 transmembrane and extracellular domains have unique and distinct roles in cell spreading," *J. Biol. Chem.*, 278(47):46607-46615, 2003.
McQuade et al., "Syndecan-1 regulates {alpha} v{beta}5 integrin activity in B82L fibroblasts," *J. Cell Sci.*, 119: 2445-56, 2006.
Miller and Dill, "Ligand binding to proteins: the binding landscape model," *Protein Sci.*, 6:2166-2179, 1997.
Mundhenke et al., "Heparan sulfate proteoglycans as regulators of fibroblast growth factor-2 receptor binding in breast carcinomas," *Am. J. Pathol.*, 160:185-194, 2002.
Nackaerts et al., "Heparan sulfate proteoglycan expression in human lung-cancer cells," *Int. J. Cancer*, 74:335-345, 1997.
Nakanishi et al., "Reduction of syndecan-1 mRNA in cervical-carcinoma cells is involved with the 3' untranslated region," *Intl. J. Cancer*, 80:527-532, 1999.
Numa et al., "Syndecan-1 expression in cancer of the uterine cervix: association with lymph node metastasis," *Int. J. Oncol.*, 20:39-43, 2002.
Office Action issued in U.S. Appl. No. 11/760,594, dated Aug. 6, 2008.
Office Action issued in U.S. Appl. No. 11/760,594, dated Feb. 19, 2008.
Office Action issued in U.S. Appl. No. 11/760,594, dated Jan. 27, 2009.
Office Action issued in U.S. Appl. No. 11/760,594, dated Nov. 13, 2009.
Ohtake et al., "Proline-rich antimicrobial peptide, PR-39 gene transduction altered invasive activity and actin structure in human hepatocellular carcinoma cells," *Br. J. Cancer*, 81:393-403, 1999.
Park et al., "Syndecan-2 mediates adhesion and proliferation of colon carcinoma cells," *J. Biol. Chem.*, 277:29730-29736, 2002.
Pilch et al., "Unique Ability of Integrin $\alpha_v\beta_3$ to Support Tumor Cell Arrest under Dynamic Flow Conditions," *Journal of Biological Chemistry*, 277:21930-21938, 2002.
Pulkkinen et al., "Syndecan-1: a new prognostic marker in laryngeal cancer," *Acta Otolaryngol.*, 117:312-315, 1997.
Rapraeger and Ott, "Molecular interactions of the syndecan core proteins," *Curr. Opin. Cell Biol.*, 10:620-628, 1998.
Rapraeger et al., "Cell surface proteoglycan associates with the cytoskeleton at the basolateral cell surface of mouse mammary epithelial cells," *J. Cell Biol.*, 103:2683-2696, 1986.
Rapraeger, "Syndecan-regulated Receptor Signaling," *Journal of Cell Biology*, 149:995-997, 2000.
*Reproductive Biology and Endocrinology*, 2:3, 2004.

(56) References Cited

OTHER PUBLICATIONS

Reynolds et al., "Enhanced pathological angiogenesis in mice lacking beta3 integrin or beta3 and beta5 integrins," *Nature Med.*, 8:27-34, 2002.
Rintala et al., "Association of syndecan-1 with tumor grade and histology in primary invasive cervical carcinoma," *Gynecol. Onol.*, 75:372-378, 1999.
Sanderson and Borset, "Syndecan-1 in B lymphoid malignancies," *Ann. Hematol.*, 81:125-135, 2002.
Sanderson, "Heparan sulfate proteoglycans in invasion and metastasis," *Semin. Cell Dev. Biol.*, 12:89-98, 2001.
Sasisekharan et al., "Roles of Heparan-Sulphate Glycosaminoglycans in Cancer," *Nature Reviews*, 2:521-528, 2002.
Schwarze et al., "Protein transduction: unrestricted delivery into all cells?," *Trends Cell Biol.*, 10:290-295, 2000.
Soukka et al., "Reduction of syndecan-1 expression is associated with dysplastic oral epithelium," *J. Oral Pathol. Med.*, 29:308-313, 2000.
Stanley et al., "Syndecan-1 expression is induced in the stroma of infiltrating breast carcinoma," *Am. J. Clin. Pathol.*, 112:377-383, 1999.
Tkachenko and Simons, "Clustering induces redistribution of syndecan-4 core protein into raft membrane domains," *J. Biol. Chem.*, 277:19946-19951, 2002.
Tumova et al., "Heparan sulfate chains from glypican and syndecans bind the Hep II domain of fibronectin similarly despite minor structural differences," *J. Biol. Chem.*, 275:9410-9417, 2000.
Wender et al., "The design, synthesis, and evaluation of molecules that enable or enhance cellular uptake: peptoid molecular transporters," *Proc. Natl. Acad. Sci. USA*, 97:13003-13008, 2000.
Wiksten et al., "Epithelial and stromal syndecan-1 expression as predictor of outcome in patients with gastric cancer," *Int. J. Cancer*, 95:1-6, 2001.

* cited by examiner

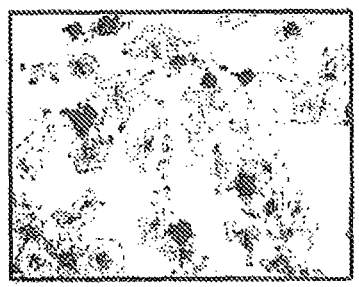
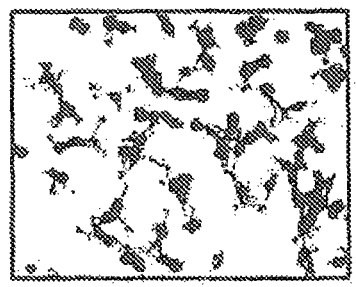
FIG. 5A  FIG. 5B
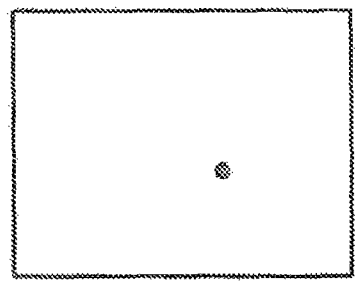
FIG. 5C  FIG. 5D
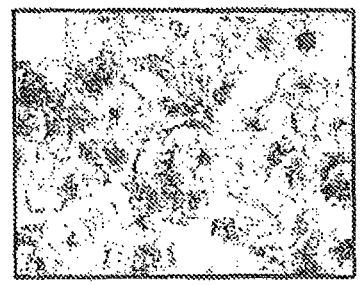
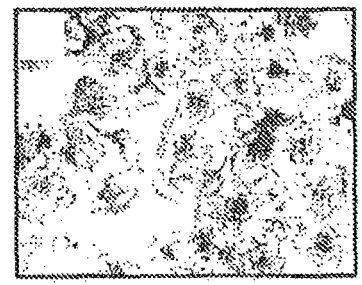
FIG. 5E  FIG. 5F synstatin sequence

```
mur31 #  70        80         90        100       110       120       130       140       150
mmus1:  RLLCAETAEPTSGNTEQAFTSVLPAGEKPEIGEPVLRVLEAEPGETARDKEKSVTKPRETVQLPIQRASTV-RVTHAQAAVTSHPEGG
hams1:  WLLRAETAEPTAEKPTSEQAETTSTLPAEKPGEGPVITAEKPGEPVIRAEPVDKPTTARDKESEVIIAREFTQLLTNMVSEA-RATRQAPVTSHPPD
rat31:  RLLCAETAEPTGRDTEATLTGILPAEKPBEGEPVAHVEAEPDPTARKEKEATTRRETTQLPVTQQASTAARATTAQASVTSHPGD
hums1:  QLLCAETAEPTSPETGLEATAASTSTLPAGEGPREGSBAVTLPEVEPGLTAPEQE--ATPRPRETTQLPTTHQASTV-TATTAQHPATSRPHRD
cons:   .LL.AETAEP.....E...A.TS..L.PAGE.P..E...V..V.....E.....A...KE.E...K.....TQL.....AST.........PT.....
```

FIG. 9

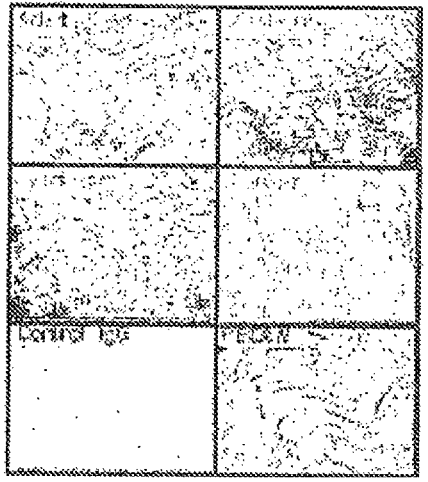
FIG. 11A
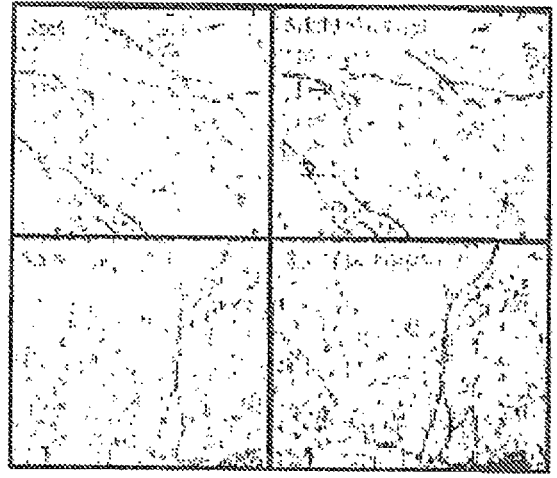
FIG. 11B
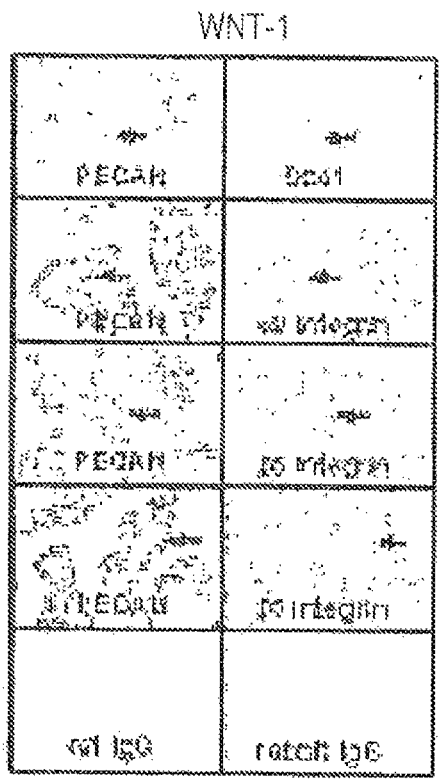
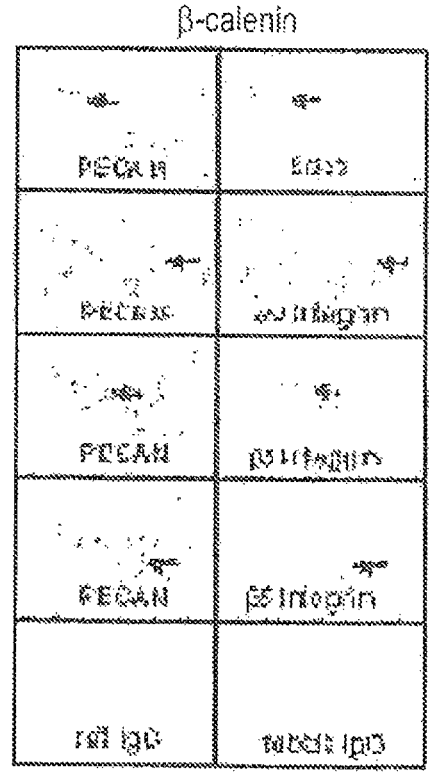
FIG. 11C

FIG. 14

28 days of treatment beginning 10 days after inoculation with CAG tumor cells

PBS             Synstatin

Measurement data are in photons/second/cm²/steradian
(PBS Total) 10859200 / 982252 (Synstatin Total)=11.055

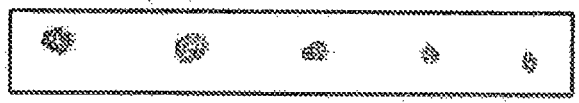
FIG. 16A
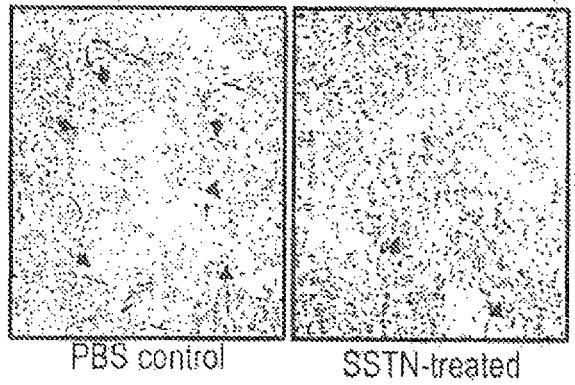
FIG. 16B

SEQUENCE LISTING

<160> NUMBER OF SEQ ID NOS: 28

<210> SEQ ID NO 1
<211> LENGTH: 3217
<212> TYPE: DNA
<213> ORGANISM: Homo sapiens

<400> SEQUENCE: 1

```
ggccgggaga cctggcggag ctgggggtgg ggggccagtt tttgcaacgg ctaaggaagg      60
gcctgtgggt ttattataag gcggagctcg gcgggagagg tgcgggccga atccgagccg     120
agcggagagg aatccggcag tagagagcgg actccagccg gcggaccctg cagccctcgc     180
ctgggacagc ggcgcgctgg gcaggcgccc aagagagcat cgagcagcgg aacccgcgaa     240
gccggcccgc agccgcgacc cgcgcagcct gccgctctcc cgccgccggt ccgggcagca     300
tgaggcgcgc ggcgctctgg ctctggctgt gcgcgctggc gctgagcctg cagccggccc     360
tgccgcaaat tgtggctact aatttgcccc ctgaagatca agatggctct ggggatgact     420
ctgacaactt ctccggctca ggtgcaggtg ctttgcaaga tatcaccttg tcacagcaga     480
ccccctccac ttggaaggac acgcagctcc tgacggctat tcccacgtct ccagaaccca     540
ccggcctgga ggctacagct gcctccacct ccaccctgcc ggctggagag gggcccaagg     600
agggagaggc tgtagtcctg ccagaagtgg agcctggcct caccgcccgg gagcaggagg     660
```

```
ccaccccccg acccagggag accacacagc tcccgaccac tcatcaggcc tcaacgacca    720
cagccaccac ggcccaggag cccgccacct cccaccccca cagggacatg cagcctggcc    780
accatgagac ctcaaccccct gcaggaccca gccaagctga ccttcacact ccccacacag   840
aggatggagt ccttctgcc accgagaggg ctgctgagga tggagcctcc agtcagctcc     900
cagcagcaga gggctctggg gagcaggact tcacctttga aacctcgggg gagaatacgg    960
ctgtagtggc cgtggagcct gaccgccgga accagtcccc agtggatcag ggggccacgg    1020
gggcctcaca gggcctcctg gacaggaaag aggtgctggg aggggtcatt gccggaggcc    1080
tcgtggggct catctttgct gtgtgcctgg tgggtttcat gctgtaccgc atgaagaaga    1140
aggacgaagg cagctactcc ttggaggagc cgaaacaagc caacggcggg gcctaccaga    1200
agcccaccaa acaggaggaa ttctatgcct gacgcgggag ccatgcgccc cctccgccct    1260
gccactcact aggcccccac ttgcctcttc cttgaagaac tgcaggccct ggcctcccct    1320
gccaccaggc cacctcccca gcattccagc ccctctggtc gctcctgccc acggagtcgt    1380
ggggtgtgct gggagctcca ctctgcttct ctgacttctg cctggagact tagggcacca    1440
ggggtttctc gcataggacc tttccaccac agccagcacc tggcatcgca ccattctgac    1500
tcggtttctc caaactgaag cagcctctcc ccaggtccag ctctggaggg gaggggatc     1560 cgactgcttt ggacctaaat ggcctcatgt ggctggaaga tcctgcgggt ggggcttggg    1620
gctcacacac ctgtagcact tactggtagg accaagcatc ttgggggggt ggccgctgag    1680
tggcagggga caggagtcca ctttgtttcg tggggaggtc taatctagat atcgacttgt    1740
ttttgcacat gtttcctcta gttctttgtt catagcccag tagaccttgt tacttctgag    1800
gtaagttaag taagttgatt cggtatcccc ccatcttgct tccctaatct atggtcggga    1860
gacagcatca gggttaagaa gactttttt tttttttttt aaactaggag aaccaaatct    1920
ggaagccaaa atgtaggctt agtttgtgtg ttgtctcttg agtttgtcgc tcatgtgtgc    1980
aacagggtat ggactatctg tctggtggcc ccgtttctgg tggtctgttg gcaggctggc    2040
cagtccaggc tgccgtgggg ccgccgcctc tttcaagcag tcgtgcctgt gtccatgcgc    2100
tcagggccat gctgaggcct gggccgctgc cacgttggag aagcccgtgt gagaagtgaa    2160
tgctgggact cagccttcag acagagagga ctgtagggag ggcggcaggg gcctggagat    2220
cctcctgcag accacgcccg tcctgcctgt ggcgccgtct ccaggggctg cttcctcctg    2280
gaaattgacg agggggtgtct tgggcagagc tggctctgag cgcctccatc caaggccagg    2340
ttctccgtta gctcctgtgg ccccaccctg ggccctgggc tggaatcagg aatattttcc    2400
aaagagtgat agtcttttgc ttttggcaaa actctactta atccaatggg ttttccctg     2460 tacagtagat tttccaaatg taataaactt taatataaag tagtcctgtg aatgccactg    2520
ccttcgcttc ttgcctctgt gctgtgtgtg acgtgaccgg acttttctgc aaacaccaac    2580 atgtttgggaa acttggctcg aatctctgtg ccttcgtctt tcccatgggg agggattctg   2640
gttccagggt ccctctgtgt atttgctttt ttgttttggc tgaaattctc ctggaggtcg    2700
gtaggttcag ccaaggtttt ataaggctga tgtcaatttc tgtgttgcca agctccaagc    2760
cccatcttct aaatggcaaa ggaaggtgga tggcccagc acagcttgac ctgaggctgt     2820
ggtcacagcg gaggtgtgga gccgaggcct accccgcaga caccttggac atcctcctcc    2880
cacccggctg cagaggccag aggccccag cccagggctc ctgcacttac ttgcttattt     2940
gacaacgttt cagcgactcc gttggccact ccgagaggtg ggccagtctg tggatcagag    3000
atgcaccacc aagccaaggg aacctgtgtc cggtattcga tactgcgact ttctgcctgg    3060
```

```
agtgtatgac tgcacatgac tcggggtgg ggaaagggt cggctgacca tgctcatctg    3120
ctggtccgtg ggacggtgcc caagccagag gctgggttca tttgtgtaac gacaataaac   3180
ggtacttgtc atttcgggca aaaaaaaaaa aaaaaa                            3217
```

<210> SEQ ID NO 2
<211> LENGTH: 310
<212> TYPE: PRT
<213> ORGANISM: Homo sapiens

<400> SEQUENCE: 2

```
Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310
```

<210> SEQ ID NO 3
<211> LENGTH: 102
<212> TYPE: DNA

<213> ORGANISM: Homo sapiens

<400> SEQUENCE: 3

```
ctgcctccac ctccaccctg ccggctggag aggggcccaa ggagggagag gctgtagtcc    60
tgccagaagt ggagcctggc ctcaccgccc gggagcagga gg                      102
```

<210> SEQ ID NO 4
<211> LENGTH: 34
<212> TYPE: PRT
<213> ORGANISM: Homo sapiens

<400> SEQUENCE: 4

```
Ala Ser Thr Ser Thr Leu Pro Ala Gly Glu Gly Pro Lys Glu Gly Glu
 1               5                  10                  15

Ala Val Val Leu Pro Glu Val Glu Pro Gly Leu Thr Ala Arg Glu Gln
             20                  25                  30

Glu Ala
```

<210> SEQ ID NO 5
<211> LENGTH: 20
<212> TYPE: DNA
<213> ORGANISM: Artificial
<220> FEATURE:
<223> OTHER INFORMATION: Artificial primer

<400> SEQUENCE: 5

```
aggacttcac ctttgaaacc                                                20
```

<210> SEQ ID NO 6
<211> LENGTH: 20
<212> TYPE: DNA
<213> ORGANISM: Artificial
<220> FEATURE:
<223> OTHER INFORMATION: Artificial primer

<400> SEQUENCE: 6

```
aggaggaatt ctatgcctga                                                20
```

<210> SEQ ID NO 7
<211> LENGTH: 19
<212> TYPE: DNA
<213> ORGANISM: Artificial
<220> FEATURE:
<223> OTHER INFORMATION: Artificial primer

<400> SEQUENCE: 7

```
ggtaagttaa gtaagttga                                                 19
```

<210> SEQ ID NO 8
<211> LENGTH: 234
<212> TYPE: PRT
<213> ORGANISM: Homo sapiens

<400> SEQUENCE: 8

```
Gln Pro Ala Leu Pro Gln Ile Val Ala Thr Asn Leu Pro Pro Glu Asp
 1               5                  10                  15

Gln Asp Gly Ser Gly Asp Asp Ser Asp Asn Phe Ser Gly Ser Gly Ala
             20                  25                  30

Gly Ala Leu Gln Asp Ile Thr Leu Ser Gln Gln Thr Pro Ser Thr Trp
         35                  40                  45

Lys Asp Thr Gln Leu Leu Thr Ala Ile Pro Thr Ser Pro Glu Pro Thr
     50                  55                  60
```

Gly Leu Glu Ala Thr Ala Ala Ser Thr Ser Thr Leu Pro Ala Gly Glu
65                  70                  75                  80

Gly Pro Lys Glu Gly Glu Ala Val Val Leu Pro Glu Val Glu Pro Gly
                85                  90                  95

Leu Thr Ala Arg Glu Gln Glu Ala Thr Pro Arg Pro Arg Glu Thr Thr
            100                 105                 110

Gln Leu Pro Thr Thr His Gln Ala Ser Thr Thr Ala Thr Thr Ala
        115                 120                 125

Gln Glu Pro Ala Thr Ser His Pro His Arg Asp Met Gln Pro Gly His
    130                 135                 140

His Glu Thr Ser Thr Pro Ala Gly Pro Ser Gln Ala Asp Leu His Thr
145                 150                 155                 160

Pro His Thr Glu Asp Gly Gly Pro Ser Ala Thr Glu Arg Ala Ala Glu
                165                 170                 175

Asp Gly Ala Ser Ser Gln Leu Pro Ala Ala Glu Gly Ser Gly Glu Gln
            180                 185                 190

Asp Phe Thr Phe Glu Thr Ser Gly Glu Asn Thr Ala Val Val Ala Val
        195                 200                 205

Glu Pro Asp Arg Arg Asn Gln Ser Pro Val Asp Gln Gly Ala Thr Gly
    210                 215                 220

Ala Ser Gln Gly Leu Leu Asp Arg Lys Glu
225                 230

<210> SEQ ID NO 9
<211> LENGTH: 293
<212> TYPE: PRT
<213> ORGANISM: Homo sapiens

<400> SEQUENCE: 9

Gln Pro Ala Leu Pro Gln Ile Val Ala Thr Asn Leu Pro Pro Glu Asp
1               5                   10                  15

Gln Asp Gly Ser Gly Asp Asp Ser Asp Asn Phe Ser Gly Ser Gly Ala
            20                  25                  30

Gly Ala Leu Gln Asp Ile Thr Leu Ser Gln Gln Thr Pro Ser Thr Trp
        35                  40                  45

Lys Asp Thr Gln Leu Leu Thr Ala Ile Pro Thr Ser Pro Glu Pro Thr
50                  55                  60

Gly Leu Glu Ala Thr Ala Ala Ser Thr Ser Thr Leu Pro Ala Gly Glu
65                  70                  75                  80

Gly Pro Lys Glu Gly Glu Ala Val Val Leu Pro Glu Val Glu Pro Gly
                85                  90                  95

Leu Thr Ala Arg Glu Gln Glu Ala Thr Pro Arg Pro Arg Glu Thr Thr
            100                 105                 110

Gln Leu Pro Thr Thr His Gln Ala Ser Thr Thr Ala Thr Thr Ala
        115                 120                 125

Gln Glu Pro Ala Thr Ser His Pro His Arg Asp Met Gln Pro Gly His
    130                 135                 140

His Glu Thr Ser Thr Pro Ala Gly Pro Ser Gln Ala Asp Leu His Thr
145                 150                 155                 160

Pro His Thr Glu Asp Gly Gly Pro Ser Ala Thr Glu Arg Ala Ala Glu
                165                 170                 175

Asp Gly Ala Ser Ser Gln Leu Pro Ala Ala Glu Gly Ser Gly Glu Gln
            180                 185                 190

Asp Phe Thr Phe Glu Thr Ser Gly Glu Asn Thr Ala Val Val Ala Val

```
                195                 200                 205
Glu Pro Asp Arg Arg Asn Gln Ser Pro Val Asp Gln Gly Ala Thr Gly
    210                 215                 220

Ala Ser Gln Gly Leu Leu Asp Arg Lys Glu Val Leu Gly Gly Val Ile
225                 230                 235                 240

Ala Gly Gly Leu Val Gly Leu Ile Phe Ala Val Cys Leu Val Gly Phe
                245                 250                 255

Met Leu Tyr Arg Met Lys Lys Lys Asp Glu Gly Ser Tyr Ser Leu Glu
            260                 265                 270

Glu Pro Lys Gln Ala Asn Gly Gly Ala Tyr Gln Lys Pro Thr Lys Gln
        275                 280                 285

Glu Glu Phe Tyr Ala
    290

<210> SEQ ID NO 10
<211> LENGTH: 49
<212> TYPE: PRT
<213> ORGANISM: Homo sapiens

<400> SEQUENCE: 10

Gly Leu Glu Ala Thr Ala Ala Ser Thr Ser Thr Leu Pro Ala Gly Glu
1               5                   10                  15

Gly Pro Lys Glu Gly Glu Ala Val Val Leu Pro Glu Val Glu Pro Gly
            20                  25                  30

Leu Thr Ala Arg Glu Gln Glu Ala Thr Pro Arg Pro Arg Glu Thr Thr
        35                  40                  45

Gln

<210> SEQ ID NO 11
<211> LENGTH: 3057
<212> TYPE: DNA
<213> ORGANISM: Mus musculus

<400> SEQUENCE: 11
agctccgcgg gagaggtgcg ggccagagga gacagagcct aacgcagagg aagggacctg      60
gcagtcggga gctgactcca gccggcgaaa cctacagccc tcgctcgaga gagcagcgag     120
ctgggcagga gcctgggaca gcaaagcgca gagcaatcag cagagccggc ccggagctcc     180
gtgcaaccgg caactcggat ccacgaagcc caccgagctc ccgccgccgg tctgggcagc     240
atgagacgcg cggcgctctg gctctggctc tgcgcgctgg cgctgcgcct gcagcctgcc     300
ctcccgcaaa ttgtggctgt aaatgttcct cctgaagatc aggatggctc tggggatgac     360
tctgacaact ctctggctc tggcacaggt gctttgccag atactttgtc acggcagaca     420
ccttccactt ggaaggacgt gtggctgttg acagccacgc ccacagctcc agagcccacc     480
agcagcaaca ccgagactgc tttracctct gtcctgccag ccggagagaa gcccgaggag     540
ggagagcctg tgctccatgt agaagcagag cctggcttca ctgctcggga caaggaaaag     600
gaggtcacca ccaggcccag ggagaccgtg cagctcccca tcacccaacg ggcctcaaca     660
gtcagagtca ccacagccca ggcagctgtc acatctcatc cgcacggggg catgcaacct     720
ggcctccatg agacctcggc tcccacagca cctggtcaac ctgaccatca gcctccacgt     780
gtggagggtg gcggcacttc tgtcatcaaa gaggttgtcg aggatggaac tgccaatcag     840
cttcccgcag gagagggctc tggagaacaa gacttcacct ttgaaacatc tggggagaac     900
acagctgtgg ctgccgtaga gccggcctg cggaatcagc cccggtgga cgaaggagcc     960
```

```
acaggtgctt ctcagagcct tttggacagg aaggaagtgc tgggaggtgt cattgccgga    1020
ggcctagtgg gcctcatctt tgctgtgtgc ctggtggctt tcatgctgta ccggatgaag    1080
aagaaggacg aaggcagcta ctccttggag gagcccaaac aagccaatgg cggtgcctac    1140
cagaaaccca ccaagcagga ggagttctac gcctgatggg gaaatagttc tttctccccc    1200
cacagcccct gccactcact aggctcccac ttgcctcttc tgtgaaaaac ttcaagccct    1260
ggcctcccca ccactgggtc atgtcctctg cacccaggcc cttccagctg ttcctgcccg    1320
agcggtccca gggtgtgctg ggaactgatt cccctccttt gacttctgcc tagaagcttg    1380
ggtgcaaagg gtttcttgca tctgatcttt ctaccacaac cacacctgtc gtccactctt    1440
ctgacttggt ttctccaaat gggaggagac ccagctctgg acagaaaggg gacccgactg    1500
ctttggacct agatggccta ttgcggctgg aggatcctga ggacaggaga ggggcttcgg    1560
ctgaccagcc atagcactta cccatagaga ccgctagggt tggccgtgct gtggtggggg    1620
atggaggcct gagctccttg gaatccactt tcattgtgg ggaggtctac tttagacaac     1680
ttggttttgc acatattttc tctaatttct ctgttcagag ccccagcaga ccttattact    1740
ggggtaaggc aagtctgttg actggtgtcc ctcacctcgc ttccctaatc tacattcagg    1800
agaccgaatc gggggttaat aagactttt ttgtttttg tttttgttt taacctagaa       1860
gaaccaaatc tggacgccaa acgtaggct tagtttgtgt gttgtctctg agtttgtcgc     1920
tcatgcgtac aacagggtat ggactatctg tatggtgccc cattttggc ggcccgtaag     1980
taggctggct agtccaggat actgtggaat agccacctct tgaccagtca tgcctgtgtg    2040
catggactca gggccacggc cttggcctgg gccaccgtga cattggaaga gcctgtgtga    2100
gaacttactc gaagttcaca gtctaggagt ggaggggagg agactgtaga gttttggggg    2160
aggggtggca agggtgccca agcgtctccc accttggta ccatctctag tcatccttcc     2220
tcccggaagt tgacaagaca catcttgagt atggctggca ctggttcctc catcaagaac    2280
caagttcacc ttcagctcct gtggccccgc cccaggctg gagtcagaaa tgtttcccaa     2340
agagtgagtc ttttgctttt ggcaaaacgc tacttaatcc aatgggttct gtacagtaga    2400
ttttgcagat gtaataaact ttaatataaa ggagtcctat gaactctact gcttctgctt    2460
cttcttctct ggactggtgg tatagatata gccacccttt gcccaaaccc tggtagctcg    2520
gggaagcttg gcttaaggct gcacgcctcc aatcccccaa agggtaggat cctggctggg    2580
tccagggttc ctctgattta tttggttttg ttgtgttgtg ttgtgttttt cttttggcta    2640
aacttcttt ggaagttggt aagttcagcc aaggttttac aggccctgat gtctgttctt     2700
ctaaatggtt taagtaattg ggactctagc acatcttgac ctagggtcac tagagctaag    2760
cttgctttgc agggcagaca cctgggacag ccttcctccc tcatgtttgc tgggacactg    2820
ctgagcaccc cttgcttact tagctcagtg atgttccagc tcctggctag gctgctcagc    2880
cactcagcta gacaaaagat ctgtgccctg tgtttcatcc cagagcttgt tgccagatca    2940
catggctgga tgtgatgtgg ggtgggggtg gggtcatatc tgagacagcc ctcagctgag    3000
ggcttgtggg acagtgtcca agcctcaggc tgggctcatt catataattg caataaa      3057
```

<210> SEQ ID NO 12
<211> LENGTH: 311
<212> TYPE: PRT
<213> ORGANISM: Mus musculus

<400> SEQUENCE: 12

Met Arg Arg Ala Ala Leu Trp Leu Trp Leu Cys Ala Leu Ala Leu Arg

```
             1               5                  10                 15
           Leu Gln Pro Ala Leu Pro Gln Ile Val Ala Val Asn Val Pro Pro Glu
                            20                 25                 30

Asp Gln Asp Gly Ser Gly Asp Ser Asp Asn Phe Ser Gly Ser Gly
                            35                 40                 45

Thr Gly Ala Leu Pro Asp Thr Leu Ser Arg Gln Thr Pro Ser Thr Trp
            50                 55                 60

Lys Asp Val Trp Leu Leu Thr Ala Thr Pro Thr Ala Pro Glu Pro Thr
           65                 70                 75                 80

Ser Ser Asn Thr Glu Thr Ala Phe Thr Ser Val Leu Pro Ala Gly Glu
                            85                 90                 95

Lys Pro Glu Glu Gly Glu Pro Val Leu His Val Glu Ala Glu Pro Gly
                            100                105                110

Phe Thr Ala Arg Asp Lys Glu Lys Glu Val Thr Thr Arg Pro Arg Glu
                            115                120                125

Thr Val Gln Leu Pro Ile Thr Gln Arg Ala Ser Thr Val Arg Val Thr
                            130                135                140

Thr Ala Gln Ala Ala Val Thr Ser His Pro His Gly Gly Met Gln Pro
           145                150                155                160

Gly Leu His Glu Thr Ser Ala Pro Thr Ala Pro Gly Gln Pro Asp His
                            165                170                175

Gln Pro Pro Arg Val Glu Gly Gly Thr Ser Val Ile Lys Glu Val
                            180                185                190

Val Glu Asp Gly Thr Ala Asn Gln Leu Pro Ala Gly Glu Gly Ser Gly
                            195                200                205

Glu Gln Asp Phe Thr Phe Glu Thr Ser Gly Glu Asn Thr Ala Val Ala
                            210                215                220

Ala Val Glu Pro Gly Leu Arg Asn Gln Pro Pro Val Asp Glu Gly Ala
           225                230                235                240

Thr Gly Ala Ser Gln Ser Leu Leu Asp Arg Lys Glu Val Leu Gly Gly
                            245                250                255

Val Ile Ala Gly Gly Leu Val Gly Leu Ile Phe Ala Val Cys Leu Val
                            260                265                270

Ala Phe Met Leu Tyr Arg Met Lys Lys Lys Asp Glu Gly Ser Tyr Ser
                            275                280                285

Leu Glu Glu Pro Lys Gln Ala Asn Gly Gly Ala Tyr Gln Lys Pro Thr
                            290                295                300

Lys Gln Glu Glu Phe Tyr Ala
           305                310

<210> SEQ ID NO 13
<211> LENGTH: 34
<212> TYPE: PRT
<213> ORGANISM: Artificial
<220> FEATURE:
<223> OTHER INFORMATION: Artificial peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
```

```
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 13

Xaa Thr Ser Xaa Leu Pro Ala Gly Glu Xaa Pro Xaa Glu Gly Glu Xaa
1               5                   10                  15

Val Xaa Xaa Xaa Glu Xaa Glu Pro Xaa Xaa Thr Ala Arg Xaa Xaa Glu
            20                  25                  30

Xaa Glu

<210> SEQ ID NO 14
<211> LENGTH: 90
<212> TYPE: PRT
<213> ORGANISM: Artificial
<220> FEATURE:
<223> OTHER INFORMATION: Artificial peptide

<400> SEQUENCE: 14

Trp Leu Leu Thr Ala Thr Pro Thr Ala Pro Glu Pro Thr Ser Ser Asn
1               5                   10                  15

Thr Glu Thr Ala Phe Thr Ser Val Leu Pro Ala Gly Glu Lys Pro Glu
                20                  25                  30

Glu Gly Glu Pro Val Leu His Val Glu Ala Glu Pro Gly Phe Thr Ala
            35                  40                  45

Arg Asp Lys Glu Lys Glu Val Thr Thr Arg Pro Arg Glu Thr Val Gln
        50                  55                  60

Leu Pro Ile Thr Gln Arg Ala Ser Thr Val Arg Val Thr Thr Ala Gln
65                  70                  75                  80

Ala Ala Val Thr Ser His Pro His Gly Gly
                85                  90

<210> SEQ ID NO 15
<211> LENGTH: 34
<212> TYPE: PRT
<213> ORGANISM: Artificial
<220> FEATURE:
<223> OTHER INFORMATION: Artificial peptide

<400> SEQUENCE: 15

Phe Thr Ser Val Leu Pro Ala Gly Glu Lys Pro Glu Glu Gly Glu Pro
1               5                   10                  15
```

Val Leu His Val Glu Ala Glu Pro Gly Phe Thr Ala Arg Asp Lys Glu
            20                  25                  30

Lys Glu

<210> SEQ ID NO 16
<211> LENGTH: 90
<212> TYPE: PRT
<213> ORGANISM: Artificial
<220> FEATURE:
<223> OTHER INFORMATION: Artificial peptide

<400> SEQUENCE: 16

Trp Leu Leu Thr Ala Thr Pro Thr Ala Pro Glu Pro Thr Ser Arg Asp
1               5                   10                  15

Ala Gln Ala Thr Thr Thr Ser Ile Leu Pro Ala Ala Glu Lys Pro Gly
            20                  25                  30

Glu Gly Glu Pro Val Leu Thr Ala Glu Val Asp Pro Gly Phe Thr Ala
        35                  40                  45

Arg Asp Lys Glu Ser Glu Val Thr Thr Arg Pro Arg Glu Thr Thr Gln
    50                  55                  60

Leu Leu Ile Thr His Trp Val Ser Thr Ala Arg Ala Thr Thr Ala Gln
65                  70                  75                  80

Ala Pro Val Thr Ser His Pro His Arg Asp
                85                  90

<210> SEQ ID NO 17
<211> LENGTH: 34
<212> TYPE: PRT
<213> ORGANISM: Artificial
<220> FEATURE:
<223> OTHER INFORMATION: Artificial peptide

<400> SEQUENCE: 17

Thr Thr Ser Ile Leu Pro Ala Ala Glu Lys Pro Gly Glu Gly Glu Pro
1               5                   10                  15

Val Leu Thr Ala Glu Val Asp Pro Gly Phe Thr Ala Arg Asp Lys Glu
            20                  25                  30

Ser Glu

<210> SEQ ID NO 18
<211> LENGTH: 91
<212> TYPE: PRT
<213> ORGANISM: Artificial
<220> FEATURE:
<223> OTHER INFORMATION: Artificial peptide

<400> SEQUENCE: 18

Trp Leu Leu Thr Ala Thr Pro Thr Ala Pro Glu Pro Thr Ser Arg Asp
1               5                   10                  15

Thr Glu Ala Thr Leu Thr Ser Ile Leu Pro Ala Gly Glu Lys Pro Glu
            20                  25                  30

Glu Gly Glu Pro Val Ala His Val Glu Ala Glu Pro Asp Phe Thr Ala
        35                  40                  45

Arg Asp Lys Glu Lys Glu Ala Thr Thr Arg Pro Arg Glu Thr Thr Gln
    50                  55                  60

Leu Pro Val Thr Gln Gln Ala Ser Thr Ala Arg Ala Thr Thr Ala
65                  70                  75                  80

Gln Ala Ser Val Thr Phe His Pro His Gly Asp
                85                  90

<210> SEQ ID NO 19
<211> LENGTH: 34
<212> TYPE: PRT
<213> ORGANISM: Artificial
<220> FEATURE:
<223> OTHER INFORMATION: Artificial peptide

<400> SEQUENCE: 19

Leu Thr Ser Ile Leu Pro Ala Gly Glu Lys Pro Glu Glu Gly Glu Pro
1               5                   10                  15

Val Ala His Val Glu Ala Glu Pro Asp Phe Thr Ala Arg Asp Lys Glu
            20                  25                  30

Lys Glu

<210> SEQ ID NO 20
<211> LENGTH: 89
<212> TYPE: PRT
<213> ORGANISM: Artificial
<220> FEATURE:
<223> OTHER INFORMATION: Artificial peptide

<400> SEQUENCE: 20

Gln Leu Leu Thr Ala Ile Pro Thr Ser Pro Glu Pro Thr Gly Leu Glu
1               5                   10                  15

Ala Thr Ala Ala Ser Thr Ser Thr Leu Pro Ala Gly Glu Gly Pro Lys
            20                  25                  30

Glu Gly Glu Ala Val Val Leu Pro Glu Val Glu Pro Gly Thr Leu Thr
        35                  40                  45

Ala Arg Glu Gln Glu Ala Thr Pro Arg Pro Arg Glu Thr Thr Gln Leu
    50                  55                  60

Pro Thr Thr His Gln Ala Ser Thr Thr Thr Ala Thr Thr Ala Gln Glu
65                  70                  75                  80

Pro Ala Thr Ser His Pro His Arg Asp
                85

<210> SEQ ID NO 21
<211> LENGTH: 32
<212> TYPE: PRT
<213> ORGANISM: Artificial
<220> FEATURE:
<223> OTHER INFORMATION: Artificial peptide

<400> SEQUENCE: 21

Ser Thr Ser Thr Leu Pro Ala Gly Glu Gly Pro Lys Glu Gly Glu Ala
1               5                   10                  15

Val Val Leu Pro Glu Val Glu Pro Gly Leu Thr Ala Arg Glu Gln Glu
            20                  25                  30

<210> SEQ ID NO 22
<211> LENGTH: 49
<212> TYPE: PRT
<213> ORGANISM: Artificial
<220> FEATURE:
<223> OTHER INFORMATION: Artificial peptide

<400> SEQUENCE: 22

Ser Asn Thr Glu Thr Ala Phe Thr Ser Val Leu Pro Ala Gly Glu Lys
1               5                   10                  15

Pro Glu Glu Gly Glu Pro Val Leu His Val Glu Ala Glu Pro Gly Phe
            20                  25                  30

Thr Ala Arg Asp Lys Glu Lys Glu Val Thr Thr Arg Pro Arg Glu Thr 35                  40                  45

Val

<210> SEQ ID NO 23
<211> LENGTH: 35
<212> TYPE: PRT
<213> ORGANISM: Artificial
<220> FEATURE:
<223> OTHER INFORMATION: Artificial peptide

<400> SEQUENCE: 23

Phe Thr Ser Val Leu Pro Ala Gly Glu Lys Pro Glu Glu Gly Glu Pro
1               5                   10                  15

Val Leu His Val Glu Ala Glu Pro Gly Phe Thr Ala Arg Asp Lys Glu
            20                  25                  30

Lys Glu Val
        35

<210> SEQ ID NO 24
<211> LENGTH: 35
<212> TYPE: PRT
<213> ORGANISM: Artificial
<220> FEATURE:
<223> OTHER INFORMATION: Artificial peptide

<400> SEQUENCE: 24

Glu Lys Pro Glu Glu Gly Glu Pro Val Leu His Val Glu Ala Glu Pro
1               5                   10                  15

Gly Phe Thr Ala Arg Asp Lys Glu Lys Glu Val Thr Thr Arg Pro Arg
            20                  25                  30

Glu Thr Val
        35

<210> SEQ ID NO 25
<211> LENGTH: 30
<212> TYPE: PRT
<213> ORGANISM: Artificial
<220> FEATURE:
<223> OTHER INFORMATION: Artificial peptide

<400> SEQUENCE: 25

Phe Thr Ser Val Leu Pro Ala Gly Glu Lys Pro Glu Glu Gly Glu Pro
1               5                   10                  15

Val Leu His Val Glu Ala Glu Pro Gly Phe Thr Ala Arg Asp
            20                  25                  30

<210> SEQ ID NO 26
<211> LENGTH: 19
<212> TYPE: PRT
<213> ORGANISM: Artificial
<220> FEATURE:
<223> OTHER INFORMATION: Artificial peptide

<400> SEQUENCE: 26

Phe Thr Ser Val Leu Pro Ala Gly Glu Lys Pro Glu Glu Gly Glu Pro
1               5                   10                  15

Val Leu His

<210> SEQ ID NO 27
<211> LENGTH: 14
<212> TYPE: PRT
<213> ORGANISM: Artificial
<220> FEATURE:

```
<223> OTHER INFORMATION: Artificial peptide

<400> SEQUENCE: 27

Ser Val Leu Pro Ala Gly Glu Lys Pro Glu Glu Gly Glu Pro
1               5                   10

<210> SEQ ID NO 28
<211> LENGTH: 34
<212> TYPE: PRT
<213> ORGANISM: Artificial
<220> FEATURE:
<223> OTHER INFORMATION: Artificial peptide

<400> SEQUENCE: 28

Ala Ser Thr Ser Thr Leu Pro Ala Gly Glu Gly Pro Lys Glu Gly Glu
1               5                   10                  15

Ala Val Val Leu Pro Glu Val Glu Pro Gly Leu Thr Ala Arg Glu Gln
            20                  25                  30

Glu Ala
```

PEPTIDES OF SYNDECAN-1 FOR INHIBITING ANGIOGENESIS

CROSS-REFERENCE TO RELATED APPLICATIONS

The present application is a divisional of U.S. patent application Ser. No. 13/734,302, filed Jan. 4, 2013, which is a divisional of abandoned U.S. patent application Ser. No. 11/760,594, filed Jun. 8, 2007, which claims the benefit of priority to U.S. Provisional Application No. 60/812,187, filed Jun. 9, 2006, the entire contents of which are hereby incorporated by reference in their entireties.

STATEMENT REGARDING FEDERALLY SPONSORED RESEARCH OR DEVELOPMENT

This invention was made with government support under CA109010 awarded by the National Institutes of Health. The government has certain rights in the invention.

BACKGROUND OF THE INVENTION

I. Field of the Invention

The present invention relates generally to the fields of protein chemistry and developmental biology. More particularly, it concerns peptide segments from the extracellular domain of syndecan-1 (Sdc-1) that can inhibit angiogenesis and can thus be used to treat angiogenesis in pathologic conditions.

II. Description of Related Art

A. Function of $\alpha_v\beta_3$ and $\alpha_v\beta_5$ Integrins in Angiogenesis Several different growth factors, among them fibroblast growth factor (FGF) and vascular endothelial cell growth factor (VEGF), are often released by tumors to cause endothelial cells to undergo angiogenesis. Blood vessels in the vicinity of the tumor respond to VEGF by becoming leaky (thus the alternate name "vascular permeability factor") allowing fibronectin, vitronectin and fibrinogen in the blood to infiltrate the surrounding matrix. These matrix ligands are critical adhesion and activation ligands for the $\alpha_v\beta_3$ and $\alpha_v\beta_5$ integrins, which have roles in the chemotactic migration of the endothelial cells and in the survival of the cells during vessel pruning. A second response to the growth factors, particularly FGF, is the activation of a neovessel development program that relies on Hox master genes (Boudreau et al., 1997; Myers et al., 2000; Myers et al., 2002). HoxD3 is initially expressed and controls a family of genes that are necessary for the initial migration process, including upregulation of the $\alpha_v\beta_3$ integrin, MMPs and uPAR (Boudreau et al., 1997). Expression of HoxD3 is followed by HoxB3, which regulates the morphogenesis leading to the formation of small vessels (Myers et al., 2000), and finally by the HoxD10 gene, which restores the mature phenotype of the cells (Myers et al., 2002); it is HoxD10 that is expressed in resting, stable blood vessels in vivo.

The $\alpha_v\beta_3$ and $\alpha_v\beta_5$ integrins are important not only during endothelial cell migration, but are important players in the survival of the endothelial cells. Although endothelial cells in mature vessels are not readily susceptible to apoptosis, angiogenic cells that are induced by growth factors are highly susceptible and rely upon the continued presence of these factors for survival. This is shown experimentally by inducing angiogenesis with VEGF and causing apoptosis by its withdrawal, and is demonstrated in vivo when the developing ovarian follicle induces angiogenesis by release of VEGF and the newly formed bloods vessels regress when the source of VEGF is lost upon ovulation. Endothelial cells responding to VEGF rely on signaling from the $\alpha_v\beta_5$ integrin in order to prevent this apoptotic process (Brooks et al., 1994; Friedlander et al., 1995). Similarly, endothelial cells responding to fibroblast growth factor (FGF) are susceptible to apoptosis unless there is coordinate signaling from the $\alpha_v\beta_3$ integrin. Thus, inhibitors that disrupt the activation of these two integrins are potential drugs for blocking angiogenesis not only because they can prevent the positive signaling from the integrins that aid in endothelial cell migration and formation of new vessels, but also because they have the potential to elicit "negative" signals that trigger apoptosis and death of the endothelial cell. Furthermore, this mechanism is not confined to endothelial cells and would apply as well to tumor cells or other cells that rely on either of these integrins to initiate disease processes.

B. Syndecans

The syndecan family of cell surface heparan sulfate (HS) proteoglycans is comprised of four vertebrate members. These receptors are expressed on virtually all cell types, although their expression may be altered in disease states such as cancer (Beauvais and Rapraeger, 2004). The syndecan core proteins share a high degree of conservation in their short cytoplasmic and transmembrane (TM) domains; in contrast, their ectodomains (EDs) are divergent with the exception of attachment sites for HS glycosaminoglycans. Via their HS chains, syndecans regulate the signaling of growth factors, chemokines, and morphogens and engage components of the ECM including VN, FN, LN, tenascin, thrombospondin, and the fibrillar COLs (Bernfield et al., 1999).

In addition to the activities of their HS chains, the syndecan core proteins have roles in cell adhesion signaling (Rapraeger, 2000; Tumova et al., 2000). Conserved and variable regions of the syndecan cytoplasmic domains appear critical for binding interactions that lead to adhesion-mediated signaling and reorganization of the actin cytoskeleton (Couchman et al., 2001). Important roles for the TM domain have also been demonstrated for Sdc-1 and syndecan-4 (Sdc-4) (Tkachenko and Simons, 2002; McQuade and Rapraeger, 2003). Perhaps the least expected active protein domain is the syndecan ED, which bears the HS chains. Nonetheless, several emerging studies suggest that the syndecan ED may have important regulatory roles in cell adhesion signaling. Cell spreading and morphogenetic activities in COS-7 and Schwann cells trace in part to the S1ED (Carey et al., 1994; Adams et al., 2001). Raji cells require the Sdc-1 TM domain for initial spreading, but depend on a S1ED activity for cell polarization (McQuade and Rapraeger, 2003). Moreover, inhibition of ARH-77 myeloma and hepatocellular carcinoma cell invasion into a COL I matrix by Sdc-1 also traces to a region of its extracellular core protein domain (Liu et al., 1998; Ohtake et al., 1999).

The activities of other syndecans also trace to their EDs. Overexpression of Syndecan-2 (Sdc-2) in COS-1 and Swiss 3T3 cells induces filipodial extension and deletion mutants of Sdc-2 map activity to the S2ED (Granes et al., 1999). Upregulation of Sdc-2 expression in colon carcinoma cells leads to altered cell morphology and colony formation in soft agar; treatment with recombinant S2ED disrupts these behaviors (Park et al., 2002; Kim et al., 2003). Finally, activated B-lymphocytes, when seeded on S4ED antibodies, exhibit morphological changes and filipodial extensions. Intriguingly, only the S4ED is required for this response, indicating that it may interact with a TM partner to transmit a dendritic signal (Yamashita et al., 1999).

C. $\alpha_v\beta_3$ Integrins are Regulated by Syndecan-1

The inventors' previous work in the MDA-MB-231 cells suggested that cell spreading induced upon anchorage of the cells to an Sdc-1 antibody relies on functional coupling of the syndecan to activated $\alpha_v\beta_3$ integrins (Beauvais and Rapraeger, 2003). This spreading response is rapid (~15-30 min) and occurs even in the absence of an integrin ligand (i.e., spreading is not blocked by cycloheximide or EGTA treatment), so long as the cells are adherent via Sdc-1. Intriguingly, the $\alpha_v\beta_3$-dependent spreading mechanism is blocked by the addition of soluble, recombinant Sdc-1ED, suggesting that anchorage of Sdc-1 to a ligand provides a platform for $\alpha_v\beta_3$ integrin activation and adhesion signaling via binding interaction of the syndecan ED. These findings raised a fundamental question about the role of Sdc-1 in ECM signaling, in particular whether or not Sdc-1 is required for $\alpha_v\beta_3$ activation and signaling in response to a native matrix ligand. The inventors went on, in subsequent studies to show that Sdc-1 is required for signaling though both $\alpha_v\beta_3$ and $\alpha_v\beta_5$, and that inhibition of this function by competitive binding (Sdc-1ED) or siRNA inhibition blocks cell attachment, cell spreading, cell migration and angiogensis (unpublished).

SUMMARY OF THE INVENTION

Thus, in accordance with the present invention, there is provided an isolated and purified peptide or polypeptide segment consisting of between 5 and 100 amino acid residues and comprising SEQ ID NO:21 or SEQ ID NO:13. In certain embodiments, the peptide does not have an amino acid sequence that consists of SEQ ID NO:28, that is, the peptide differs from SEQ ID NO:28.

The peptide or polypeptide may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues in length, or any range derivable therein. In some embodiments, the peptide or polypeptide is between 10 and 80, 20 and 50, or 30 and 40 amino acid residues in length.

In some embodiments, the peptide may consist of SEQ ID NO:1 or SEQ ID NO:10. In other embodiments, the peptide may consist of or comprise SEQ ID NO:1, SEQ ID NO:13, SEQ ID NO:21, SEQ ID NO:23, or SEQ ID NO:28.

In further embodiments, the peptide or polypeptide comprises at least or at most 35, 36, 37, 38, 39, 40, 41, 42, 43, 44, 45, 47, 47, 48, or 49 contiguous amino acids from SEQ ID NO:10, or any range derivable therein. In additional embodiments, the peptide or polypeptide comprises at least or at most 20, 21, 22, 23, 24, 25, 26, 27, 28, 29, 30, 31, 32, 33, 34, 35, 36, 37, 38, 39, 40, 41, 42, 43, 44, 45, 47, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous amino acids from SEQ ID NOs:14, 16, 18, or 20, or any range derivable therein. It is also contemplated that in certain embodiments, the peptide or polypeptide is at least 90%, 85%, 90%, 95%, or 100% identical to any specified length of a peptide based on SEQ ID NOs:14, 16, 18, or 20. For instance, peptides or polypeptides of the invention may be 30-40 amino acids in length with at least 90% identity to a sequence of that length from SEQ ID NO:20.

It is specifically contemplated that any embodiment relating to a peptide or polypeptide of the invention may be implemented in any other embodiment of the invention, including in methods of the invention.

In another embodiment, there is provided a nucleic acid encoding a peptide or polypeptide segment consisting of between 5 and 100 amino acid residues and comprising SEQ ID NO:10. The nucleic acid may encode a peptide or polypeptide of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues in length, or any range derivable therein. The nucleic acid encodes a peptide consisting of SEQ ID NO:10. In other embodiments, the nucleic acid encodes a peptide consisting of or comprising SEQ ID NO:1, SEQ ID NO:13, SEQ ID NO:21, SEQ ID NO:23, or SEQ ID NO:28.

In yet another embodiment, there is provided a recombinant cell comprising a nucleic acid encoding a peptide or polypeptide segment consisting of between 5 and 100 amino acid residues and comprising SEQ ID NO:21 or SEQ ID NO:13, or any amino acid segment discussed above. The cell may be a bacterial cell. The cell may comprise a nucleic acid further encoding a peptide tag fused to the nucleic acid encoding said peptide segment.

In still yet another embodiment, there is provided a pharmaceutical composition comprising an isolated and purified peptide or polypeptide segment consisting of between 5 and 100 amino acid residues and comprising SEQ ID NO:21 or SEQ ID NO:13 (or any amino acid segment discussed above) dispersed in a pharmaceutically acceptable buffer or diluent. In certain embodiments, the peptide does not have an amino acid sequence that consists of SEQ ID NO:28.

In a further embodiment, there is provided a method of inhibiting interaction of $\alpha_v\beta_3$ or $\alpha_v\beta_5$ integrin with syndecan-1 comprising contacting a $\alpha_v\beta_3$ or $\alpha_v\beta_5$ integrin molecule with a peptide or polypeptide segment consisting of between 5 and 100 amino acid residues or less residues and comprising SEQ ID NO:21 or SEQ ID NO:13. The peptide or polypeptide may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 amino acid residues in length, or any range derivable therein. In certain embodiments, the peptide does not have an amino acid sequence that consists of SEQ ID NO:28. The peptide may consist of SEQ ID NO:10. In other embodiments, the peptide may consist of or comprise SEQ ID NO:1, SEQ ID NO:13, SEQ ID NO:21, SEQ ID NO:23, or SEQ ID NO:28. The $\alpha_v\beta_3$ or $\alpha_v\beta_5$ integrin may be located on the surface of a cell, such as a cancer cell (e.g., a carcinoma, a myeloma, a melanoma or a glioma), including a metastatic cancer cell. The method may further comprise contacting said cancer cell with a second cancer inhibitory agent.

In yet a further embodiment, there is provided a method of inhibiting $\alpha_v\beta_3$ or $\alpha_v\beta_5$ integrin activation by syndecan-1 comprising contacting a cell expressing an $\alpha_v\beta_3$ or $\alpha_v\beta_5$ integrin molecule with a peptide or polypeptide segment consisting of between 5 and 100 amino acid residues and comprising SEQ ID NO:21 or SEQ ID NO:13. In certain embodiments, the peptide does not have an amino acid sequence that consists of SEQ ID NO:28. The peptide or polypeptide may be 10, 15, 20, 25, 30, 35, 40, 45, 49, 50, 55, 60, 65, 70, 75, 80, 85, 90, 95 or 100 amino acid residues in length. The peptide may consist of SEQ ID NO:10. In other embodiments, the peptide may consist of or comprise SEQ ID NO:1, SEQ ID NO:13, SEQ ID NO:21, SEQ ID NO:23, or SEQ ID NO:28. The inhibiting may result in inhibition of cell adhesion, migration, cell metastasis, cell survival and/or cell proliferation.

In still yet a further embodiment, there is provided a method of treating a subject with a cancer, cells of which express $\alpha_v\beta_3$ or $\alpha_v\beta_5$ integrin, comprising contacting said cells with a peptide or polypeptide segment consisting of between 5 and 100 amino acid residues or less residues and comprising SEQ ID NO:21 or SEQ ID NO:13. In certain embodiments, the peptide does not have an amino acid sequence that consists of SEQ ID NO:28. The peptide or polypeptide may be 10, 15, 20, 25, 30, 35, 40, 45, 49, 50, 55, 60, 65, 70, 75, 80, 85, 90, 95 or 100 amino acid residues in length. The peptide may consist of SEQ ID NO:10. In other embodiments, the peptide may consist or comprise SEQ ID NO:1, SEQ ID NO:13, SEQ ID NO:21, SEQ ID NO:23, or SEQ ID NO:28. The subject may be a human. The cancer may be a carcinoma, a myeloma, a melanoma or a glioma. The peptide or polypeptide may be administered directly to said cancer cells, local to said cancer cells, regional to said cancer cells, or systemically. The method may further comprise administering to said subject a second cancer therapy selected from chemotherapy, radiotherapy, immunotherapy, hormonal therapy, or gene therapy.

In an additional embodiment, there is provided a method of inhibiting angiogenesis comprising contacting an endothelial cell expressing an $\alpha_v\beta_3$ or $\alpha_v\beta_5$ integrin molecule with a peptide or polypeptide segment consisting of between 5 and 100 amino acid residues and comprising SEQ ID NO:21 or SEQ ID NO:13. In certain embodiments, the peptide does not have an amino acid sequence that consists of SEQ ID NO:28. The peptide or polypeptide may be 10, 15, 20, 25, 30, 35, 40, 45, 49, 50, 55, 60, 65, 70, 75, 80, 85, 90, 95 or 100 amino acid residues in length. The peptide may consist of SEQ ID NO:10. In other embodiments, the peptide may consist of or comprise SEQ ID NO:1, SEQ ID NO:13, SEQ ID NO:21, SEQ ID NO:23, or SEQ ID NO:28.

In still an additional embodiment, there is provided a method of treating a subject having a disease characterized by angiogenesis comprising contacting endothelial cells which express $\alpha_v\beta_3$ or $\alpha_v\beta_5$ integrin and are responsible for said angiogenesis, with a peptide or polypeptide segment consisting of between 5 and 100 amino acid residues or less residues and comprising at least or at most 10, 11, 12, 13, 14, 15, 16, 171, 18, 19, 20, 21, 22, 23, 24, 25, 26, 27, 28, 29, 30, 31 or 32 contiguous amino acids from a synstatin sequence (or any range derivable therein), such as those defined by SEQ ID NOs:15, 17, 19, and 21. In certain embodiments, the segment comprises SEQ ID NO:21 or SEQ ID NO:13. In certain embodiments, the peptide does not have an amino acid sequence that consists of SEQ ID NO:28. The peptide or polypeptide may be 10, 15, 20, 25, 30, 35, 40, 45, 49, 50, 55, 60, 65, 70, 75, 80, 85, 90, 95 or 100 amino acid residues in length. The peptide may consist of SEQ ID NO:10. In other embodiments, the peptide may consist of or comprise SEQ ID NO:1, SEQ ID NO:13, SEQ ID NO:21, SEQ ID NO:23, or SEQ ID NO:28. The disease may be an abonormality of the vasculature (atherosclerosis and hemangiomas), of the eye (diabetic retinopathy and retinopathy of prematurity), of the skin (pyogenic granulomas, psoriasis, warts, scar keloids, allergic edema, ulcers), of the uterus and ovary (dysfunctional uterine bleeding, follicular cysts, endometriosis, pre-eclampsia), of the adipose tissue (obesity), of the bones and joints (rheumatoid arthritis, osteophyte formation), and AIDS-related pathologies resulting from TAT protein of the human immunodeficiency virus (HIV) activating the avb3 integrin on endothelial cells. In certain embodiments, the disease is particularly not cancer. The contacting may comprise systemic administration of said peptide or polypeptide or administration of said peptide or polypeptide local to said endothelial cells. The peptide or polypeptide may be active at 0.3 µM, at 0.2 µM or at 0.1 µM, or between 0.1 µM and 0.3 The method may further comprise contacting said endothelial cells with a second antiagiogenic agent.

It is further contemplated that peptides or polypeptides of the invention may also include amino acid segments from other proteins. These peptides and polypeptides would have an amino acid sequence from a non-syndecan-1 protein. Consequently, peptides or polypeptides of the invention may consist essentially of a syndecan-1 amino acid segment, such as those discussed herein, in which case they can have an amino acid segment from another protein. In particular embodiments, the other protein can be some kind of marker, targeting sequence, or stabilizer.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed.

(FIG. 1A) Wnt-1 induced mammary tumor. (FIG. 1B) β-catenin-induced mammary tumor. (FIG. 1C) Normal mouse artery. Endothelial cells are identified by staining with a rat monoclonal for PECAM. The integrin subunits are identified by staining with rabbit polyclonal antibodies to the β3 subunit (AB1932), β5 subunit (AB1926) and αV subunit (AB1930). Sdc1 is visualized by an affinity purified rabbit polyclonal antibody directed against its extracellular domain. Rat IgG and Rabbit IgG controls are shown. The staining in the artery is shown as an overlay of the two antibodies used. Note that neither Sdc1 nor the two integrins are expressed in the PECAM-positive endothelial cell layer, whereas they are in the tumors.

FIGS. 5A-5F—Inhibition of MDA-MB-231 human mammary carcinoma cell attachment and spreading on VN by synstatins$_{82-130}$. MDA-MB-231 human mammary carcinoma cells, which rely on the αvβ$_3$ integrin for attachment and spreading on VN, were plated on 10 μg/ml VN for 2 hr in the absence of peptide (FIG. 5A) or in the presence of 0.1 (FIG. 5B), 0.3 (FIG. 5C) or 1 (FIG. 5D) synstatins$_{82-130}$. The cells were fixed and stained as in FIG. 2. (FIGS. 5E-5F) As a control, cell adhesion and spreading on fibronectin, a ligand on which the cells use the α5β1 integrin and do not rely on the αvβ3 integrin; the control with no treatment (FIG. 5E) appears the same as when treated, i.e., synstatin$_{82-130}$ has no effect on attachment and spreading on this ligand (FIG. 5F).

(FIG. 7A) mouse with FGF alone; (FIG. 7B) fluorescence image of the boxed area shown in FIG. 7A; (FIG. 7C) mouse with FGF+systemic synstatins$_{82-130}$; (FIG. 7D) fluorescence image of boxed area shown in FIG. 7C. Note that the cornea is devoid of angiogenic vessels in the presence of systemic synstatin. Normal vessels are observed in the iris.

(FIG. 8A) Diagram of mouse syndecan-4 (mS4), human syndecan-1 (hS1) and mouse syndecan-1 (mS1) and mS1 deletion mutants showing which proteoglycans are able to activate the α$_v$β$_3$ and α$_v$β$_5$ integrins. (FIG. 8B) Flow cytometry of human aortic endothelial cells (HAEC), human dermal microvascular endothelial cells (HMEC-1) or mouse aortic endothelial cells (MAEC) using human or mouse-specific antibodies for syndecan-1, α$_v$β$_3$, and α$_v$β$_5$. The β$_5$ subunit is detected by Western blot in mouse cells and is compared to B82L fibroblasts known to express this integrin; (FIG. 8C) Human syndecan-1 is immunoprecipitated from HMEC-1 cells in the presence or absence of 30 μM GST, 30 μM GST-mS1ED (mouse syndecan-1 ectodomain), or 1 SSTN and detected on blots along with co-precipitating β$_3$ or β$_5$ integrin. (FIG. 8D) Human syndecan-1 is immunoprecipitated from MDA-MB-231 human mammary carcinoma cells expressing full-length mouse syndecan-1 (Fl-mS1), a mouse mutant bearing deletion of amino acids 67-121 (mS1$^{Δ67-121}$), or vector alone (NEO) and blotted for the co-precipitation of the α$_v$β$_3$ integrin by detection of the β$_3$ subunit.

FIG. 9—Sequence of SSTN across species. The sequence of syndecan-1 in the vicinity of the α$_v$β$_3$ and α$_v$β$_5$ regulatory site is shown for murine, hamster, rat and human. The numbering is for the murine sequence. The active site defined by deletion analysis is amino acids 88-121 in the mouse sequence. Note that human syndecan-1 has one additional amino acid N-terminal to the SSTN sequence; thus its numbering would be greater by one amino acid. A putative conserved sequence (cons) is shown (SEQ ID NO:13) (72% homology).

murS1 shown is SEQ ID NO:14 and synstatin sequence is SEQ ID NO:15.

hamS1 is SEQ ID NO:16 and synstatin sequence is SEQ ID NO:17.

ratS 1 is SEQ ID NO:18 and synstatin sequence is SEQ ID NO:19.

humS1 is SEQ ID NO:20 and synstatin sequence is SEQ ID NO:21.

FIGS. 10A-10D—Dependence of HMEC cell attachment and spreading on integrin activation by Sdc1 and its inhibition by SSTN. (FIG. 10A) HMECs were plated for 2 hr either on Sdc1-specific antibody B-B4 to engage Sdc1 or on VN (10 μg/ml coating concentration) to engage the α$_v$β$_3$ and α$_v$β$_5$ integrins. Blocking antibodies LM609 (10 μg/ml, specific for α$_v$β$_3$) and P1F6 (10 μg/ml, specific for α$_v$β$_5$), SSTN (0.5 μM) or recombinant mouse Sdc1 ectodomain (mS1ED, 5 μM) were added. The ligand mimetic antibody WOW1 was used to detect activated α$_v$β$_3$ integrin on cells plated on B-B4. (FIG. 10B) HMECs were treated with siRNA oligo specific for human Sdc1 for 48 hr prior to plating on VN. Sdc1 expression was quantified by flow cytometry using human Sdc1-specific mAb B-B4 or a control mouse IgG. (FIG. 10C-10D) The percentage of cell attaching or attaching and spreading was quantified for HMECs, HAEC and MAECs plated on VN for 24 hr in the presence of mS1ED or SSTN, or after siRNA silencing of Sdc1 expression in the presence of mAb LM609 to block α$_v$β$_3$ integrin, P1F6 to block integrin, or both antibodies.

FIGS. 11A-11C—Syndecdan-1 and the α$_v$β$_3$ and α$_v$β$_5$ integrin are co-expressed during aortic angiogenesis and in tumors. (FIG. 11A) Aortic explants were stained en face for expression of syndecan-1, α$_v$β$_3$ and α$_v$β$_5$ integrin (α$_v$, β$_3$ and β$_5$) and PECAM. (FIG. 11B) Aortic segments explanted to collagen gels in the presence of 30 ng/ml fibroblast growth factor-2 (FGF-2) were stained after 7 days for expression of syndecan-1 and β$_3$ or β$_5$ integrin. (FIG. 11C) Frozen sections of spontaneous mouse mammary tumors from the wnt-1 or β-catenin overexpressing mice were stained for syndecan-1, PECAM, of integrin expression (α$_v$, β$_3$, β$_5$).

Figure 12:
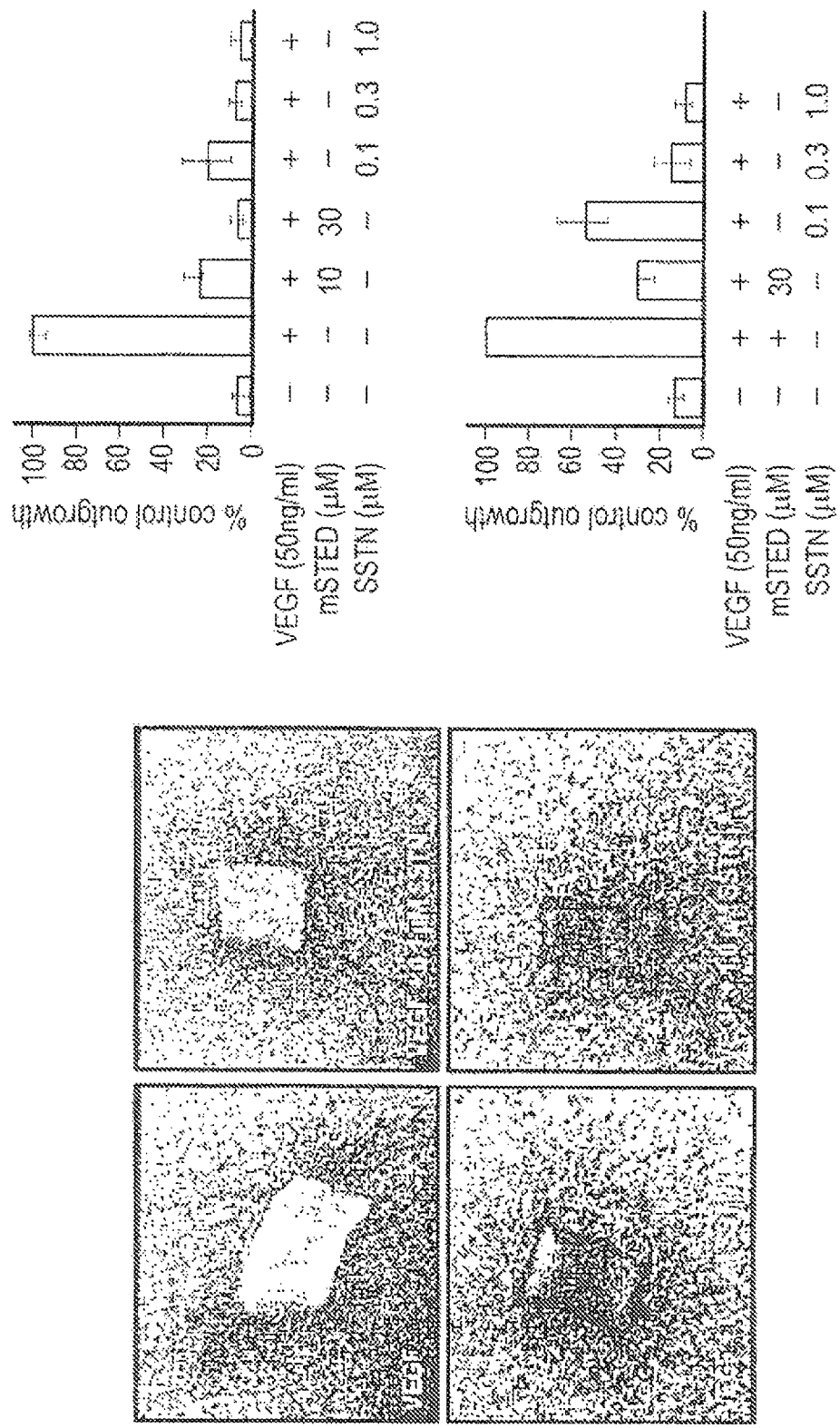

FIG. 12—SSTN blocks aortic ring angiogenesis. Aortic segments were explanted to collagen gels for 7 days in the presence of 50 ng/ml vascular endothelial cell growth factor (VEGF), or 30 ng/ml FGF-2 in the presence or absence of mS1ED or SSTN. Total outgrowth in quantified as the total length of all microvessels.

Figure 13:
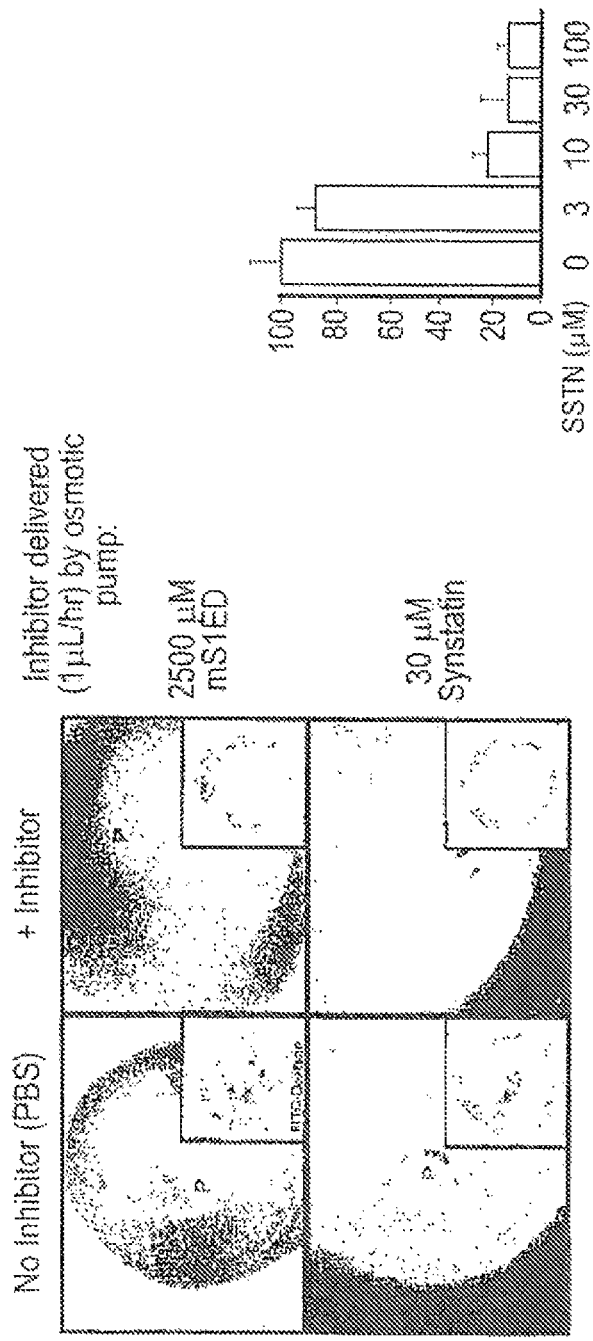

FIG. 13—Inhibition of corneal angiogenesis by SSTN. PolyHEMA pellets (0.25 µL) containing 67 ng FGF-2 and sucralfate were implanted into the avascular mouse cornea. Alzet pumps containing PBS, 2500 µM mS1ED or a range of SSTN concentrations (0-100 µM) were implanted subcutaneously on the back of the animals and angiogenesis for 7 days. Fluorescent dextran was injected suborbitally for 2 min prior to sacrifice for observation of the vascular system in dissected cornea (picture insets). Total angiogenesis is quantified as total length of vessels growing from the limbic vessels at the margin of the cornea.

Figure 14:
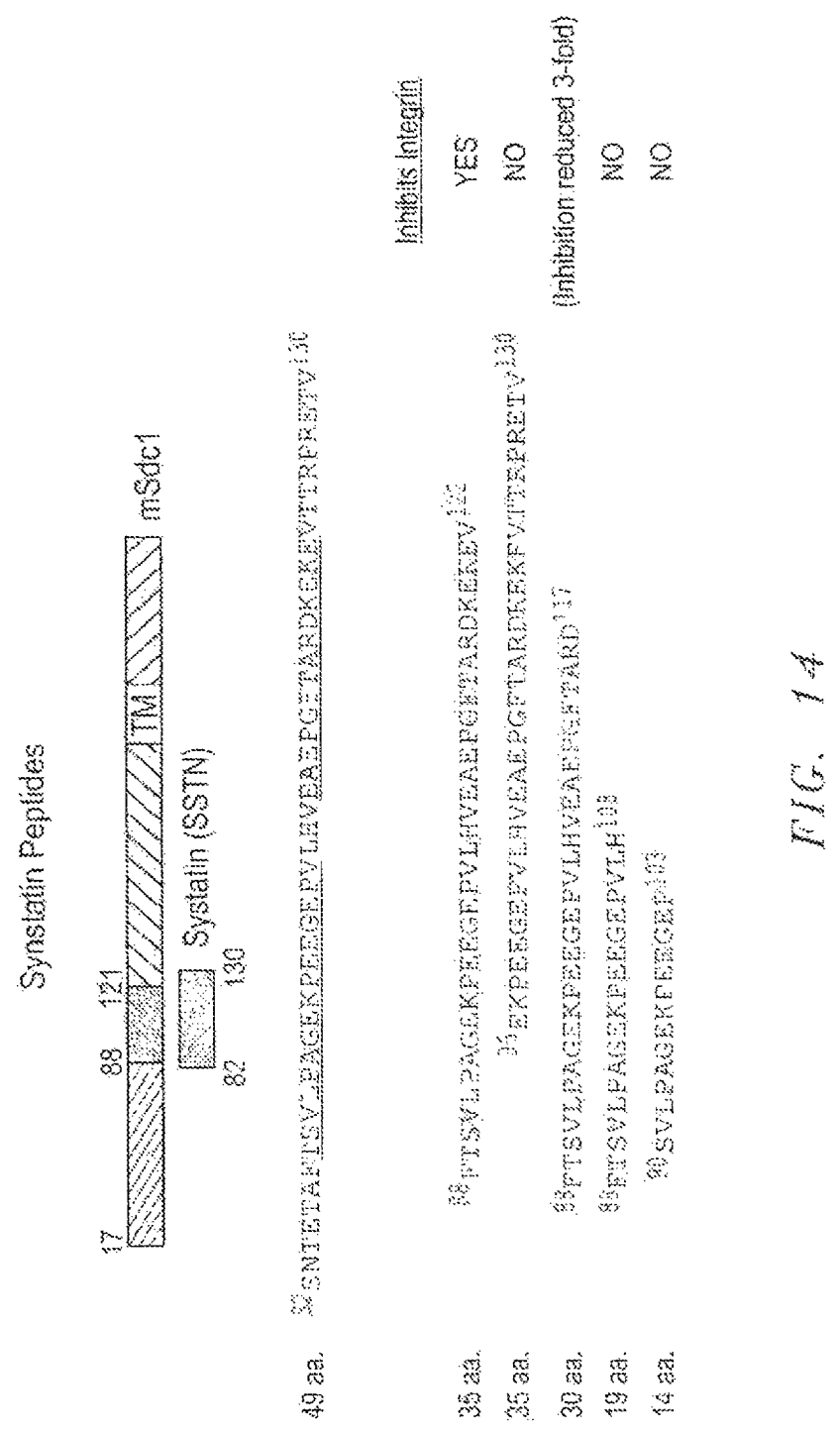

FIG. 14—Activity of SSTN peptides. A diagram of $SSTN_{82-130}$ used in our experiments is shown. The gray letters designate amino acids that are identical or highly conserved across species (mouse, human, rat, hamster). Shorter peptides have been tested using HMEC-1 endothelial cells for inhibition of $\alpha_v\beta_3$ and $\alpha_v\beta_5$ mediated cell attachment and spreading in comparison to $SSTN_{82-130}$.

$SSTN_{82-130}$ (49-mer) is SEQ ID NO:22. $SSTN_{88-122}$ (35-mer) is SEQ ID NO:23. $SSTN_{96-130}$ (35-mer) is SEQ ID NO:24. $SSTN_{88-117}$ (30-mer) is SEQ ID NO:25. $SSTN_{88-106}$ (19-mer) is SEQ ID NO:26. $SSTN_{90-103}$ (14-mer) is SEQ ID NO:27.

Figure 15:
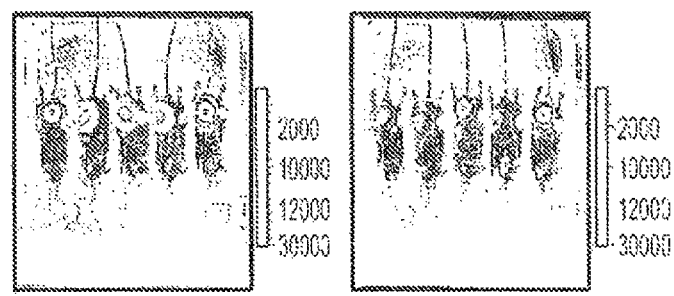

FIG. 15—SSTN-treated mice bearing CAG human myeloma tumors. $10^5$ human CAG myeloma cells were injected subcutaneously into the backs of immunodeficient SCID mice. After 10 days, the mice were scanned to confirm establishment of luciferase-expressing tumors in all ten mice. Alzet pumps delivering 0.25 µl/hr of either PBS (control) or 100 µM SSTN were implanted and the tumors allowed to grow for an additional 28 days. Scanning of the tumors at this point (measured as photons/second/cm2/steradian) shows an 11-fold reduction in tumor size by treatment with SSTN (not shown.) The five mice on the right received PBS and have visible, large tumors (circled). The mice on the left received SSTN and have smaller tumors. The pump is visible on all mice as a purple spot on their right flank.

FIGS. 16A-16B—Myeloma tumors from SSTN-treated mice. (FIG. 16A) Myeloma tumors from either PBS or SSTN treated mice were dissected and weighed after 28 days: control (238+/−92 g) and SSTN-treated (22+/−6 g) tumors again showing an 11-fold difference (P=0.02). (FIG. 16B) A PBS control and a SSTN-treated tumor were sectioned and stained with mouse-specific anti-CD34 to view in the ingrowth of host blood vessels to the human tumor. The control tumors had more numerous and much longer vessels (arrowheads) than the treated tumors. There was no positive staining using human-specific anti-CD34 (not shown), indicating that the vasculature in the tumors is due to host angiogenesis.

Figure 17:
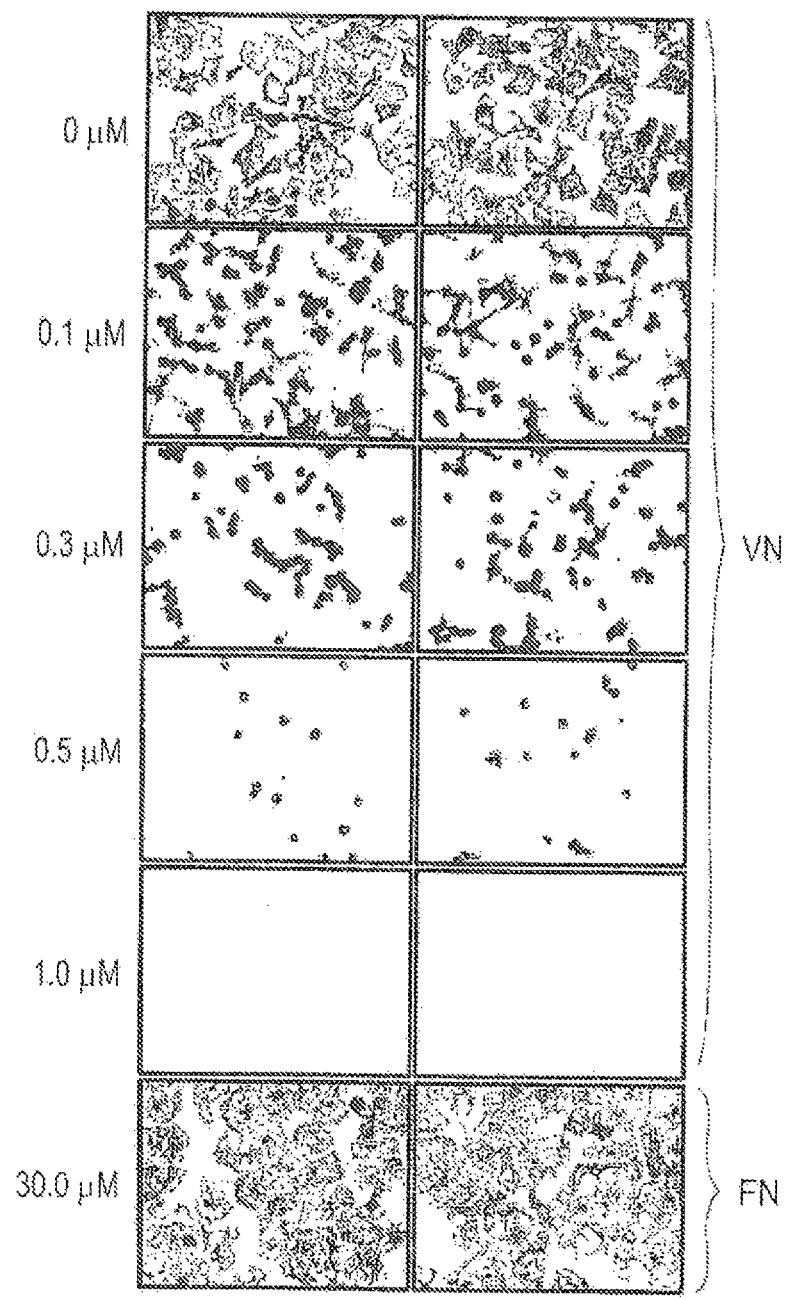

FIG. 17—Human SSTN peptides inhibit $\alpha_v\beta_3$—mediated cell attachment and spreading on vitronectin. MDA-MB-231 human mammary carcinoma cells were allowed to attach and spread on either vitronectin (VN) or fibronectin (FN) during a 2 hr assay in the presence of 0, 0.1, 0.3, 0.5, 1.0 or 30 µM SSTN peptide. The 30 µM concentration was used only for FN to demonstrate its lack of activity on this substratum. The two peptides tested are derived either from amino acids 88-121 (hSSTN 88-121) or 89-120 (hSSTN 89-120) of the human Sdc1 sequence. Adhesion to VN, but not FN, is mediated by the $\alpha_v\beta_3$ integrin on these cells and is disrupted by the human SSTN peptides.

DESCRIPTION OF ILLUSTRATIVE EMBODIMENTS

I. The Present Invention

The inventors previously established a link between Sdc-1 and the $\alpha_v\beta_3$ integrin (Beauvais and Rapraeger, 2003). Subsequently, they also showed that addition of recombinant mouse Sdc-1 (mS1) ectodomain (ED) or anti-Scd-1ED polyclonal antibodies (pAbs) block integrin activation and disrupt $\alpha_v\beta_3$-dependent spreading and migration of cancer cells, and that downregulation of human Sdc-1 (hS1) expression by small-interfering RNA (siRNA) disrupts cancer cell spreading and migration on VN, but not on FN. These data suggest that Sdc-1 and the $\alpha_v\beta_3$ integrin are functionally coupled via the Scd-1ED and that coupling is required for $\alpha_v\beta_3$ integrin activation and signaling.

In addition, the inventors demonstrated a syndecan link to $\alpha_v\beta_5$ integrin. The inventors showed that B82L fibroblast cells rely almost solely on the $\alpha_v\beta_5$ integrin for attachment and spreading on VN and this integrin activity depends on Sdc-1. Cells ligated by Sdc-1 antibody displayed hyperactivation of the $\alpha_v\beta_5$ integrin. In addition, expression studies showed that the expression of the extracellular domain of Sdc-1 at the cell surface is necessary for integrin activation. In keeping with this finding, competition with the recombinant ectodomain of Sdc-1 inactivated the integrin, as shown by the failure of cells to attach and spread to the $\alpha_v\beta_5$ integrin ligand VN.

The formation of new blood vessels, which occurs in development and disease, relies on inducing proliferation and migration of endothelial cells, and in controlling the survival or apoptosis of the cells to sculpt the architecture of the new vessels (vascular pruning). The αvβ3 and αvβ5 integrins have important roles in all three of these steps. Surprisingly, work with $\beta_3$, $\beta_5$, or double $\beta_3/\beta_5$ knockout mice shows that angiogenesis in mice lacking one or both of these integrins is not blocked, and may be increased (Reynolds et al., 2002). One explanation for these results is that the main role of the integrins during normal angiogenesis is to act as a "brake" and to prune unwanted new vessels by activating cell death (apoptosis). Inhibitors that inactivate the integrin and thus disrupt cell migration that relies on these integrins have the additional effect of enhancing the apoptotic signal emanating from the integrins, leading to endothelial cell death. This death mechanism is lacking in mice in which the integrin gene is disrupted, and this may account for the enhanced angiogenesis seen in such knockout mice.

A peptide representing the active site in the extracellular domain of Sdc1 (an inhibitory activity referred to as "synstatin") competitively disrupts this positive regulation and blocks biological processes in which these two integrins participate, including angiogenesis. There are a number of anti-angiogenic compounds that have been described and many are in clinical trials. Some are generated in vivo, often by proteolysis of native matrix components, giving rise to angiostatin (O'Reilly et al., 1994), endostatin (O'Reilly et al., 1997), canstatin (Kamphaus et al., 2000), arresten (Colorado et al., 2000) and tumstatin (Maeshima et al., 2000). Tumstatin is of interest as it is derived from the α3 chain of collagen IV and the active site within tumstatin targets the αvβ3 integrin. In light of the inventors' observations with regard to the activity of synstatin, the fact that Tumstatin inhibits the proliferation of endothelial cells and is a highly effective inhibitor in angiogenesis assays is not surprising.

II. $\alpha_v\beta_3$ and $\alpha_v\beta_5$ Integrins

The $\alpha_v\beta_3$ and $\alpha_v\beta_5$ are closely related integrins that are upregulated during disease processes. The $\alpha_v\beta_3$ integrin is a key regulator of adhesion and signaling in numerous biological processes, including tumor cell migration and metastasis, and angiogenesis. The activated form of this integrin participates in arrest of tumor cells in the blood stream (Pilch et al., 2002), enhancing their extravasation to target tissues, especially bone, where the activated integrin has further roles in tumor cell proliferation and survival (Brooks et al., 1994; Petitclerc et al., 1999; Eliceiri, 2001). In endothelial cells forming new blood vessels, the active integrin is linked not only to adhesion-dependent processes but also to signaling in response to FGF-2 (Eliceiri et al., 1998; Hood et al., 2003).

Although $\alpha_v\beta_3$ integrin expression in mammary epithelium is low, activated $\alpha_v\beta_3$ is expressed on most, if not all, successful mammary carcinoma metastases (Liapis et al., 1996; Felding-Habermann et al., 2001). The inventors have reported previously that $\alpha_v\beta_3$ integrin on MDA-MB-231 mammary carcinoma cells appears to be functionally linked to Sdc-1; the cells spread when adherent to an artificial substratum comprised solely of Sdc1-specific antibody, and although this spreading occurs in the absence of a $\alpha_v\beta_3$ ligand, the spreading requires activated $\alpha_v\beta_3$ integrin (Beauvais and Rapraeger, 2003). This finding suggests that even on a native ECM, anchorage of Sdc-1 to the matrix may serve as an important regulator of $\alpha_v\beta_3$ integrin activation and signaling.

Although classically defined as a vitronectin (VN) receptor, $\alpha_v\beta_3$ is promiscuous and binds many ECM components including fibronectin (FN), fibrinogen, von Willebrand Factor, proteolysed fragments of collagen (COL), laminin (LN), osteopontin, and others (van der Flier and Sonnenberg, 2001). Mechanisms leading to activation of this integrin are complex, including proteolytic cleavage (Ratnikov et al., 2002), conformational changes (affinity modulation), and clustering (avidity modulation; Carman and Springer, 2003). Activation is regulated by "inside-out" signals from the cell interior and is stabilized by ligand interactions that trigger "outside-in" signaling (Giancotti and Ruoslahti, 1999). Cell surface receptors known to modulate $\alpha_v\beta_3$ activity include CD87/uPAR and CD47/IAP, which associate with the $\beta_3$ integrin subunit via their extracellular domains (Lindberg et al., 1996; Xue et al., 1997) and may also regulate $\alpha_v\beta_3$ function indirectly via a pertussis toxin-sensitive G-protein signaling pathway (Gao et al., 1996; Degryse et al., 2001).

The $\alpha_v\beta_5$ integrin is a close relative of the $\alpha_v\beta_3$ integrin. The $\alpha_v\beta_5$ integrin is expressed on a variety of tissues and cell types, including endothelia, epithelia and fibroblasts (Felding-Habermann and Cheresh, 1993; Pasqualini et al., 1993). It is closely related to the $\alpha_v\beta_3$ integrin (56.1% identity and 83.5% homology between the two integrin $\beta$-subunits) but is distinguished from the $\alpha_v\beta_3$ by divergent sites near its ligand-binding domain and within the C-terminus of its cytoplasmic domain (McLean et al., 1990). It has a role in matrix adhesion to VN, FN, SPARC and bone sialoprotein (Plow et al., 2000) and is implicated in the invasion of gliomas and metastatic carcinoma cells (Brooks et al., 1997; Jones et al., 1997; Tonn et al., 1998), the latter especially to bone (De et al., 2003). A second major role is in endocytosis, including endocytosis of VN (Memmo and McKeown-Longo, 1998; Panetti et al., 1995), the engulfment of apoptotic cells by phagocytes (Albert et al., 2000), and participation in the internalization of shed outer rod segments in the retinal pigmented epithelium (Finnemann, 2003a; Finnemann, 2003b; Hall et al., 2003). A third major role is in growth factor-induced angiogenesis, where cooperative signaling by the $\alpha_v\beta_5$ integrin and growth factors regulates endothelial cell proliferation and survival. Angiogenesis promoted by VEGF and TGFα in human umbilical vein endothelial cells relies on co-signaling with the $\alpha_v\beta_5$ integrin, whereas FGF-2 and tumor necrosis factor-α collaborate with the $\alpha_v\beta_3$ integrin (Eliceiri and Cheresh, 1999; Friedlander et al., 1995).

III. Syndecans

A. The Syndecan Family

Cell surface adhesion receptors physically bind cells to their extracellular matrix (ECM) and couple such interactions to intracellular signaling mechanisms which influence gene expression, cell morphology, motility, growth, differentiation and survival (Roskelley et al., 1995; Miranti and Brugge, 2002). Many ECM ligands contain closely spaced proteoglycan- and integrin-binding domains, indicating that the molecular mechanisms by which cells recognize and interact with their extracellular milieu may involve the formation of signaling complexes containing both proteoglycans and integrins. Consequentially, these two types of receptors may act in concert to modulate cell adhesion and migration. While the role of integrins in cell adhesion and signaling is well established, the role of heparan sulfate proteoglycans (HSPGs) is not well characterized.

The vertebrate syndecans are a family of four transmembrane HSPGs. Endowed by their heparan sulfate (HS) chains, syndecans bind a variety of ECM ligands, including fibronectin (FN), laminin (LN), tenascin, thrombospondin (TSP), vitronectin (VN) and the fibrillar collagens (COL) (Bernfield et al., 1999). While the syndecan HS chains are essential for matrix binding, less is known about the role of syndecan core proteins in cell adhesion signaling, although the core protein can affect ligand binding interactions, as well as occupancy induced signaling (Rapraeger and Ott, 1998; Rapraeger, 2000).

The syndecans display a high degree of conservation within their core proteins both across species and across family members. Like the integrins, the syndecans lack intrinsic signaling activity. Their short cytoplasmic tails (ca. 30 aa) consist of three regions, two of which are conserved amongst the four syndecans (C1 and C2) and which flank an intervening variable (V) region. Proteins known to interact with these conserved domains are believed to link syndecan ligand binding interactions to the transduction of intracellular signals (Couchman et al., 2001). Each family member is uniquely defined by its ectodomains and the V-regions of its cytoplasmic tail. Divergence within these regions is believed to confer separate and distinct functions to each individual family member. Distinct roles for the V-regions of Sdc-2 and -4 in matrix assembly and focal adhesion formation respectively have been described (Klass et al., 2000; Woods and Couchman, 2001); however, specific functions for the syndecan ectodomains are almost wholly unknown with the noted exception of Sdc-1 and -4 which contain binding sites for as yet unidentified cell surface receptor(s) (McFall and Rapraeger, 1997; McFall and Rapraeger, 1998).

B. Syndecan Function in Cell Adhesion and Spreading

Current evidence suggests that the syndecan core proteins participate in adhesion-mediated signaling in collaboration with co-receptors at the cell surface. One example is Sdc-4 in focal adhesion and stress fiber formation, which requires both Sdc-4 and integrin engagement whereas neither is sufficient alone (Woods et al., 1986; Izzard et al., 1986; Streeter and Rees, 1987; Singer et al., 1987). The requirement for Sdc-4 ligation can be overcome by treatment with phorbol esters (Woods and Couchman, 1994) or lysophosphatidic acid (LPA) (Saoncella et al., 1999) implicating PKC and RhoA in Sdc-4 signaling. While the mechanism by which Sdc-4 contributes to RhoA activation is not clear, it is known that Sdc-4 interacts directly with PKCα as well as phosphatidyl inositol 4,5 bisphosphate (PIP2) via its cytoplasmic tail and these interactions potentiate PKCα activity (Oh et al., 1997a; Oh et al., 1997b; Oh et al., 1998; Baciu and Goetinck, 1995).

While the mechanism by which Sdc-1 signals is not clear, there is ample evidence implicating a signaling role for this receptor as well. Ectopic expression of Sdc-1 in Schwann cells enhances cell spreading and promotes the formation of focal adhesions (Hansen et al., 1994) and actin stress fibers (Carey et al., 1994a); similar morphological changes occur when Sdc-1 is co-clustered with antibodies (Carey et al., 1994b). This response requires the cytoplasmic domain, since clustering of a truncated core protein did not induce reorganization of the cytoskeleton. Expression of Sdc-1 in human ARH-77 leukemia cells or hepatocellular carcinoma cells inhibits invasion of cells into COL matrices (Liu et al., 1998; Ohtake et al., 1999). ARH-77 cells expressing a chimera comprised of the Sdc-1 ectodomain fused to the glycosyl-phosphatidyl inositol (GPI) tail of glypican-1 also fail to invade a COL matrix demonstrating that Sdc-1's anti-invasive activity resides in its extracellular domain. In similar studies, Raji human lymphoblastoid cells transfected with mouse Sdc-1 (Raji-S1) spread on TSP, FN and antibodies directed against the Sdc-1 ectodomain (Lebakken and Rapraeger, 1996). This spreading is unaffected by truncation of the cytoplasmic domain, indicating that the Sdc-1 core protein interacts with and cooperatively signals through an associated transmembrane signaling partner. Analogous features have also been observed for Sdc-2 (Granes et al., 1999) and Sdc-4 (Yamashita et al., 1999).

Potential syndecan signaling partners include cell surface integrins. Iba et al. (2000) demonstrated that mesenchymal cells when seeded on an HS-specific ligand, the cysteine rich domain of a disintegrin and metalloprotease, ADAM-12/Meltrin α (rADAM12-cys), will spread in a manner that requires cooperate signaling of both syndecans and $\beta_1$ integrins. These results imply that syndecan(s) can trigger signaling cascades required for cell spreading either by exposing a cryptic binding site for $\beta_1$ integrins, as has been proposed for FN (Khan et al., 1988), or by modulating the activation state of $\beta_1$ integrins. Interestingly, colon carcinoma cells attach but fail to spread on aADAM12-cys. However, exogenous stimulation of $\beta_1$ integrins with $Mn^{2+}$ or $\beta_1$ integrin function activating antibody, mAb 12G10, induced cell spreading, suggesting a mechanism whereby the syndecan activates $\beta_1$ integrins is blocked in transformed cells.

C. Angiogenesis

The formation of new blood vessels, called angiogenesis, which occurs in normal development as well as in disease states, relies on inducing proliferation and migration of endothelial cells, and in controlling the survival or apoptosis of the cells to control the architecture of the new vessels (vascular pruning). The αvβ3 integrin has important roles in all three of these steps.

FGF and VEGF, two growth factors that are often released by tumors, cause endothelial cells to undergo angiogenesis. Blood vessels in the vicinity of the tumor respond to VEGF by becoming leaky (thus the alternate name "vascular permeability factor") allowing fibronectin, vitronectin and fibrinogen in the blood to infiltrate the surrounding matrix. These matrix ligands are critical adhesion and activation ligands for the αvβ3 and αvβ5 integrins, which have roles in the chemotactic migration of the endothelial cells and in the survival of the cells during vessel pruning. A second response to the growth factors, particularly FGF, is the activation of a neovessel development program that relies on Hox master genes (Boudreau et al., 1997; Myers et al., 2000; 2002). HoxD3 is initially expressed and controls a family of genes that are necessary for the initial migration process, including upregulation of the αvβ3 integrin, MMPs and uPAR (Boudreau et al., 1997). Expression of HoxD3 is followed by HoxB3 that regulates the morphogenesis leading to formation of small vessels (Myers et al., 2000), and finally by the HoxD10 gene, which restores the mature phenotype of the cells (Myers et al., 2002); it is HoxD10 that is expressed in resting, stable blood vessels in vivo.

The $\alpha v \beta_3$ integrin is important not only during endothelial cell migration, but is an important player in the survival of the endothelial cells. Although endothelial cells in mature vessels are not readily susceptible to apoptosis, angiogenic cells that are induced by growth factors rely upon the continued presence of these factors for survival. This is shown experimentally by inducing angiogenesis with VEGF and causing apoptosis by its withdrawal, or in vivo when the developing ovarian follicle induces angiogenesis by release of VEGF and the newly formed bloods vessels regress upon ovulation as the source of VEGF is lost. Endothelial cells responding to VEGF have been shown to be dependent on signaling from the $\alpha v \beta_5$ integrin in order to block this apoptotic process (Brooks et al., 1994; Friedlander et al., 1995). Thus, inhibiting the integrin using anti-integrin antibodies will induce apoptosis of the endothelial cells responding to VEGF. Similarly, endothelial cells responding to fibroblast growth factor (FGF) are susceptible to apoptosis unless there is coordinate signaling from the αvβ5 integrin.

There are a number of anti-angiogenic compounds that have been described and many are in clinical trials. Some are generated in vivo, potentially the proteolysis of native matrix components, giving rise to angiostatin (O'Reilly et al., 1994), endostatin (O'Reilly et al., 1997), canstatin (Kamphaus et al., 2000), arresten (Colorado et al., 2000) and tumstatin (Maeshima et al., 2000). Tumstatin is of interest as it is derived from the α3 chain of Collagen IV and the active site within tumstatin is a peptide binding site that targets the $\alpha v \beta_3$ integrin, although it appears distinct from the RDG binding site of the integrin. Tumstatin inhibits the proliferation of endothelial cells and is a highly effective inhibitor in angiogenesis assays. As this invention describes the regulation of the $\alpha v \beta_3$ integrin by Sdc-1 in mammary carcinoma cells and in endothelial cells, and this dependence can be blocked by soluble S1ED, it is hypothesized that this inhibitor would be an effective inhibitor of angiogenesis as well. Perhaps more intriguing is its activity only against the endothelial cells that express Sdc-1. Although there is not much information available, the information to date indicates that resting endothelial cells lining adult blood vessels do not express Sdc-1. In contrast, expression of Sdc-1 is turned on when the cells are activated to undergo angiogenesis, such as occurs normally in wounding, or occurs in abnormal conditions such as diabetic retinopathy, restenosis following blood catheter injury to blood vessels, or tumor angiogenesis. Thus, it is intriguing that targeting the Sdc-1 regulation of the αvβ3 integrin can provide not only an additional opportunity for drug discovery, but the drug may be most efficacious during angiogenesis itself.

There has not been a concerted examination of Sdc-1 expression in vascular endothelium. Most reports suggest that it is expressed poorly or not at all on resting, mature vascular endothelium that lines blood vessels. However, there are reports that suggest it is expressed on activated endothelial cells participating in angiogenesis in the wounded skin (Elenius et al., 1991; Gallo et al., 1996). Sdc-1 is not expressed in endothelial cells lining the rabbit aorta, but expression is upregulated following balloon catheter injury and persists for up to 12 weeks following injury. There is a report that Sdc-1 is upregulated in a subset of vessels during tumor angiogenesis (Gotte et al., 2002). These studies strongly suggest that Sdc-1 becomes expressed on activated cells responding to injury or growth factors. Cultured cells, such as human aortic and human umbilical vein endothelial cells show expression at both the protein and mRNA level, although expression in human umbilical vein endothelial cells is low (Mertens et al., 1992). However, the expression patterns described may be dependent on the growth factors and supplements, such as brain extract, added to the culture medium.

D. Syndecan-1

Syndecan-1 is highly expressed at the basolateral surface of epithelial cells where it is thought to interact with the actin cytoskeleton and to modulate cell adhesion and growth factor signaling (Bernfield et al., 1999; Rapraeger et al., 1986; Kim et al., 1994; Sanderson and Bernfield, 1988). In experimental studies of malignant transformation, Sdc-1 expression is associated with the maintenance of epithelial morphology, anchorage-dependent growth and inhibition of invasiveness. Alterations in syndecan expression during development (Sun et al., 1998) and in transformed epithelial (Inki and Jalkanen, 1996; Bayer-Garner et al., 2001) are associated with an epithelial-mesenchymal transformation with attendant alterations in cell morphology, motility, growth and differentiation. Transfection of epithelial cells with anti-sense mRNA for Sdc-1 or downregulation of Sdc-1 expression by androgen-induced transformation results in an epithelial to mesenchymal transformation and increased invasion (Leppa et al., 1992; Kato et al., 1995; Leppa et al., 1991). The loss of E-cadherin under these circumstances has long suggested a coordinate regulation of Sdc-1 and E-cadherin expression (Sun et al., 1998; Leppa et al., 1996). These studies, as well as others, indicate that there appears to be a threshold requirement for syndecan expression to elicit its biological activity. Syndecan-1 is downregulated in a number of epithelial cancers and in pre-malignant lesions of the oral mucosa (Soukka et al., 2000) and uterine cervix (Inki et al., 1994; Rintala et al., 1999; Nakanishi et al., 1999), and its loss may be an early genetic event contributing to tumor progression (Sanderson, 2001; Numa et al., 2002; Hirabayashi et al., 1998). Loss of Sdc-1 correlates with a reduced survival in squamous cell carcinoma of the head, neck and lung (Anttonen et al., 1999; Inki et al., 1994; Nakaerts et al., 1997), laryngeal cancer (Pulkkinen et al., 1997; Klatka, 2002), malignant mesothelioma (Kumar-Singh et al., 1998) and multiple myeloma (Sanderson and Borset, 2002) and a high metastatic potential in hepatocellular and colorectal carcinomas (Matsumoto et al., 1997; Fujiya et al., 2001; Levy et al., 1997; Levy et al., 1996). Downregulation of Sdc-2 and -4 expression has also been observed in certain human carcinomas (Nakaerts et al., 1997; Park et al., 2002; Mundhenke et al., 2002; Crescimanno et al., 1999), but the functional consequences of these alterations in expression are less clear.

In contrast to the general notion that the syndecan may be an inhibitor of carcinogenesis, Sdc-1 also demonstrates tumor promoter function. Syndecan-1 supplements Wnt-1 induced tumorigenesis of the mouse mammary gland (Alexander et al., 2000) and promotes the formation of metastases in mouse lung squamous carcinoma cells (Hirabayashi et al., 1998). Enhanced Sdc-1 expression has also been observed in pancreatic (Conejo et al., 2000), gastric (Wiksten et al., 2001) and breast (Burbach et al., 2003; Stanley et al., 1999; Barbareschi et al., 2003) carcinomas and this overexpression correlates with increased tumor aggressiveness and poor clinical prognosis. This duality in the role of Sdc-1 in tumorigenesis may reflect tissue and/or tumor stage-specific function, or reflect the multiple functions of this PG.

Sanderson was the first to demonstrate a role for Sdc-1 in tumor cell migration by examining the invasion of myeloma cells into collagen gels (Liu et al., 1998). Ectopic expression of Sdc-1 in syndecan-deficient myeloma cells had the striking effect of curtailing invasion, whereas the expression of other cell surface heparan sulfate PGs (e.g., glypican) was without effect. Using chimeras derived from these two proteins, Sanderson showed that the activity of the syndecan is preserved when its ectodomain alone is expressed as a glycosyl-phosphatidylinositol (GPI)-linked protein at the cell surface. Although clearly responsible for binding the collagen matrix via its attached heparan sulfate chains, the anti-invasive activity of the syndecan requires yet an additional interaction that traces to a site in the extracellular domain of the core protein itself. The mechanism by which the ectodomain site influences the invasion of the myeloma cells is unknown, but its interaction with other cell surface receptors in a "co-receptor" role is one possibility. More recently, ectopic expression of Sdc-1 has also been shown to curtail the invasion of hepatocellular carcinoma cells into a collagen matrix (Ohtake et al., 1999).

E. Proteins and Peptides

Syndecan-1 peptides and polypeptides of the present invention will generally comprise molecules of 5 to about 240 residues in length, and may have the sequence of SEQ ID NO:1 or SEQ ID NO:4 or SEQ ID NO:8 or SEQ ID NO:9 or SEQ ID NO:10 or SEQ ID NO:13 or SEQ ID NO:21 or SEQ ID NO:23 or SEQ ID NO:28. A particular length may be 234 residues, 34 residues, 32 residues, less than 30 residues, less than 25 residues, less than 20 residues, less than 15 residues, or less than 14 residues, including 5, 6, 7, 8, 9, 10, 11, 12, or 13 residues. In other embodiments, the peptides or proteins may be from SEQ ID NOs:2, 4, 8, 9, 13, 21, 23, or 28 and may thus comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 49, 50, 55, 60, 65, 70, 75, 80, 85, 90, 95, 100, 110, 120, 130, 140, 150, 160, 170, 180, 190, 200, 210, 220, 230, or 240 consecutive residues of that sequence. Alternatively, the peptides may have 90%, 95%, or more identity with the SEQ ID NOs identified herein. It is further contemplated that any embodiment involving a mouse sequence discussed herein may be implemented with the corresponding human sequence. Such human peptides and nucleic acids encoding such peptides are specifically contemplated as part of the invention.

The peptides or proteins may be generated synthetically or by recombinant techniques, and are purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

Accordingly, sequences that have between about 70% and about 80%, between about 81% and about 90%, between about 91% and 95%, or about 96, about 97%, 98% or about 99% of amino acids that are identical or functionally equivalent to the amino acids of SEQ ID NOs:2, 4, 8, 9 or 10, will be sequences that are "essentially as set forth in SEQ ID NOs:2, 4, 8, 9 or 10." Peptides and polypeptides of the invention may be as essentially as set forth in SEQ ID NOS:2, 4, 8, 9 or 10.

i. Substitutional Variants

It also is contemplated in the present invention that variants or analogs of syndecan-1 peptides or proteins may also inhibit tumor growth. Polypeptide sequence variants of syndecan-1, primarily making conservative amino acid substitutions to SEQ ID NOs:2, 4, 8, 9 or 10, may provide improved compositions. Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a peptide or protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a peptide that defines that peptide's biological functional activity, certain amino acid substitutions can be made in a protein sequence, and its underlying DNA coding sequence, and nevertheless obtain a peptide with like properties. It is thus contemplated by the inventors that various changes may be made in syndecan-1 amino acid sequences and in the DNA sequences coding the peptide without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant peptide, which in turn defines the interaction of the peptide with other molecules.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of syndecan-1, but with altered and even improved characteristics.

ii. Altered Amino Acids

The present invention may employ peptides that comprise modified, non-natural and/or unusual amino acids. A table of exemplary, but not limiting, modified, non-natural and/or unusual amino acids is provided herein below. Chemical synthesis may be employed to incorporate such amino acids into the peptides of interest.

TABLE 1

Modified, Non-Natural and Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | Ahyl | allo-Hydroxylysine |
|  |  | 3Hyp | 3-Hydroxyproline |
| Abu | 2-Aminobutyric acid | 4Hyp | 4-Hydroxyproline |
| 4Abu | 4-Aminobutyric acid, piperidinic acid | Ide | Isodesmosine |
|  |  | Aile | allo-Isoleucine |
| Acp | 6-Aminocaproic acid | MeGly | N-Methylglycine, sarcosine |
| Ahe | 2-Aminoheptanoic acid |  |  |
| Aib | 2-Aminoisobutyric acid | MeIle | N-Methylisoleucine |
| BAib | 3-Aminoisobutyric acid | MeLys | 6-N-Methyllysine |
| Apm | 2-Aminopimelic acid | MeVal | N-Methylvaline |
| Dbu | 2,4-Diaminobutyric acid | Nva | Norvaline |
| Des | Desmosine | Nle | Norleucine |
| Dpm | 2,2'-Diaminopimelic acid | Orn | Ornithine |
| Dpr | 2,3-Diaminopropionic acid |  |  |
| EtGly | N-Ethylglycine |  |  | iii. Mimetics

In addition to the variants discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and high permissive for mutation. This motif is composed of a beta sheet and an alpha helix bridged in the interior core by three disulfides. Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. These structures, which render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

iv. D Amino Acids

In another form, the present invention contemplates use of variants that comprise various portions of an syndecan-1 peptide or protein in reverse order of SEQ ID NOs:2, 4, 8, 9 or 10, using D amino acids, stereoisomers of natural amino acids which are in the L-form.

v. Peptide Synthesis

Syndecan-1 and related peptides may be generated synthetically for use in various embodiments of the present invention. Because of their relatively small size, the peptides of the invention can be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); Barany and Merrifield (1979), each incorporated herein by reference. Short peptide sequences, or libraries of overlapping peptides, usually from about 5 up to about 34 to 40 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

It may be desirable to purify syndecan-1 variants, peptide-mimics or analogs thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

IV. Anti-Idiotypic Antibodies

The present invention also provide antibodies that mimic the syndecan-1 peptides and proteins described herein. These antibodies are created by first preparing an antibody against a syndecan-1 peptide or protein and then preparing a second antibody, called an anti-idiotypic antibody, against the idiotype of the first antibody. As a mirror image of a mirror image, the binding site of anti-idiotype would be expected to be an analog of the original antigen. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibodies and antibody-based constructs and fragments are well known in the art (see, e.g., Harlow et al., 1988; and U.S. Pat. No. 4,196,265 each incorporated herein by reference).

V. Nucleic Acid Segments Encoding Syndecan Peptides and Proteins

The present invention concerns nucleic acid segments, isolatable from cells, that are free from total genomic DNA and that are capable of expressing all or part of a protein or polypeptide such as syndecan-1 or the syndecan-1 peptide or protein of SEQ ID NOs:2, 4, 8, 9, 10, 21, 23, or 28. The nucleic acid may encode a peptide or polypeptide containing all or part of the syndecan-1 amino acid sequence.

As used herein, the term "nucleic acid segment" refers to a DNA molecule that has been isolated free of total genomic DNA of a particular species. Therefore, a nucleic acid segment encoding a syndecan-1 refers to a nucleic acid segment that contains wild-type, polymorphic, or mutant polypeptide-coding sequences yet is isolated away from, or purified free from, total mammalian or human genomic DNA. Included within the term "nucleic acid segment" are a polypeptide(s), nucleic acid segments smaller than a polypeptide, and recombinant vectors, including, for example, plasmids, cosmids, phage, viruses, and the like.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

A nucleic acid segment encoding all or part of a native or modified polypeptide may contain a contiguous nucleic acid sequence encoding all or a portion of such a polypeptide of the following lengths: about 10, about 20, about 30, about 40, about 50, about 60, about 70, about 80, about 90, or about 100, about 110, about 120, about 130, about 140, about 150, about 160, about 170, about 180, about 190, about 200, about 210, about 220, about 230, about 240, about 250 or about 260 nucleotides, nucleosides, or base pairs. Specifically contemplated are a segment encoding SEQ ID NO:2, a segment encoding the 34 residue peptide of SEQ ID NO:4, a segment encoding residues 18-251 residues of SEQ ID NO:2 (SEQ ID NO:8), a segment encoding residues 18-310 of SEQ ID NO:2 (SED ID NO:9) or residues 82-130 of SEQ ID NO:2 (SEQ ID NO:10). Additionally, nucleic acids encoding a peptide consisting of or comprising the amino acid sequence of SEQ ID NOs:1, 21, 23, or 28.

The nucleic acid segments used in the present invention, regardless of the length of the coding sequence itself, may be combined with other nucleic acid sequences, such as promoters, enhancers polyadenylation signals, origin of replication, and a selectable marker gene, as well as other coding segments, and the like (all as are known to those of ordinary skill in the art), such that their overall length may vary considerably.

The term oligonucleotide refers to at least one molecule of between about 3 and about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

It is contemplated that the nucleic acid constructs of the present invention may encode full-length polypeptide from any source or encode a truncated version of the polypeptide, for example a truncated syndecan-1 polypeptide, such that the transcript of the coding region represents the truncated version. The truncated transcript may then be translated into a truncated protein. Alternatively, a nucleic acid sequence may encode a full-length polypeptide sequence with additional heterologous coding sequences, for example to allow for purification of the polypeptide, transport, secretion, post-translational modification, or for therapeutic benefits such as targeting or efficacy.

It is contemplated that the nucleic acid constructs of the present invention may regulate gene expression of an immunogenic polypeptide. A nucleic acid segment may regulate the expression of a full-length polypeptide sequence with additional heterologous coding sequences, for example to allow for therapeutic benefits such as targeting or efficacy.

In a non-limiting example, one or more nucleic acid constructs may be prepared that include a contiguous stretch of nucleotides identical to or complementary to a particular gene, such as the human syndecan-1 gene (SEQ ID NO:1), or a fragment thereof (SEQ ID NO:3 or that encoding SEQ ID NOs:8 or 9 or 10). Such a nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

In certain other embodiments, the invention concerns isolated nucleic acid segments and recombinant vectors that include within their sequence a contiguous nucleic acid sequence from that shown in SEQ ID NO:1, 3 or encoding SEQ ID NOs:8 or 9 or 10 or 21 or 23 or 28. This definition is used in the same sense as described above and means that the nucleic acid sequence substantially corresponds to a contiguous portion of that shown in SEQ ID NO:1 or 3 or encoding SEQ ID NOs:8 or 9 or 10 or 21 or 23 or 28 and has relatively few codons that are not identical, or functionally equivalent, to the codons of SEQ ID NO:1, 3 or encoding SEQ ID NOs:8, 9, 10, 21, 23, or 28. The term "functionally equivalent codon" is used herein to refer to codons that encode the same amino acid, such as the six codons for arginine or serine, and also refers to codons that encode biologically equivalent amino acids, as is known to those of skill in the art.

It also will be understood that this invention is not limited to the particular nucleic acid sequence of SEQ ID NO:1 and the amino acid sequence of SEQ ID NO:2. Recombinant vectors and isolated DNA segments may therefore variously include the syndecan-1-coding regions themselves, coding regions bearing selected alterations or modifications in the basic coding region, or they may encode larger polypeptides that nevertheless include syndecan-1-coding regions or may encode biologically functional equivalent proteins or peptides that have variant amino acids sequences.

The nucleic acid segments of the present invention encompass biologically functional equivalent syndecan-1 proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein.

If desired, one also may prepare fusion proteins and peptides, e.g., where the syndecan-1-coding regions are aligned within the same expression unit with other proteins or peptides having desired functions, such as for purification or immunodetection purposes (e.g., proteins that may be purified by affinity chromatography and enzyme label coding regions, respectively).

Encompassed by certain embodiments of the present invention are nucleic acid segments encoding relatively small peptides, such as, for example, peptides of from about 5 to about 40 amino acids in length, and more preferably, of from about 10 to about 34 amino acids in length; and also larger polypeptides up to and including proteins corresponding to the full-length sequence set forth in SEQ ID NO:2, the peptide of SEQ ID NO:4, the polypeptide of SEQ ID NOs:8 or 9, or the peptide of SEQ ID NOs:10, 21, 22, 23, or 28, or to specific nucleic acid fragments of SEQ ID NO:1, such as SEQ ID NO:3 and those encoding SEQ ID NOs:8 or 9 or 10 or 21, 23, or 28.

A. Promoters

The present invention may also involve expression of sdc-1 or related peptide from a sdc-1-encoding nucleic acid. This requires the presence of a promoter operably linked to the sdc-1-coding region. A promoter generally comprises a nucleic acid sequence that functions to position the start site for RNA synthesis. A promoter may or may not be used in conjunction with an enhancer, which refers to a cis-acting regulatory sequence involved in the transcriptional activation of a nucleic acid sequence. In the present invention, a nucleic acid encoding a sdc-1 comprises a promoter such as a tissue specific promoter, or a constitutive promoter, or an inducible promoter.

A promoter in the context of the present invention may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter or enhancer, which refers to a promoter or enhancer that is not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Those of skill in the art of molecular biology generally know the use of promoters, enhancers, and cell type combinations for protein expression, for example, see Sambrook et al. (2000), incorporated herein by reference.

The present invention also contemplates the use of tissue specific promoters and inducible promoters. Other promoters that may be employed with the present invention are constitutive and inducible promoters as are well known to those of skill in the art. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

B. Origins of Replication/Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention. Polyadenylation signals include the SV40 polyadenylation signal and the bovine growth hormone polyadenylation signal, known to function well in various target cells. Polyadenylation may increase the stability of the transcript or may facilitate cytoplasmic transport.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

C. Delivery of Nucleic Acids

Two broad approaches have been used to employ vectors to deliver nucleic acids to cells, namely viral vectors and non-viral vectors. As by methods described herein and as is known to the skilled artisan, expression vectors may be constructed to deliver nucleic acids segments encoding a syndecan-1 of the present invention to a organelle, cell, tissue, or a subject. Such vectors comprising a syndecan-1 may be used in a variety of manner consistent with the invention, including in screening assay and genetic immunization protocols.

A vector in the context of the present invention refers to a carrier nucleic acid molecule into which a nucleic acid sequence of the present invention may be inserted for introduction into a cell and thereby replicated. A nucleic acid sequence can be exogenous, which means that it is foreign to the cell into which the vector is being introduced; or that the sequence is homologous to a sequence in the cell but positioned within the host cell nucleic acid in which the sequence is ordinarily not found. Vectors include plasmids; cosmids; viruses such as bacteriophage, animal viruses, and plant viruses; and artificial chromosomes (e.g., YACs); and synthetic vectors. One of ordinary skill in the art would be well equipped to construct any number of vectors through standard recombinant techniques as described in Maniatis et al., 1990 and Ausubel et al., 1994, incorporated herein by reference.

Viral vectors may be derived from viruses known to those of skill in the art, for example, bacteriophage, animal and plant virus, including but not limited to, adenovirus, vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) retrovirus and herpesvirus and offer several features for use in gene transfer into various mammalian cells (Friedmann, 1989; Ridgeway, 1988; Baichwal and Sugden, 1986; Coupar et al., 1988; Horwich et al., 1990).

One of skill in the art would be well equipped to construct a vector through standard recombinant techniques as described in Sambrook et al. (2001), Maniatis et al. (1990) and Ausubel et al. (1994), incorporated herein by reference. The present invention may also employ non-viral vectors.

An expression vector refers to any type of genetic construct comprising a nucleic acid coding for a RNA capable of being transcribed. In the context of the present specification, expression vectors will typically comprise a nucleic acid segment encoding a syndecan-1 as described herein. In some cases, RNA molecules are then translated into a protein, polypeptide, or peptide. In other cases, these sequences are not translated, as in the case of antisense molecules or ribozymes production. Expression vectors can contain a variety of control sequences, which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well, and are described herein Non-viral vectors, such as plasmids and cosmids, require suitable method for delivery into cells. Such methods include, but are not limited to direct delivery of DNA by: injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), microinjection (Harland and Weintraub, 1985; U.S. Pat. No. 5,789,215, incorporated herein by reference); electroporation (U.S. Pat. No. 5,384,253, incorporated herein by reference; Tur-Kaspa et al., 1986; Potter et al., 1984); calcium phosphate precipitation (Graham and Van Der Eb, 1973; Chen and Okayama, 1987; Rippe et al., 1990); using DEAE-dextran followed by polyethylene glycol (Gopal, 1985); direct sonic loading (Fechheimer et al., 1987); by liposome-mediated transfection (Nicolau and Sene, 1982; Fraley et al., 1979; Nicolau et al., 1987; Wong et al., 1980; Kaneda et al., 1989; Kato et al., 1991); receptor-mediated transfection (Wu and Wu, 1987; Wu and Wu, 1988); microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); agitation with silicon carbide fibers (Kaeppler et al., 1990; U.S. Pat. Nos. 5,302,523 and 5,464,765, each incorporated herein by reference); desiccation/inhibition-mediated DNA uptake (Potrykus et al., 1985), and any combination of such methods. Through the application of techniques such as these, organelle(s), cell(s), tissue(s) or organism(s) may be stably or transiently transformed. In certain embodiments, acceleration methods are preferred and include, for example, microprojectile bombardment or inhalation methods.

Also in context of the present invention, topical delivery of a nucleic acid segment encoding a syndecan-1 to the skin may further comprise vesicles such as liposomes, niosomes and transferosomes thereby enhancing topical and transdermal delivery. Cationic lipids may also be used to deliver negatively charged nucleic acids. Sonophoresis or phonophoresis which involves the use of ultrasound to deliver the nucleic acid of interest, may also be employed for transdermal delivery. Ionotophoresis which consists of applying a low electric field for a period of time to the skin may also be applied in delivering the nucleic acid of interest to the skin.

VI. Pharmaceutical Formulations, Delivery, and Cancer Treatment Regimens

In particular embodiments of the present invention, a method of treatment for cancer by the delivery of a Sdc-1 peptide or polypeptide (as described elsewhere in this document) is contemplated. Cancers contemplated by the present invention include, but are not limited to, breast cancer, lung cancer, head and neck cancer, bladder cancer, bone cancer, bone marrow cancer, brain cancer, colon cancer, esophageal cancer, gastrointestinal cancer, gum cancer, kidney cancer, liver cancer, nasopharynx cancer, ovarian cancer, prostate cancer, skin cancer, stomach cancer, testis cancer, tongue cancer, or uterine cancer. In particular embodiments, carcinomas, myelomas, melanomas or gliomas may be treated.

A variety of other non-cancer angiogenic diseases may also be treated with the Sdc-1 peptides or proteins of the present invention. These include angiogenesis leading to abonormalities of the vasculature (atherosclerosis and hemangiomas), of the eye (diabetic retinopathy and retinopathy of prematurity), the skin (pyogenic granulomas, psoriasis, warts, scar keloids, allergic edema, ulcers), the uterus and ovary (dysfunctional uterine bleeding, follicular cysts, endometriosis, pre-eclampsia) adipose tissue (obesity), bones and joints (Rheumatoid arthritis, osteophyte formation), and AIDS-related pathologies resulting from TAT protein of the human immunodeficiency virus (HIV) activating the avb3 integrin on endothelial cells (Carmeliet and Jain, 2000; Urbinati et al., 2005).

A. Administration

To inhibit angiogeneis in, e.g., cancer, one would generally contact a cell or tissue that has or can promote or undergo angiogenesis, with a Sdc-1 peptide or protein or an expression construct encoding a Sdc-1 peptide or protein. The preferred method for the delivery of a peptide or an expression construct is via injection. Administration may be parenteral, intradermal, intramuscular, or intratumoral administration. Other administration routes include lavage, continuous perfusion, topical and oral administration and formulation. See U.S. Pat. Nos. 5,543,158; 5,641,515; 5,399,363 (each specifically incorporated herein by reference in its entirety). Injection of nucleic acid constructs of the present invention may be delivered by syringe or any other method used for injection of a solution, as long as the expression construct can pass through the particular gauge of needle required for injection. A needleless injection system (U.S. Pat. No. 5,846,233); or a syringe system for use in gene therapy (U.S. Pat. No. 5,846,225), all as incorporated herein by reference, may be employed in the present invention.

B. Compositions and Formulations

Pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. Composition(s) of absorption delay agents (aluminum monostearate and gelatin) may also be used. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

For parenteral administration in an aqueous solution, for example, the solution should be suitably buffered if necessary and the liquid diluent first rendered isotonic with sufficient saline or glucose (see for example, "Remington's Pharmaceutical Sciences" 15th Edition, pages 1035-1038 and 1570-1580). These particular aqueous solutions are especially suitable for subcutaneous, intramuscular, and intratumoral administration. In this connection, sterile aqueous media that may be employed will be known to those of skill in the art in light of the present disclosure. Variation in dosage will necessarily occur depending on the condition of the subject being treated; the severity of the condition, and will be determined by the person administering the dose. For human administration, preparations should meet sterility, pyrogenicity, general safety and purity standards as required by FDA Office of Biologics standards.

The compositions of the present invention may be formulated in a neutral or salt form. Pharmaceutically-acceptable salts, include the acid addition salts (formed with the free amino groups of the protein) and which are formed with inorganic acids; or salts (formed with the free carboxyl groups) derived from inorganic bases as is known to those of ordinary skill in the art.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art.

C. Combination Treatments

In the context of the present invention, it is contemplated that Sdc-1 peptides, proteins or analogs thereof may be used in combination with an additional therapeutic agent to more effectively treat a cancer or other angiogenic diseases.

Additional therapeutic agents contemplated for use in combination with Sdc-1 peptides, proteins or analogs thereof include, in the case of cancers, traditional anticancer therapies. Anticancer agents may include but are not limited to, radiotherapy, chemotherapy, gene therapy, hormonal therapy, surgery or immunotherapy that targets cancer/tumor cells.

To kill cells, induce cell-cycle arrest, inhibit migration, inhibit metastasis, inhibit survival, inhibit proliferation, or otherwise reverse or reduce the malignant phenotype of cancer cells, using the methods and compositions of the present invention, one would generally contact a cell with sdc-1 peptides, proteins or an analog thereof in combination with an additional therapeutic agent. These compositions would be provided in a combined amount effective to inhibit cell growth and/or induce apoptosis in the cell.

For other angiogenic diseases, the combination therapy may include administration of a second anti-angiogenic therapy. This process may involve contacting the cells with Sdc-1 peptides, proteins or analogs thereof in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes the Sdc-1 peptides, proteins or derivatives thereof and the other includes the additional agent.

Alternatively, treatment with Sdc-1 peptides, proteins or analogs thereof may precede or follow the additional agent treatment by intervals ranging from minutes to weeks. In embodiments where the additional agent is applied separately to the cell, one would generally ensure that a significant period of time did not expire between the time of each delivery, such that the agent would still be able to exert an advantageously combined effect on the cell. In such instances, it is contemplated that one would contact the cell with both modalities within about 12-24 hr of each other and, more preferably, within about 6-12 hr of each other, with a delay time of only about 12 hr being most preferred. Thus, therapeutic levels of the drugs will be maintained. In some situations, it may be desirable to extend the time period for treatment significantly (for example, to reduce toxicity). Thus, several days (2, 3, 4, 5, 6 or 7) to several weeks (1, 2, 3, 4, 5, 6, 7 or 8) may lapse between the respective administrations.

It also is conceivable that more than one administration of either syndecan-1 peptides or analogs thereof in combination with an additional anticancer agent will be desired. Various combinations may be employed, where Sdc-1 peptide, protein or an analog thereof is "A" and the additional therapeutic agent is "B", as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Cells.

Human dermal microvascular endothelial cells (HMEC-1) and human aortic endothelial cells (HAEC) were grown in endothelial cell growth medium supplemented with 10% FBS serum. B82L mouse fibroblasts and human mammary carcinoma MDA-MB-231 cells were cultured in Dulbecco's Modified Eagle's medium supplemented with 10% FBS (Beauvais and Rapraeger, 2003; Beauvais et al., 2004; McQuade et al., 2006).

Recombinant mScd-1ED and Synstatin$_{82\text{-}130}$ Inhibitors.

A GST fusion protein consisting of the mScd-1ED (amino acids 18-251) was used as a competitor in cell adhesion studies (Beauvais and Rapraeger, 2003; McFall and Rapraeger, 1998). The protein was expressed in bacteria and purified on a glutathione affinity column as described in previous publications (Beauvais and Rapraeger, 2003; McFall and Rapraeger, 1998). Synstatin$_{82-130}$ peptide represents amino acids 82-130 of mouse Sdc-1. The peptide was synthesized and purified to 75% purity by GenScript Corporation (Piscataway, N.J.).

Cell Spreading Assays.

Cell adhesion and spreading assays were performed with modification to the previous procedures (Lebakken and Rapraeger, 1996. Briefly, human plasma vitronectin or fibronectin at 10-30 μg/ml were applied to nitrocellulose-coated ten well slides (Erie Scientific) and incubated for 1-2 h at 37° C. Slides were blocked with 1.0% heat-denatured bovine serum albumin for a minimum of 30 min at 37° C. Cells were detached from the substratum using 5 mM EDTA in Tris-buffered saline and resuspended in HEPES-buffered culture medium containing 0.1% heat-denatured BSA. Cells were plated at a density of 15,000 cells per well and allowed to attach and spread for 2 h prior to fixation in 4% paraformaldehyde in CMF-PBS. For fluorescence microscopy, fixed cells were permeabilized in 0.2% Triton X-100, labeled with rhodamine-conjugated phalloidin and analyzed using fluorescence microscopy. For testing inhibition by recombinant mScd-1ED and synstatin$_{82-130}$, cells were pre-incubated 10 min before plating in the presence of the inhibitor. In addition, dependence on the $\alpha v \beta_3$ and $\alpha v \beta_5$ integrins for adhesion and spreading on VN was demonstrated using blocking antibodies specific for these integrins. Monoclonal Ab13, which blocks all $\beta_1$-containing integrins, was used to show that cell attachment and spreading was not dependent on $\alpha v \beta_1$ integrin. LM609 was used as a specific block to $\alpha v \beta_3$ and P1F6 was used as a specific blocker of $\alpha v \beta_5$.

siRNA Design and Transfection.

Human specific siRNA against Sdc-1 was transfected into HAECs at a range of concentrations up to 200 nM. At 4 h after transfection, each well was supplemented with 3 mL of complete growth medium; at 24 h post-transfection the cells were lifted in trypsin and expanded in 100 mm tissue-culture plates. Cohorts were detached with EDTA 24 hr later, resuspended in 100 μL HEPES-buffered DME supplemented with 10% FBS and subjected to FACS analysis using mAb B-B4 specific for human Sdc-1 and an Alexa-488 conjugated anti-mouse secondary antibody. Cells were analyzed at the University of Wisconsin Comprehensive Cancer Center Flow Cytometry Facility using a FACSCalibur benchtop cytometer (BDBiosciences). Cell scatter and propidium iodide (Sigma, 1 μg/sample) staining profiles were used to gate live, single-cell events for data analysis.

Sdc1 and Integrin Expression in Mouse Tissues.

Frozen sections of normal mouse artery, or tumors arising in the mammary gland of transgenic mice expression the wnt or β-catenin oncogenes under control of the mammary gland specific MMTV-promoter were fixed and stained with a rabbit polyclonal antibody specific for Sdc1 and a rat monoclonal antibody specific for the endothelial cell marker PECAM. Tissues were also stained with rabbit polyclonal antibodies to the mouse αv integrin subunit (AB1930), the mouse $\beta_3$ integrin subunit (AB1932) or the mouse $\beta_5$ integrin subunit (AB1926). Non-specific control rabbit or rat IgGs were used to demonstrate specificity. The primary antibodies were stained with Alexa488- or Alexa548-conjugated secondary antibodies and distribution of the receptors in the tissue observed via fluorescence microscopy.

Corneal Pocket Implant Angiogenesis Assay.

A polyhydroxyethylmethacrylate (PolyHEMA) pellet 1 μl in volume containing 100 ng FGF was implanted into pockets surgically prepared in the center of the avascular corneas of 6 wk-old Balb/c mice. Three mice were used as controls and three mice received a 0.2 ml Alzet osmotic pump implanted subcutaneously on the back of the mice. The pump was loaded with 100 μM synstatin$_{82-130}$ in sterile saline and delivers 1 μl into the mouse per hr. The mice were allowed to recover and were maintained for seven days. The extent of angiogenesis was recorded by digital camera images of the living mouse. Fluorescent dextran was then injected into the vascular via retro-orbital injection 1-2 minutes prior to sacrifice. Corneas were surgically removed, mounted on slides and the extent of vascularization observed via fluorescence microscopy.

Example 2—Results

Regulation of $\alpha v \beta_3$ and $\alpha v \beta_5$ Integrin Activity on Endothelial Cells by Recombinant Syndecan-1 Ectodomain.

There has not been a concerted examination of Sdc-1 expression in vascular endothelium. Most reports suggest that it is expressed poorly or not at all on resting, mature vascular endothelium that line blood vessels. However, there are reports that it is expressed on activated endothelial cells participating in angiogenesis in the wounded skin (Elenius et al., 1991; gallo et al., 1996). Sdc-1 is not expressed in endothelial cells lining the rabbit aorta, but expression is upregulated following balloon catheter injury and persists for up to 12 weeks following injury. There is a report that Sdc-1 is upregulated in a subset of vessels during tumor angiogenesis (Gotte et al., 2002). These studies strongly suggest that Sdc-1 becomes expressed on activated cells responding to injury or growth factors. Cultured cells, such as human aortic and human umbilical vein endothelial cells reportedly show expression of Sdc-1 at the mRNA level (Mertens et al., 1992), although, as the inventors note above, as the inventors find that expression of the receptor protein in human umbilical vein endothelial cells is low. However, the expression patterns described may be dependent on the growth factors and supplements, such as brain extract, added to the culture medium.

Figure 1C:
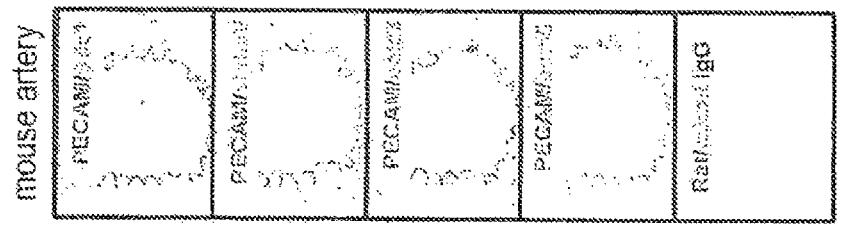
FIGS. 1A-1C—Co-expression of Sdc1, $\alpha_v\beta_3$ integrin and $\alpha_v\beta_5$ integrin by endothelial cells during tumor-induced angiogenesis.
Figure 1B:
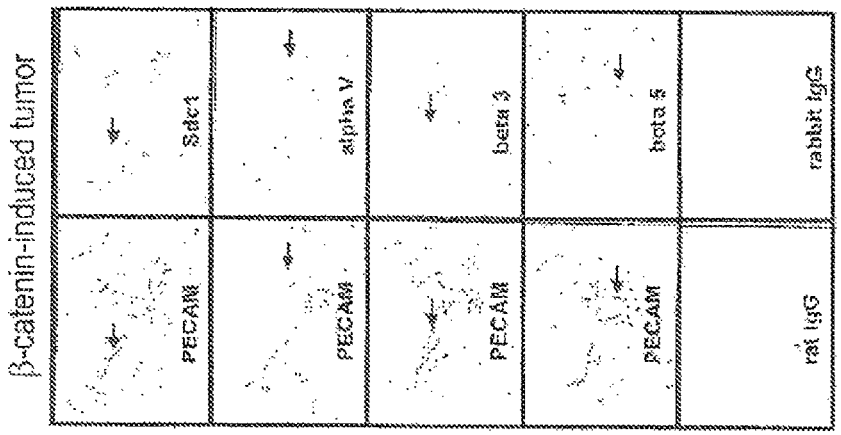
Figure 1A:
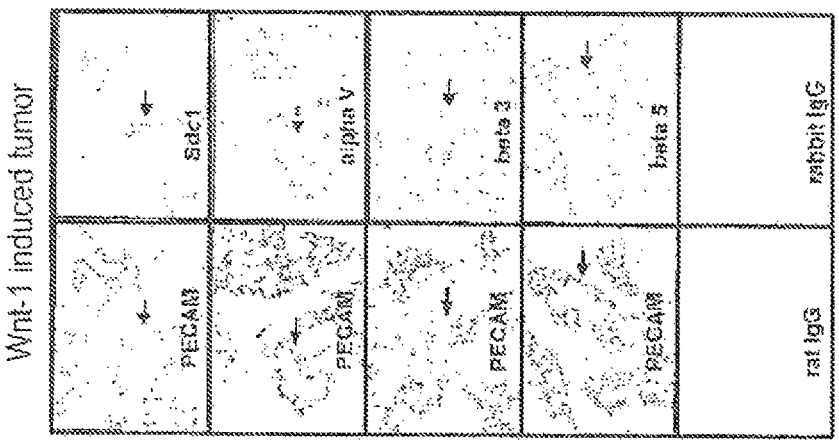

The inventors have now examined the expression of Sdc1 on several types of cultured endothelial cells. Flow cytometry or Western blot analysis of cells shows that human aortic endothelial cells (HAECs), human dermal microvascular endothelial cells (HMEC-1s), mouse aortic endothelial cells, mouse brain endothelial cells and mouse heart endothelial cells have a significant cell surface population of Sdc1 (not shown). In addition, the inventors examined the expression of Sdc1 in the angiogenic vasculature of mouse tumors. The inventors examined mammary carcinomas arising in mice that co-express either the wnt1 oncogene or the β-catenin oncogene. Staining for Sdc1 showed that it is highly expressed in the angiogenic tumor vasculature of both tumors, and is co-expressed at this site with the αvβ3 and αvβ5 integrins (FIG. 1). This is in contrast to a normal mouse artery endothelium which shows little expression of any of these three receptors (FIG. 1).

Figure 2:
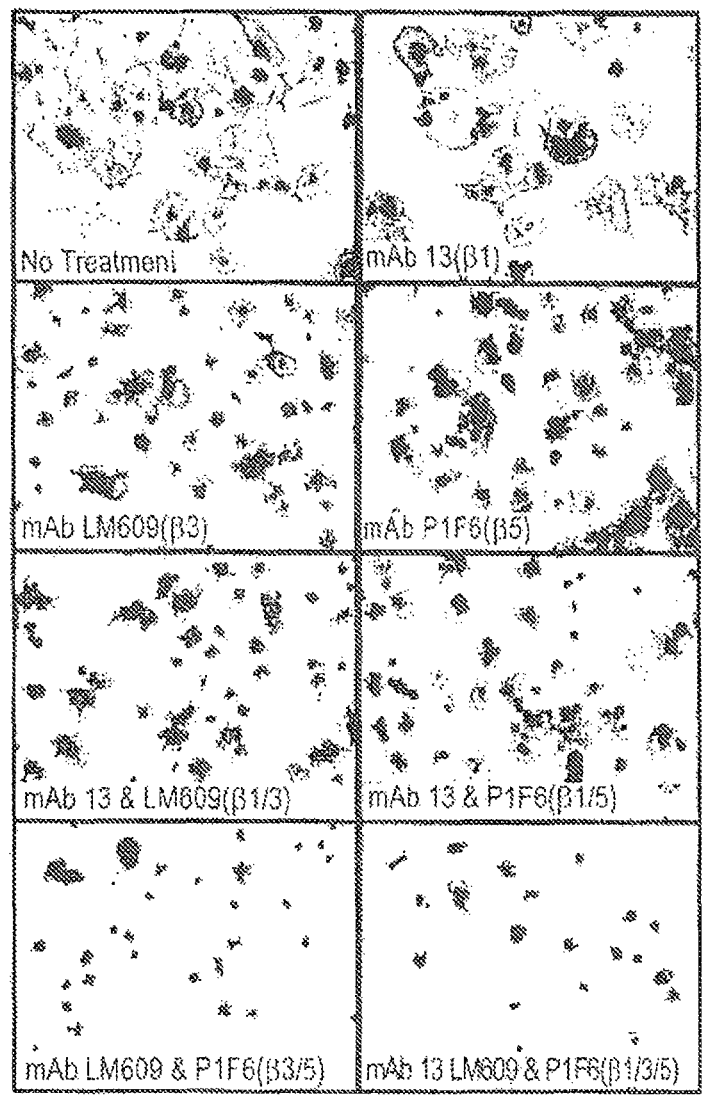
FIG. 2—Human aortic endothelial cells rely on αvβ$_3$ and αvβ$_5$ integrins for spreading on VN. Human aortic endothelial cells (HAECs) were suspended and replated on 10 μg/ml VN in the presence of integrin inhibitory antibodies mAb 13 (specific for β1-containing integrins; this will inhibit the αvβ$_1$ integrin), LM609 (specific for the αvβ$_3$ integrin) and P1F6 (specific for the αvβ$_5$ integrin), or combinations of these mAbs. After 2 hr, the cells were fixed, stained with Alexa488-conjugated phalloidin to aid in visualization, and observed by fluorescence microscopy to document integrin-dependent spreading. Inhibition of spreading requires simultaneous inhibition of both αvβ$_3$ and αvβ$_5$ integrins.

The inventors have examined the Sdc1 regulation of the αvβ3 and αvβ5 integrins in several types of endothelial cells. Human aortic endothelial cells (HAEC) express abundant amounts of the αvβ3 integrin and somewhat less of the αvβ5. The cells also express a high level of the β1 integrin subunit, which is capable of assembling with the αv subunit to form the αvβ1 integrin. All three of these integrins are potential vitronectin receptors and it is thus not surprising that these endothelial cells bind and spread on vitronectin. To assess the actual contribution of each integrin, the inventors have plated the cells on vitronectin in the presence of inhibitory antibodies to the $\beta_1$ integrins (mAb13), the $\alpha v\beta 3$ (LM609) and the $\alpha v\beta 5$ (P1F6). The inventors find that inhibiting the $\alpha v\beta 1$ integrin has little or no effect, but that the HAECs fail to attach and spread normally on VN when both the $\alpha v\beta 3$ and $\alpha v\beta 5$ are inhibited (FIG. 2).

Figure 3:
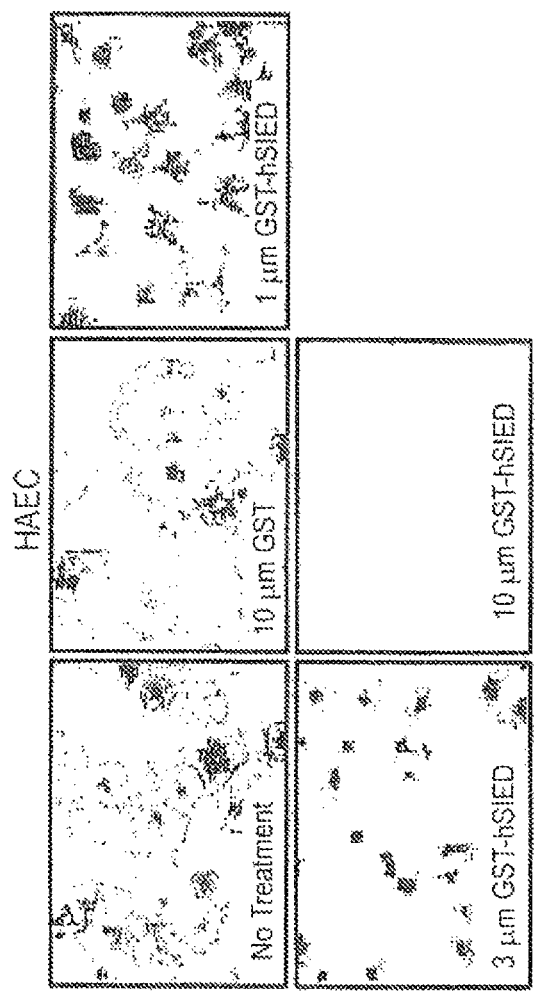
FIG. 3—αvβ$_3$ and αvβ$_5$ integrin-mediated spreading of human aortic endothelial cells on VN is disrupted by recombinant Sdc1 ectodomain fusion protein. HAECs were plated on VN in the presence of no competitor, 1-10 μM GST-mS1ED (recombinant mouse Sdc1 ectodomain expressed as a fusion protein with GST) or GST alone.
Figure 4:
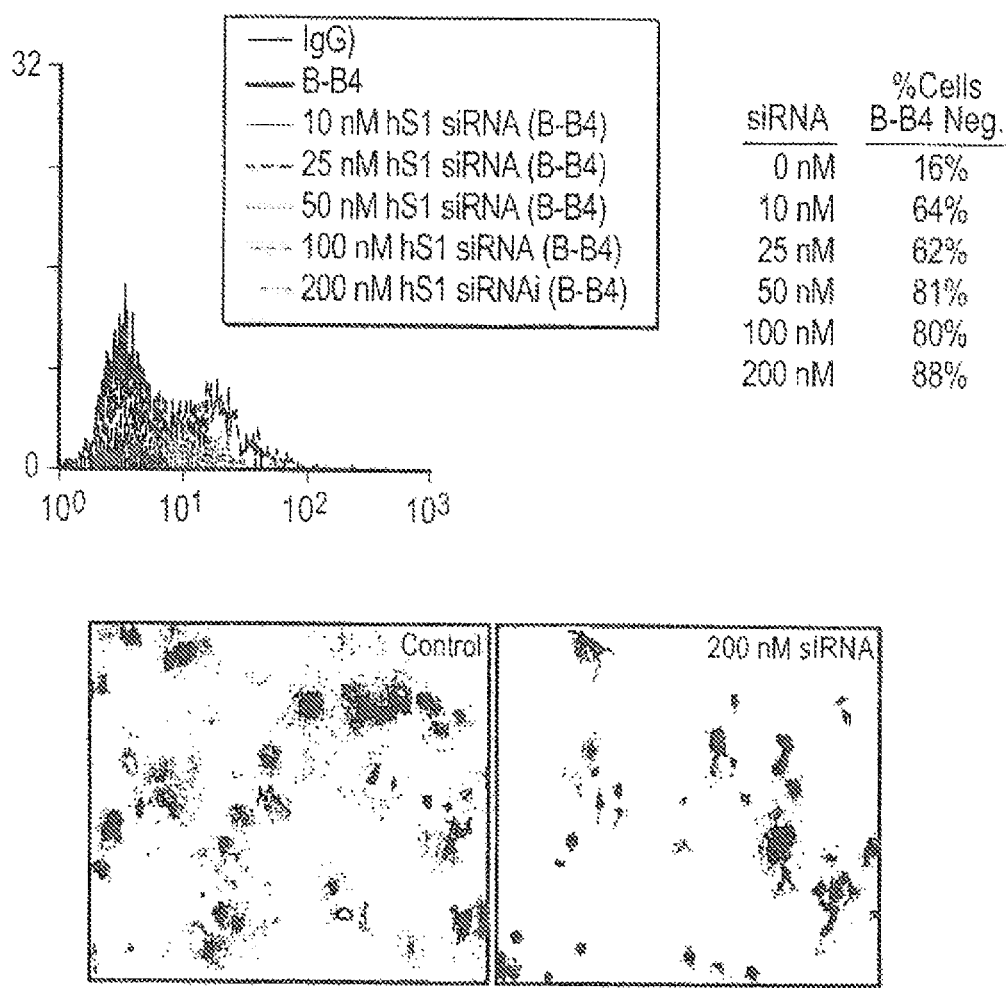
FIG. 4—Inhibition of HAEC spreading on VN by silencing of Sdc-1. HAECs were transfected with a range of concentrations of siRNA specific for human Sdc-1 (hS1), which achieves 80-88% silencing at 100-200 nM, as shown by flow cytometry using human Sdc-1 mAb B-B4. The cells treated with 200 nM siRNA were also plated on VN for 2 hr and display a 60% reduction in cell spreading.
Figure 6A:
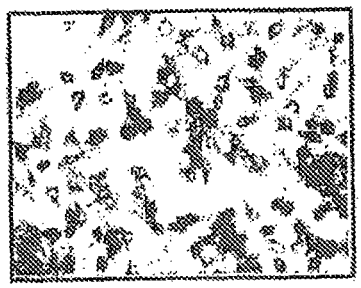
FIGS. 6A-6H—Inhibition of B82L fibroblast and HMEC-1 cell attachment and spreading on VN by synstatins$_{82-130}$. B82L fibroblasts, which rely on the αvβ$_5$ integrin for attachment to VN, and human dermal microvascular endothelial cells, which rely on both the αvβ$_3$ and αvβ$_5$ integrins for attachment to VN, were plated in the absence of peptide (FIGS. 6A, 6E) or in the presence of 0.1 (FIGS. 6B, 6F), 0.3 (FIGS. 6C, 6G) or (FIGS. 6D, 6H) synstatin$_{82-130}$ for 2 hr and processed as described in FIG. 2.
Figure 6B:
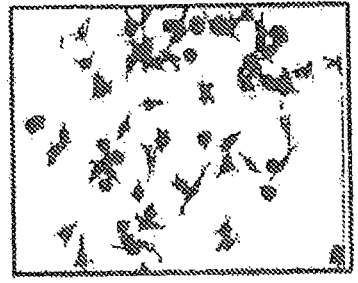
Figure 6C:
Figure 6D:
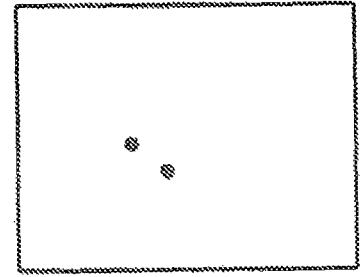
Figure 6E:
Figure 6F:
Figure 6G:
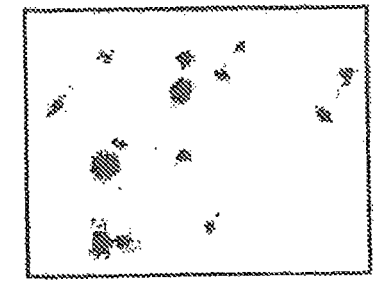
Figure 6H:
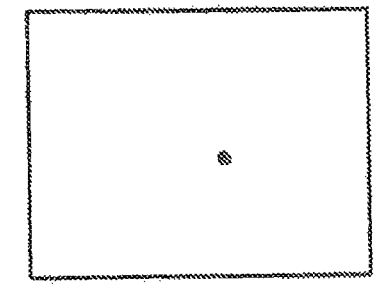
Figure 7A:
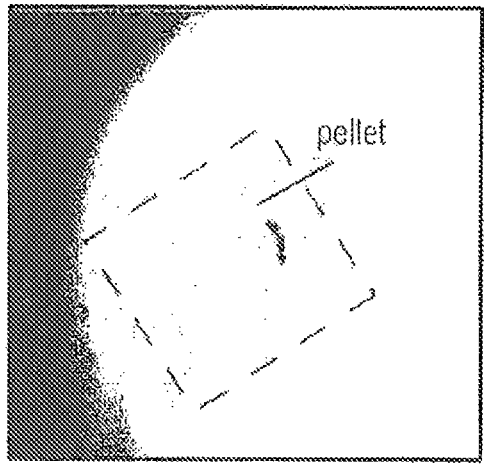
FIGS. 7A-7D—Synstatin82-130 inhibits angiogenesis induced by FGF in vivo. A polyHEMA pellet containing 100 ng FGF was surgically inserted into the center of the mouse cornea. Test mice also received a 2 ml Alzet osmotic pump inserted subcutaneously on their backs, containing 100 μM synstatins$_{82-130}$. The mice were allowed to recover and were maintained for seven days before sacrifice. Fluorescent dextran was injected into the vascular system via retro-orbital injection just prior to sacrifice.
Figure 7B:
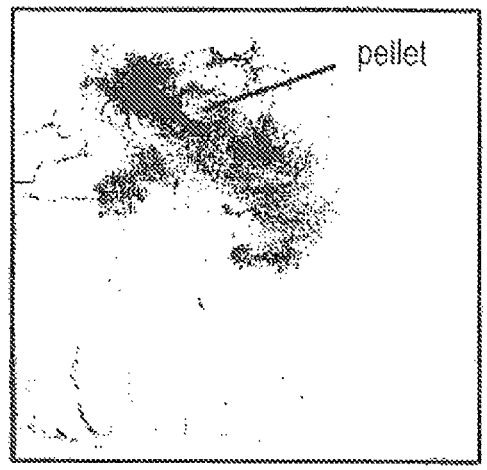
Figure 7C:
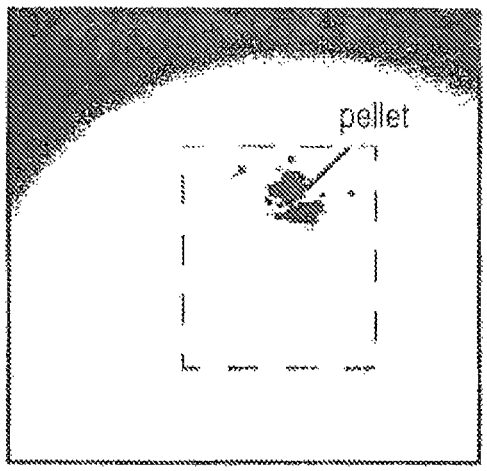
Figure 7D:
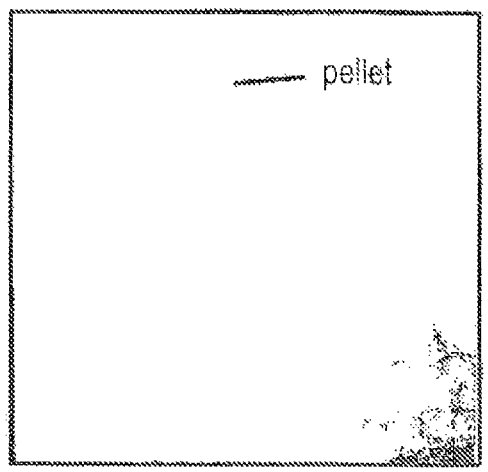

The next test was whether agents that target Sdc1, especially competition with recombinant S1ED, will block the activity of these two integrins and thus block their interaction with VN. The inventors find that, indeed, the HAEC cell spreading on VN is blocked by the soluble S1ED at a concentration similar to that of the $\alpha v\beta 3$ in mammary carcinoma (Beauvais and Rapraeger, 2003) and that of the $\alpha v\beta 5$ integrin in B82L fibroblasts (McQuade et al., 2006) (FIG. 3). Since the work with inhibitory integrin antibodies demonstrated that both integrins must be blocked on these cells in order to block cell spreading, the inventors conclude that the recombinant protein must disrupt signaling by both of these integrins. The inventors have also performed this analysis with mouse aortic endothelial cells, which express Sdc1, and find that they are also exquisitely sensitive to competition by the Sdc1 ectodomain, with spreading on VN blocked using 1 competitor. The inventors have also shown this with human microvascular endothelial cells (HMEC-1), which are inhibited in this assay by S1ED with an $IC_{50}$ of approximately 3-10 µM. Secondly, the inventors targeted Sdc1 expression in the cells using siRNA. The preliminary experiments demonstrate that at 100 nM siRNA, which silences Sdc1 expression by 80%, the spreading of the HAECs on VN is also disrupted (FIG. 4). Thus, Sdc1 on endothelial cells appears to be a necessary regulator of the $\alpha v\beta 3$ and $\alpha v\beta 5$ integrins and this regulatory activity, and thus the activation of the integrins themselves, is blocked by soluble S1ED; this mimics the inhibition that the inventors have observed and published with the human mammary carcinoma cells (Beauvais and Rapraeger, 2003) and B82L fibroblasts (McQuade et al., 2006) and indicates that the protein is a promising inhibitor of angiogenesis caused by tumors and other human diseases.

Inhibition of Angiogenesis In Vivo by Synstatin.

The inventors have now extended these findings to more direct angiogenesis assays, using as inhibitors the recombinant Sdc1 ectodomain and also using a shorter peptide encompassing the active site within the Sdc1 ectodomain that the inventors refer to as "synstatin".

The recombinant Sdc1 ectodomain (SLED) is comprised of 234 amino acids extending from the N-terminal signal sequence of the protein to the transmembrane domain (amino acids 18-252). The recombinant protein is expressed in bacteria as an epitope-tagged protein (GST fusion protein or 6×His-tagged protein) for ease of purification on glutathione or nickel columns, respectively.

The peptide that the inventors have developed encompasses amino acids 82-130 of the mouse Sdc1 sequence (a 49 amino acid sequence). Thus, this peptide is referred to as "synstatin$_{82-130}$". Mutational analysis of the Sdc1 expressed in cells suggests that the active site necessary for activating the $\alpha v\beta 3$ integrin resides in amino acids 88-121 (a 34 amino acid sequence). The active site for the $\alpha v\beta 5$ integrin has not been defined yet by mutational analysis, but clearly traces to the ectodomain and likely to the same site. Thus, the inventors envisioned that synstatin$_{82-130}$ would contain the active site necessary in Sdc1 for regulating both integrins and that it would compete with this regulatory activity on the cells.

The assays that the inventors have used to test the activity of synstatin$_{82-130}$ and to compare it to the native ectodomain (SLED) on which its sequence is based are: 1) adhesion of cells to vitronectin, which is a ligand for the $\alpha v\beta 3$ and $\alpha v\beta 5$ integrins, and 2) growth of angiogenic blood vessels into the avascular mouse cornea in response to the implantation of a pellet containing the angiogenic factor FGF—again a process that relies on these integrins.

Inhibition of Adhesion and Spreading on Vitronectin (VN).

The inventors have tested the adhesion and spreading of MDA-MB-231 mammary carcinoma cells on VN in the presence or absence of synstatin$_{82-130}$. These cells rely specifically on the active $\alpha v\beta 3$ integrin for this adhesion (Beauvais et al., 2004). Recombinant Sdc1 ectodomain (S1ED) has been shown by the inventors previously to block spreading of these cells with an $IC_{50}$ of about 3-10 µM (Beauvais et al., 2004). In contrast, the inventors find that synstatin$_{82-130}$ has an $IC_{50}$ of about 0.1 µM, indicating that it is about 30-100× more effective (FIG. 5). A 1 µM concentration of synstatin$_{82-130}$ completely blocks cell attachment, an outcome that the inventors have not seen with the highest concentrations of recombinant S1ED tested (50 µM). As a control, the inventors tested cell adhesion and spreading on fibronectin, a ligand on which the cells use the $\alpha 5\beta 1$ integrin and do not rely on the $\alpha v\beta 3$ integrin; synstatin$_{82-130}$ has no effect on attachment and spreading on this ligand (FIG. 5). Thus, synstatin$_{82-130}$ is a specific and effective inhibitor of $\alpha v\beta 3$ integrin activation.

Similar findings are observed with B82L fibroblasts (FIG. 6). The inventors have shown previously that these cells rely solely on the $\alpha v\beta 5$ integrin to recognize VN, and that this recognition also depends on activation of the integrin by Sdc1 (McQuade et al., 2006). Recombinant Sdc1 affects this process with an $IC_{50}$ of ca. 3-10 µM, similar to its inhibition of $\alpha v\beta 3$ integrin activation in the carcinoma cells (McQuade et al., 2006). Synstatin$_{82-130}$ disrupts the spreading of the B82L cells on VN with an $IC_{50}$ of ca. 0.1 µM, and completely blocks any cell attachment at 1 µM.

Finally, the inventors have examined HMEC-1 cells, which are immortalized human dermal microvascular endothelial cells. Microvascular endothelial cells are regarded as being the main source of endothelial cells that carry out angiogenesis in vivo. The HMEC-1 cells grown in serum-containing culture medium express Sdc1 (as noted earlier) and also express active $\alpha v\beta 3$ and $\alpha v\beta 5$ integrins. The inventors find using inhibitory antibodies to the $\alpha v\beta 3$ and/or $\alpha v\beta 5$ integrins that the HMEC-1 cells attachment to VN is dependent on these two integrins and both must be inhibited to disrupt attachment and spreading on this ligand (not shown), similar to the analysis shown for the HAECs in FIG. 2. Recombinant S1ED blocks the spreading on VN with an $IC_{50}$ of 3-10 µM, similar to its disruption of $\alpha v\beta 3$ and/or $\alpha v\beta 5$ integrins on the mammary carcinoma and B82L cells (Beauvais and Rapraeger, 2003; Beauvais et al., 2004; McQuade et al., 2006). Synstatin$_{82-130}$ is again more effective, disrupting spreading with an $IC_{50}$ of approximately 0.1 µM (FIG. 6). Thus, the peptide inhibitor synstatin$_{82-130}$ derived from the native sequence of Sdc1 is a highly effective inhibitor of these two integrins on endothelial cells as well as other cells that rely on either of these two integrins.

Inhibition of Angiogenesis In Vivo by Disrupting the Sdc1 Regulation of αvβ3 and αvβ5 Integrins.

To test the efficacy of synstatin$_{82-130}$ in vivo, the inventors have used the mouse corneal pocket implant angiogenesis assay. Here, angiogenesis is induced in the avascular mouse cornea by implantation of a polyHEMA pellet containing fibroblast growth factor (FGF), which is a potent angiogenic agent. The FGF will induce angiogenic outgrowth of new vessels from the limbic vessels at the margin of the cornea into the avascular region at the center of the cornea where the pellet is implanted. The inventors have tested recombinant S1ED by supplying it along with the FGF in the pellet implanted into the cornea, and have also introduced it into the systemic circulation of the mouse through the use of an osmotic pump placed subcutaneously on the back of the animal. The latter protocol more closely mimics the manner in which such an inhibitor might be delivered as a drug in patients. In both circumstances recombinant S1ED blocks the FGF-induced angiogenesis. The concentration necessary for the block in vivo has not yet been measured. It is supplied at a concentration of 2.4 mM in the osmotic pump, which delivers 1 µl into the mouse per hour; if the inventors assume that it is contained within the 2 ml blood volume of the mouse, and assume that there is no protein degradation or clearance, then it would achieve concentrations of approximately 29 µM after 24 hr. However, this is likely to be a high estimate, as clearance and degradation are likely to occur, and the protein is likely to be present in the greater volume of the mouse than just the vascular system. Thus, the recombinant protein may be highly effective in vivo at concentrations of 29 µM or less.

The inventors have tested synstatin$_{82-130}$ in the corneal angiogenesis protocol as well, delivering it into the mouse circulation via the osmotic pump as described for S1ED. The starting concentration in the pump is 100 µM, 24-fold lower than S1ED; using the same assumptions and caveats as noted for pump delivery of recombinant S1ED, the systemic concentration of the inhibitor may reach 1.2 µM after 24 hr. Again, this is likely a high estimate. In six mice tested to date, the inventors have seen a complete inhibition of angiogenesis via systemic delivery of synstatin$_{82-130}$. Control mice containing the FGF implant show extensive vessel outgrowth extending from the limbus vessel at the perimeter of the cornea to the pellet in the center, where the new angiogenic vessels engulf the FGF pellet (FIG. 7). In mice with systemically-delivered synstatin$_{82-130}$, the mice show no angiogenesis (FIG. 7). The inventors have not yet tried lower concentrations. It should be emphasized that following the one week of treatment with this concentration of inhibitor that is highly effective against angiogenesis, these mice show no ill effects. They are active, eat normally, maintain weight and show no altered behavior.

Example 3

Introduction

Angiogenesis, or the sprouting of new blood vessels from existing ones, occurs in development and in diseases such as diabetic retinopathy, endometriosis, and tumor-induced angiogenesis. The mature, resting endothelial cells in the donor vessels are activated to progress through an angiogenic program, in which they undergo proliferation and invasion, maturation, and apoptosis; the latter, also known as "vascular pruning" is especially important in molding the architecture of the new vessels (Bergers and Benjamin, 2003; Stupack and Cheresh, 2003).

FGF and VEGF, two growth factors often released by tumors, are potent angiogenic factors. Their activities are closely tied to the activity of two integrins, the α$_v$β$_3$ and α$_v$β$_5$ integrins (Stupack and Cheresh, 2003), which have roles in the chemotactic migration and in the survival of the endothelial cells. The expression of these two integrins is induced by FGF and VEGF signaling and the integrins and growth factor receptors then collaborate in the signaling pathways leading to angiogenesis. Uncoupling of this signaling by inactivation of either type of receptor leads to apoptosis of the endothelial cells (Stupack et al., 2001) and this mechanism is believed to have a major role in vessel pruning as the new vasculature acquires its final architecture. The α$_v$β$_3$ and α$_v$β$_5$ integrins are not generally expressed in adult cells, with the exception of a few sites such as osteoclasts, but their expression on activated endothelial cells during angiogenesis (Byzova et al., 1998) as well as in many tumors during metastasis, makes them attractive targets for combating tumorigenesis. A choice target is their apoptotic role, as triggering apoptosis of the endothelial cells will starve the tumors that require a new vascular supply for nutrient and gaseous exchange. Indeed, this apoptotic role of the integrin may explain why β$_3$ and β$_5$ knockout mice exhibit increased angiogenesis, whereas inhibitors of the α$_v$β$_3$ and α$_v$β$_5$ integrins in normal mice are anti-angiogenic; it is hypothesized that potent apoptotic signaling arises from these integrins when they are inhibited in wild-type mice, whereas the integrin null mice are freed from this apoptotic mechanism (Bader et al., 1998; Reynolds et al., 2002).

The activation of an integrin typically refers to a conformation change that allows ligand binding. The α$_v$β$_3$ has been used as a model to understand this activation mechanism. It proceeds through at least two activation states, each resulting in a change in conformation of the extracellular domain in response to intracellular signals and extracellular ligand binding (Boettiger et al., 2001; Boettiger et al., 2001; Du et al., 1991; Frelinger et al., 1991; Humphries, 1996; Liddington and Ginsberg, 2002; Pelletier et al., 1996; Plow et al., 2000; Xiong et al., 2001; Yan et al., 2000). "Activating" or "inactivating" antibodies directed to the integrin extracellular domain serve to confine it to one or the other conformation. One such antibody, LM609, freezes the α$_v$β$_3$ integrin in the inactive conformation, blocks angiogenesis and leads to endothelial cell apoptosis. A humanized version of this antibody (Vitaxin) is in clinical trials as an antitumor agent.

The syndecans are multifunctional matrix receptors on the surface of all adherent cells. They anchor to the matrix via heparan sulfate glycosaminoglycan chains and communicate to the cytoplasm via short but highly conserved cytoplasmic domains. The heparan sulfate chains have important signaling properties, as they enhance the assembly of growth factor with their receptor tyrosine kinases. However, it is becoming clear that the syndecan proteins have important regulatory roles as well, often leading to the description of this family as "co-receptors," as they assemble with and control the signaling of other receptors on the cell surface. Several reports now indicate that specialized sites may exist within the syndecan extracellular protein domains, which if mutated or targeted with antibodies, disrupt tumor cell invasion. If true, such sites may hold promise as targets for therapeutic drugs to combat tumorigenesis.

Syndecan-1 Associates with the α$_v$β$_3$ and α$_v$β$_5$ Integrins, and this Association is Disrupted by SSTN.

Figure 8A:
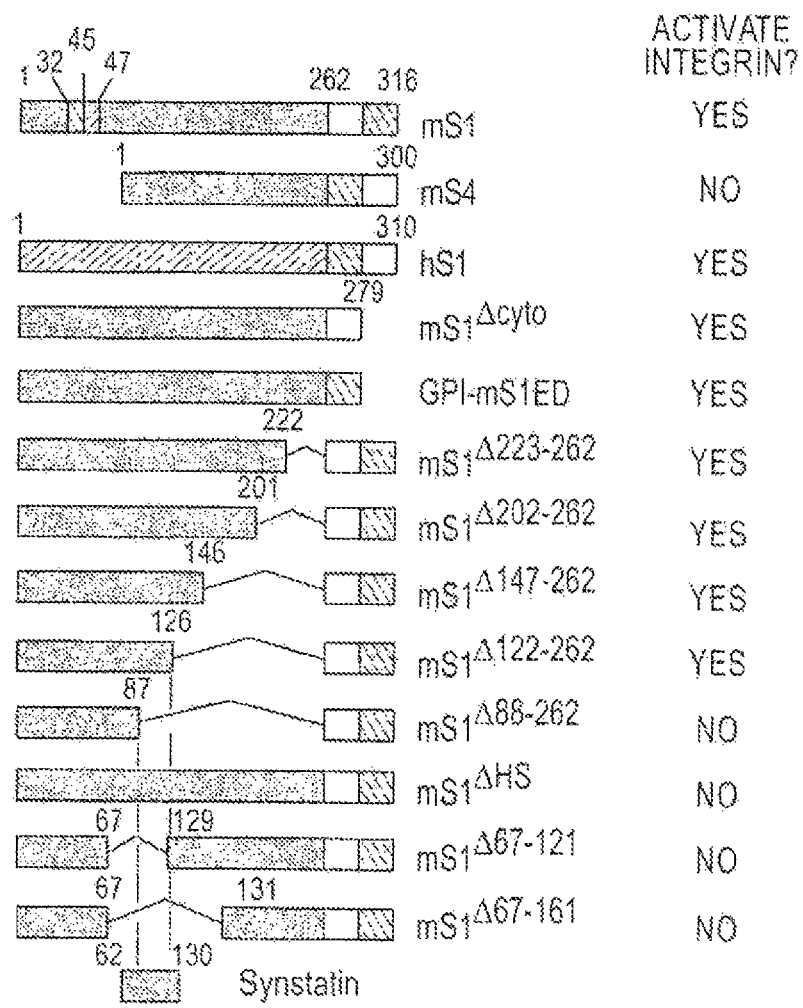
FIGS. 8A-8D—SSTN disrupts association of syndecan-1 with the α$_v$β$_3$ and α$_v$β$_5$ integrins.

The inventors have described a role for syndecan-1 in regulating activation of the α$_v$β$_3$ integrin in human mammary carcinoma cells, and the α$_v$β$_5$ integrin in B82L mouse fibroblasts. This regulation involves a site in the extracellular domain of syndecan-1, demonstrated in human MDA-MB-231 or MB-435 mammary carcinoma cells, which utilize the $\alpha_v\beta_3$ integrin to bind, spread or migrate on vitronectin. Integrin activity is abolished by silencing syndecan-1 expression with human-specific siRNA, and is rescued by re-expressing mouse syndecan-1; however, deletion mutants lacking a region of the extracellular domain encompassing amino acids 88-121 in the mouse sequence fail to rescue (FIG. 8A). This sequence has a high degree of conservation across mouse, hamster, rat and human syndecan-1 (FIG. 9).

Figure 8B:
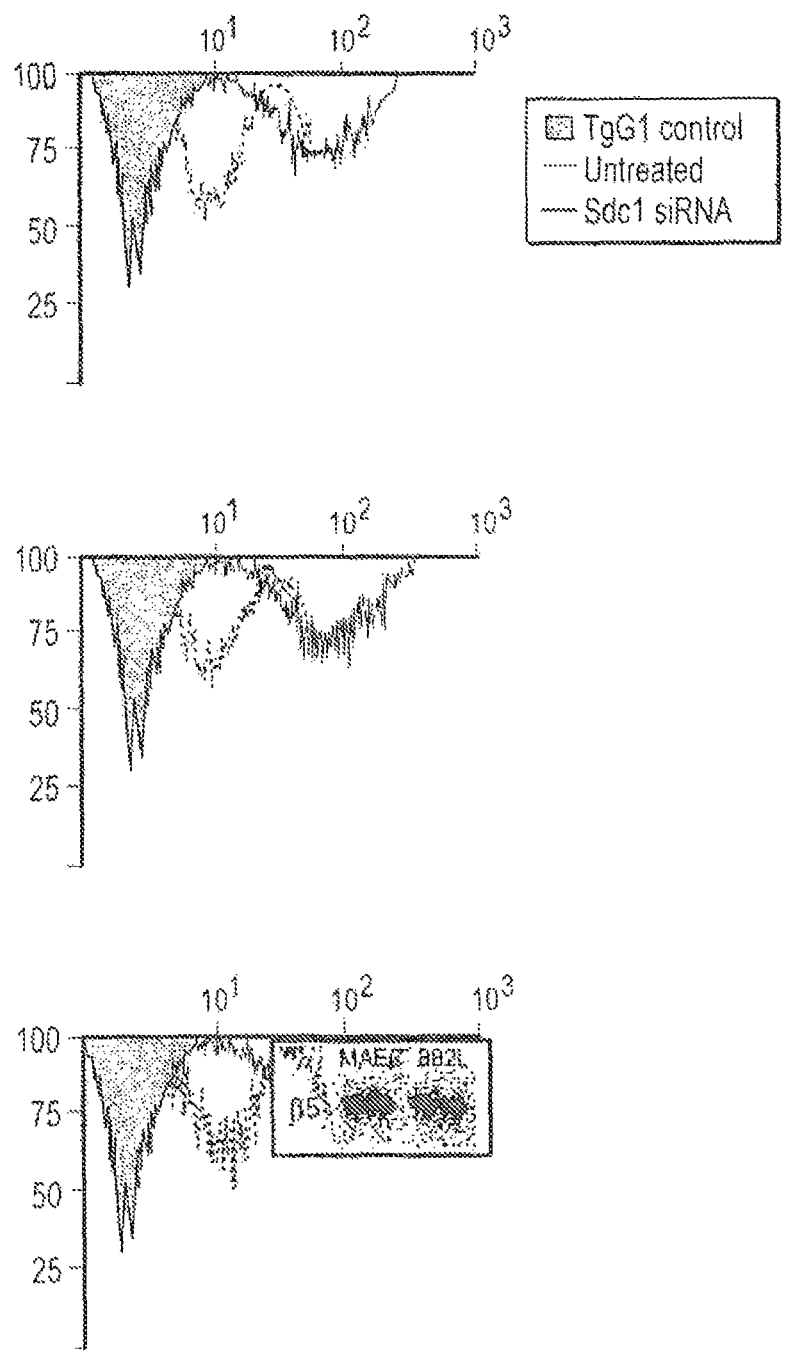

Because syndecan-1 regulates both of these integrins that are attractive targets for anti-angiogenic therapy, the inventors questioned whether this regulatory mechanism existed on endothelial cells. Although some reports indicate that syndecan-1 is not expressed on vascular endothelium (Elenius et al., 1991; Gallo et al., 1996; Hayashi et al., 1987; Kainulainen et al., 1996), other reports suggest that it is upregulated on activated endothelial cells undergoing angiogenesis (Elenius et al., 1991; Gallo et al., 1996; Gotte et al., 2002; Kainulainen et al., 1996). The inventors examined the expression of syndecan-1 and the two integrins on three lines of vascular endothelial cells by flow cytometry (FIG. 8B). Human aortic endothelial cells and human dermal microvascular endothelial cells all express modest levels of syndecan-1 and a larger population of the $\alpha_v\beta_3$ and $\alpha_v\beta_5$ integrins. Mouse aortic endothelial cells express higher levels of syndecan-1 than their human counterparts, but less of the $\alpha_v\beta_3$ integrin. Although a reliable antibody for detecting the mouse $\alpha_v\beta_5$ integrin by flow is not available, it can be shown that they also express the $\alpha_v\beta_5$ integrin by western blot, shown in comparison to B82L fibroblasts (FIG. 8B), known to express this integrin.

Figures 8C, 8D:
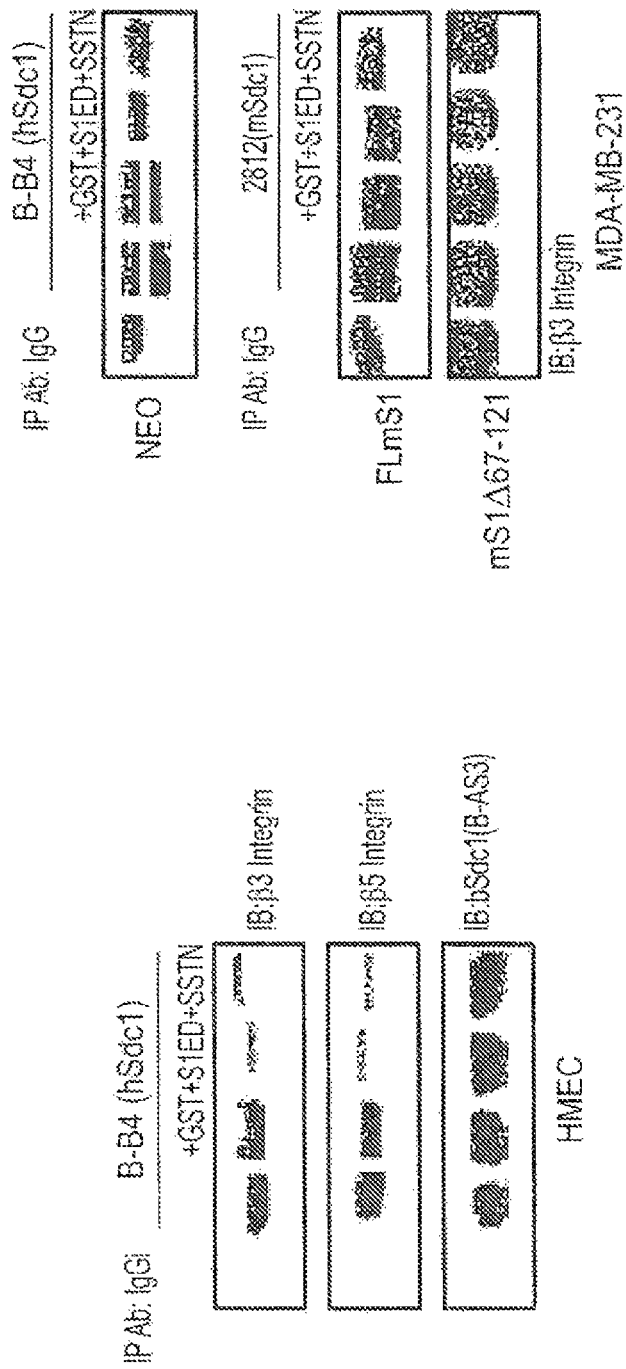

To determine if the syndecan and integrins are in a regulatory complex, blots containing syndecan-1 immunoprecipitated from HMECs were probed for the co-precipitation of the $\beta_3$ and $\beta_5$ integrin subunits; this is indicative of an association of the syndecan with the $\alpha_v\beta_3$ and $\alpha_v\beta_5$ integrins as these $\beta$ subunits associate only with the $\alpha_v$ subunit at endothelial cell surfaces. Both integrins co-precipitate with the syndecan and in seemingly equal proportions suggestive of a roughly 1:1 correspondence (FIG. 8C). Next, to determine if the interaction is dependent on the site identified in the syndecan-1 ectodomain, the cells were preincubated with either GST-mSED, a recombinant GST fusion protein containing the ectodomain of mouse syndecan-1, or a peptide (called "synstatin" or SSTN) containing the active site in syndecan-1. Mouse syndecan-1 ectodomain is used as it is not recognized by the human-specific monoclonal antibodies used to immunoprecipitate the syndecan. Both the recombinant protein and the SSTN peptide compete with the interaction and displace the integrins from the human syndecan-1 expressed on the endothelial cells (FIG. 8C). Lastly, immunoprecipitations were performed using MDA-MB-231 human mammary carcinoma cells expressing either native mouse syndecan-1 in addition to the endogenous human counterpart, or a mouse mutant containing a Δ67-121 deletion that removes the putative active site at 88-121. The $\alpha_v\beta_3$ integrin expressed by these cells co-immunoprecipitates with either the human or the mouse syndecan-1, these interactions are competed by either the full-length recombinant S1ED or the SSTN peptide, and the integrin fails to associate with the mouse mutant lacking the active site (FIG. 8D). Thus, syndecan-1 appears to associate with the $\alpha_v\beta_3$ and $\alpha_v\beta_5$ integrin in vascular endothelial cells as a putative regulatory mechanism that can be disrupted by SSTN.

The $\alpha_v\beta_3$ and $\alpha_v\beta_5$ Integrin on Vascular Endothelial Cells are Regulated by Syndecan-1.

Figure 10B:
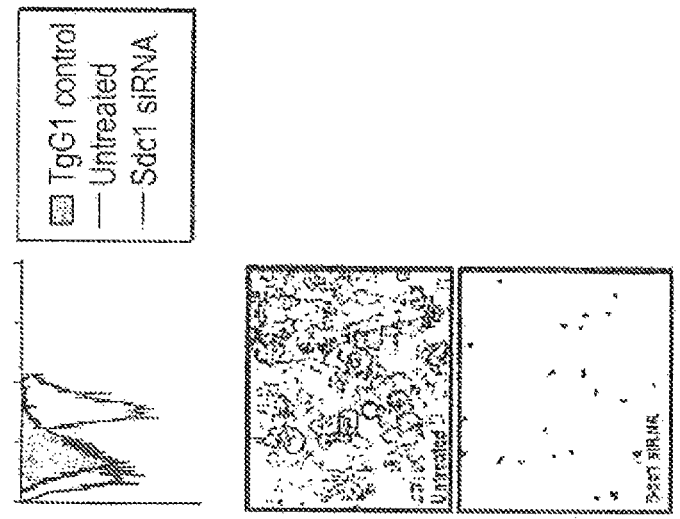
Figure 10A:
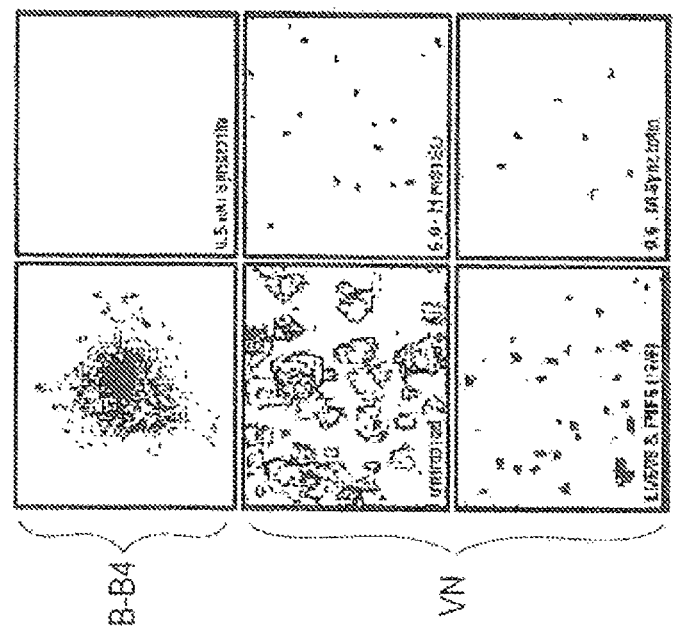
Figure 10C:
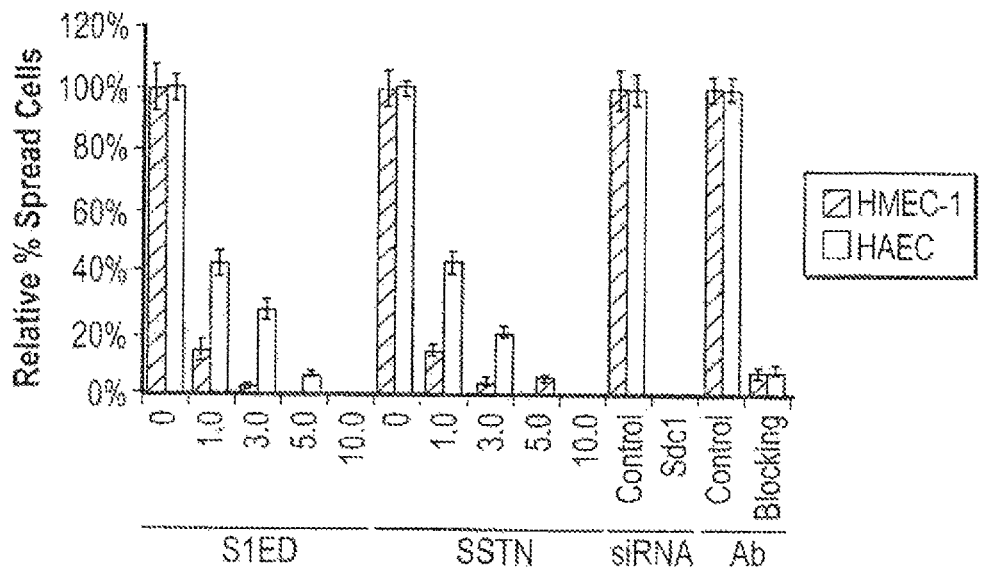

The inventors next questioned whether SSTN is inhibitory to integrin activation. HMECs plated on a substratum consisting solely of a monoclonal antibody (B-B4) to syndecan-1 attach to the antibody and spread. Their prior work has suggested that the cell spreading requires integrin activation and signaling. Indeed, the $\alpha_v\beta_3$ integrin on the cells is activated, detected by staining the cells with the ligand-mimetic antibody WOW-1 (FIG. 10A); this antibody binds only to activated integrin. However, co-incubation of the cells with 0.5 µM SSTN prevents both the cell spreading and recognition by WOW-1, indicating that competitive displacement of the integrin from the ligated syndecan prevents integrin activation. Identical results are seen in the converse experiment, namely plating the cells on vitronectin, a ligand for both the $\alpha_v\beta_3$ and $\alpha_v\beta_5$ integrins. The spreading of the cells is dependent on both integrins; spreading is blocked in the presence of antibodies LM609 and P1F6 (FIG. 10A), which inactive the $\alpha_v\beta_3$ and $\alpha_v\beta_5$ integrins, respectively, but is not blocked in the presence on either antibody alone (not shown). However, addition of either 5.0 µM recombinant mS1ED or 0.5 µM SSTN blocks spreading as effectively as the combined antibody treatment (FIG. 10A). An identical result is obtained if syndecan-1 expression is silenced with siRNA (FIG. 10B). Both findings support the conclusion that syndecan-1 is simultaneously regulating the activation of both integrins on vascular endothelial cells.

Figure 10D:
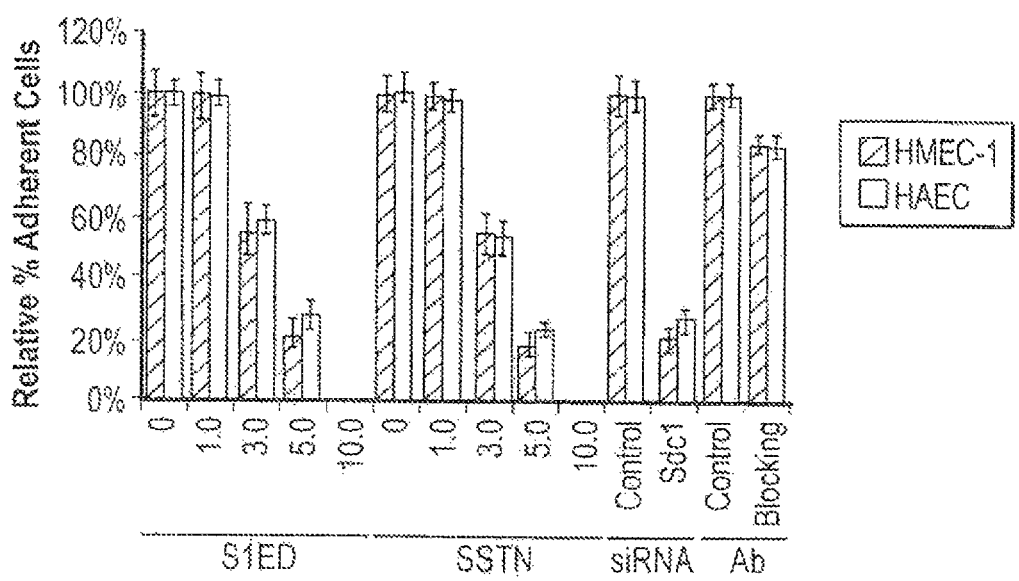

The effective inhibitory concentration of SSTN is lower than that of the recombinant mS1ED protein. This is shown using either HMECs or human aortic endothelial cells plated on vitronectin and quantifying cell spreading (FIG. 10C) or cell attachment (FIG. 10D). Competition with mS1ED at 1-3 µM concentrations reduced cell spreading by over 80-90%, respectively for the HMECs, and displays at IC50 of about 1 µM for HAECs, which are more resistant than the HMECs. Complete integrin inactivation necessary for blocking cell attachment altogether requires over a 10-fold higher concentration of 10 µM. In comparison, SSTN displays inhibitory activity equal to that of mS1ED when used at a 10-fold lower concentration and has significant inhibitory properties in the 0.1-0.3 µM range. At this concentration it is equal or more effective than 10 µg/ml of the inhibitory antibodies LM609 and PIF6. Although the reason for the greater inhibition by SSTN is not known, it may trace to misfolding of the mS1ED protein when expressed in bacteria, or it may indicate that the SSTN sequence in the full ectodomain is partially hidden. Computer modeling of the syndecan or SSTN sequence is not reliable as the proteins have little or no homology to any proteins that have been crystallized to date.

Syndecan-1 is Expressed During Angiogenesis.

To test the activity of SSTN as an anti-angiogenic agent, the inventors turned to the in vitro aortic ring outgrowth assay and the in vivo corneal angiogenesis model. The aortic outgrowth assay allows quantification of microvessel outgrowth from segments of mouse aorta explanted to type I collagen gels. As was found when examining the mouse aortic endothelial cell line in culture, both syndecan-1 and the $\alpha_v\beta_3$ and $\alpha_v\beta_5$ integrins appear present even on the resting mouse aorta (FIG. 11A). In addition, microvessels growing out from the aortic explant over a 7 days period in response to FGF stain positively for syndecan-1, with appears co-expressed with the $\alpha_v\beta_3$ and $\alpha_v\beta_5$ integrins (FIG.

11B). To extend this finding of syndecan-1 expression in activated endothelium, the inventors also examined two models of mouse breast tumor formation. Tumors derived from wnt-1 overexpression in the mammary gland show a high degree of vascularization, identified as internal networks lined by a thick cell layer than stains intensely for syndecan-1 and for PECAM (CD31), indicative of activated endothelium (FIG. 11C). In fact, syndecan-1 expression in these cells swamps out the positive staining for syndecan-1 seen in the mammary epithelial cells, which are known to be positive for syndecan-1. These same cell layers as positive for $\alpha_v$, $\beta_3$ and $\beta_5$ integrin subunits. A similar finding is seen in tumors arising from overexpression of β-catenin (FIG. 11C). Although the vascularization is not as extensive as in the β-catenin-induced tumors, there are clear thickened layers of cells that are PECAM, syndecan-1 and $\alpha_v\beta_3/\alpha_v\beta_5$ integrin positive in these mammary tumors.

SSTN Inhibits Angiogenesis In Vitro and In Vivo.

To test the effect of SSTN on microvessel outgrowth, segments of thoracic aorta were explanted to collagen gels in the presence of either 50 ng/ml vascular endothelial cell growth factor (VEGF) or 30 ng/ml FGF-2, and incubated in the presence of either recombinant mS1ED or SSTN. Although one vessel outgrowth is observed in the absence of exogenous angiogenic agents, likely due to VEGF release by supporting cells growing out from the explant, the outgrowth is greatly (≥10-fold) increased by FGF or VEGF (FIG. 12). Addition of recombinant mS1ED blocks VEGF-induced outgrowth by more than 70% at 10 μM, and greater than 95% at 30 μM. FGF induced outgrowth requires slightly higher inhibitory concentrations (approximately 30 μM mS1ED for 70% inhibition), which may trace to a difference in susceptibility of the two integrins, as VEGF signaling is reportedly coupled to $\alpha_v\beta_5$ integrin activation and FGF signaling is coupled to $\alpha_v\beta_3$ activation. SSTN is 10-fold more potent as an anti-angiogenic agent, displaying an IC50 of 0.1 μM in FGF and a slightly greater IC50 in response to VEGF. These concentrations are much in line with the IC50's displayed in the in vitro cell attachment and spreading assays with HMECs and HAECs. It should be noted that the microvessel outgrowth is accompanied by the outgrowth of support cells, most likely smooth muscle cells and fibroblasts. These cells are not endothelial cells, as they do not stain positively for PECAM, and their outgrowth is unaffected by mS1ED or SSTN (FIG. 12). Thus, the effects of SSTN are highly localized to the vascular endothelial cells.

Lastly, SSTN was tested in the in vivo corneal angiogenesis assay. Polyhydroxyethylmethylacrylate pellets (0.25 μL) containing 67 ng FGF-2 and sucralfate as a slow release agent were implanted into the avascular mouse cornea. After seven days, fluorescent dextran was injected suborbitally to highlight the vascular system and the mice were sacrificed. Visual inspective of either the eye or the dissected cornea shows significant vessel ingrowth towards the implanted pellet from the limbic vessel at the margin of the cornea. Initial experiments found that incorporation of recombinant mS1ED into the pellet reduced the angiogenesis (data not shown). To supply the inhibitor in a more quantifiable and physiological manner, recombinant mS1ED or SSTN were delivered systemically via Alzet osmotic pumps implanted subcutaneously on the backs of the animals. Pumps containing either 2500 μM recombinant mS1ED or 30 SSTN achieved a nearly total block of angiogenesis. Testing a range of SSTN concentration in the pump showed that 50% inhibition of angiogenesis is achieved by 3-10 μM SSTN concentrations in the pump (FIG. 13). To correlate this with the active concentration in the plasma, the inventors took advantage of rabbit polyclonal antibodies generated against mS1ED, which detect active SSTN on dot blots. The antibodies appear to recognize an active conformation of SSTN, as heating the peptide to 95° C. causes it to lose its inhibitory activity and its recognition by antibodies on dot blots (data not shown). Using this method to detect active SSTN in the blood collected from animals after 1 week of SSTN treatment, SSTN is shown to be in the blood at 125-150 nM when present at 10 in the osmotic pump. This correlates well with the IC50 of ca. 0.1 μM observed in vitro and suggests a clearance rate of 10-13 hr in the plasma.

Effective Size of SSTN Peptide.

The SSTN peptide that we have used is $SSTN_{82-130}$, based on the mouse sequence (cf. FIG. 9). This peptide spans the active site in mouse syndecan-1 and retains flanking amino acids on either side in case they are required to maintain structure. The peptide contains two adjacent regions in which the amino acids are highly conserved across species, suggestive of a conserved function (FIG. 14). Truncation of $SSTN_{82-130}$ to smaller peptides that delete portions of these conserved sites cause loss of activity (FIG. 14). Thus, $SSTN_{88-121}$, which retains one amino acid C-terminal and one amino acid N-terminal to the conserved domain is active, but $SSTN_{88-117}$, which removes four of the conserved amino acids at the C-terminus is 3-fold less active in cell attachment and spreading assays on VN. Thus, it appears that the most active SSTN peptide is that which retains both of these conserved sequences.

Effects of SSTN on CAG Myeloma Tumor Formation In Vivo.

The inventors have introduced human CAG myeloma cells expressing luciferase into immunodeficient SCID mice and treated the mice either with SSTN or control PBS. $10^5$ cells were injected subcutaneously into the haunches of 10 animals and allowed to grow for 10 days. At this point, tumors have begun to form and can be detected by manual palpation or by imaging the luciferase-expressing tumor cells. Alzet pumps containing either PBS or 100 μM SSTN were implanted on the backs of the animals and the tumors allowed to grow for an additional 28 days. The pumps are 28-day pumps (unlike the 7-day pumps used for corneal angiogenesis assays) and delivered 0.25 μL of 100 μM SSTN per hr. This is roughly equivalent to the corneal angiogenesis assays in which the 7 day pumps deliver 1 μL of 30 μM SSTN per hr, which achieves significant inhibition of angiogenesis. After the 28 day treatment period, the tumors were again imaged in situ, indicating that the 5 control tumors were 10-11 times larger than tumors in the SSTN-treated animals (FIG. 15). The tumors were dissected and weighed, again showing that the SSTN reduced by tumor size by over 10-fold (FIG. 16). In addition, the SSTN-treated tumors appear pale, suggesting a lack of vascularization. Sectioning of the tumors and staining for mouse CD34, an endothelial cell marker, to monitor the ingrowth of host blood vessels into the human tumor shows a significant reduction in vessel density and vessel length. There is no positive staining using antibody specific for human CD34, indicating that the tumors are vascularized by host angiogenesis and that this is blocked by circulating SSTN.

Summary.

These results show that SSTN is an effective inhibitor of the $\alpha_v\beta_3$ and $\alpha_v\beta_3$ integrins both in vitro and in vivo. Syndecan-1 is expressed together with these integrins on activated endothelial cells undergoing angiogenesis in response to FGF and VEGF, or in tumors. The integrins appear to rely on syndecan-1 to undergo activation, as blocking syndecan-1 expression, deleting the integrin activation site from the syndecan receptor, or, as shown here, competing with the interaction of the syndecan with the integrins using a peptide (SSTN) containing the syndecan active site, all serve to inactivate the integrins and block endothelial cell attachment, spreading, and angiogenesis. SSTN (or SSTN mimetics) is an attractive therapeutic to target and inactivate these two integrins on tumor cells, activated endothelial cells, osteoclasts, and other cells that depend on these integrins in disease processes.

Example 4

The synstatin (SSTN) peptides that were previously tested have been derived from the mouse syndecan-1 (Sdc1) sequence so that their biological activity can be tested in mouse models without eliciting an immune response. Nonetheless, the in vitro work with cell lines shows that both the mouse and human Sdc1 have identical abilities to regulate the $\alpha v \beta 3$ and $\alpha v \beta 5$ integrins.

To test a human SSTN peptide, experiments were conducted with human SSTN with amino acids 88-121 of the human sequence (hSSTN 88-121) (SEQ ID NO:28) and amino acids 89-120 of the human sequence (hSSTN 89-120) (SEQ ID NO:21). The human and mouse Sdc1 sequences differ in length by one amino acid counting from the amino terminus to the beginning of the SSTN sequence (human is longer by one amino acid), and therefore, it was desirable to test not only the 88-121 sequence, but also 89-120 to make sure that the difference of one amino acid on either end would not affect its activity.

In FIG. 17, both peptides show identical abilities to block the attachment and spreading of human MDA-MB-231 breast carcinoma cells to vitronectin (VN). The inventors have shown previously that this attachment and spreading is dependent on Sdc1 activating the $\alpha_v \beta_3$ integrin on these cells (Beauvais et al., 2004). Furthermore, the two peptides show an IC50 of 0.1 to 0.3 which is identical to the most active mouse SSTN peptides (mouse SSTN 82-130 or mouse SSTN 88-122.) The peptides have no effect on cell attachment and spreading on fibronectin (FN) when used at a concentration 100-fold greater than their IC50. The inventors have shown previously (Beauvais et al., 2004) that attachment and spreading on FN relies on the $\alpha_5 \beta_1$ integrin and is not dependent on Sdc1.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,196,265
U.S. Pat. No. 4,554,101
U.S. Pat. No. 4,683,202
U.S. Pat. No. 5,302,523
U.S. Pat. No. 5,322,783
U.S. Pat. No. 5,384,253
U.S. Pat. No. 5,399,363
U.S. Pat. No. 5,440,013
U.S. Pat. No. 5,446,128
U.S. Pat. No. 5,464,765
U.S. Pat. No. 5,466,468
U.S. Pat. No. 5,475,085
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,618,914
U.S. Pat. No. 5,641,515
U.S. Pat. No. 5,656,610
U.S. Pat. No. 5,670,155
U.S. Pat. No. 5,672,681
U.S. Pat. No. 5,674,976
U.S. Pat. No. 5,702,932
U.S. Pat. No. 5,710,245
U.S. Pat. No. 5,736,524
U.S. Pat. No. 5,780,448
U.S. Pat. No. 5,789,215
U.S. Pat. No. 5,840,833
U.S. Pat. No. 5,846,225
U.S. Pat. No. 5,846,233
U.S. Pat. No. 5,859,184
U.S. Pat. No. 5,928,906
U.S. Pat. No. 5,929,237
U.S. Pat. No. 5,945,100
U.S. Pat. No. 5,981,274
U.S. Pat. No. 5,994,624
Adams et al., *J. Cell Biol.*, 152:1169-1182, 2001.
Akiyama et al., *J. Cell Biol.*, 109:863-875, 1989.
Albert et al., *Nat. Cell Biol.*, 2:899-905, 2000.
Alexander et al., *Nat. Genet.*, 25:329-332, 2000.
Anttonen et al., *Br. J. Cancer*, 79:558-564, 1999.
Ausubel et al., In: *Current Protocols in Molecular Biology*, John, Wiley & Sons, Inc, New York, 1994.
Baciu and Goetinck, *Mol. Biol. Cell*, 6:1503-1513, 1995.
Bader et al., *Cell*, 95:507-519, 1998.
Baichwal and Sugden, In: *Gene Transfer*, Kucherlapati (Ed.), New York, Plenum Press, 117-148, 1986.
Barany and Merrifield, In: *The Peptides*, Gross and Meienhofer (Eds.), Academic Press, New York, pp. 1-284 1979.
Barbareschi et al., *Cancer*, 98:474-483, 2003.
Bayer-Garner et al., *J. Cutan. Pathol.*, 28:135-139, 2001.
Beauvais and Rapraeger, *Exp. Cell Res.*, 286:219-232, 2003.
Beauvais and Rapraeger, *Exp. Cell Res.*, 286:219-232, 2004.
Beauvais and Rapraeger, *Reprod. Biol. Endocrinol.*, 2:3, 2004.
Beauvais et al., *J. Cell Biol.*, 167(1):171-81, 2004.
Bergers and Benjamin, *Nature Rev. Cancer*, 3:401-410, 2003.
Bernfield et al., *Annu. Rev. Biochem.*, 68:729-777, 1999.
Boettiger et al., *J. Biol. Chem.*, 276:31684-31690, 2001.
Boettiger et al., *Molec. Biol. Cell*, 12:1227-1237, 2001.
Boudreau et al., *J. Cell Biol.*, 139(1):257-264, 1997.
Brooks et al., *Cell*, 79:1157-1164, 1994.

Brooks et al., *J. Clin. Invest.*, 99:1390-1398, 1997.
Brooks et al., *Science*, 264:569-571, 1994.
Burbach et al., *Matrix Biol.*, 22:163-177, 2003.
Byzova et al., *Thromb. Haemost.*, 80:726-734, 1998.
Capaldi et al., *Biochem. Biophys. Res. Comm.*, 74(2):425-433, 1977.
Carey et al., *Exp. Cell Res.*, 214:12-21, 1994.
Carey et al., *J. Cell Biol.*, 124:161-170, 1994.
Carman and Springer, *Curr. Opin. Cell Biol.*, 15:547-556, 2003.
Chen and Okayama, *Mol. Cell Biol.*, 7(8):2745-2752, 1987.
Colorado et al., *Cancer Res.*, 60(9):2520-2526, 2000.
Conejo et al., *Int. J. Cancer*, 88:12-20, 2000.
Couchman et al., *Int. Rev. Cytol.*, 207:113-150, 2001.
Coupar et al., *Gene*, 68:1-10, 1988.
Crescimanno et al., *J. Pathol.*, 189:600-608, 1999.
De et al., *J. Biol. Chem.*, 278:39044-39050, 2003.
Degryse et al., *Oncogene*, 20:2032-2043, 2001.
Du et al., *Cell*, 65:409-416, 1991.
Elenius et al., *J. Cell Biol.*, 114(3): 585-595, 1991.
Elenius et al., *J. Cell Biol.*, 114:585-595, 1991.
Eliceiri and Cheresh, *J. Clin. Invest.*, 103:1227-1230, 1999.
Eliceiri et al., *J. Cell Biol.*, 140:1255-1263, 1998.
Eliceiri, *Circ. Res.*, 89:1104-1110, 2001.
Fechheimer et al., *Proc. Natl. Acad. Sci. USA*, 84:8463-8467, 1987.
Felding-Habermann and Cheresh, *Curr. Opin. Cell. Biol.*, 5:864-868, 1993.
Felding-Habermann et al., *Proc. Natl. Acad. Sci. USA*, 98:1853-1858, 2001.
Finnemann, *Adv. Exp. Med. Biol.*, 533:337-342, 2003b.
Finnemann, *Embo. J.*, 22:4143-4154, 2003a.
Fraley et al., *Proc. Natl. Acad. Sci. USA*, 76:3348-3352, 1979.
Frelinger et al., *J. Biol. Chem.*, 266:17106-17111, 1991.
Friedlander et al., *Science*, 270:1500-1502, 1995.
Friedmann, *Science*, 244:1275-1281, 1989.
Fujiya et al., *Jpn. J. Cancer Res.*, 92:1074-1081, 2001.
Gallo et al., *J. Invest. Derm.*, 107:676-683, 1996.
Gallo et al., *J. Invest. Dermatol.*, 107(5):676-683, 1996.
Gao et al., *J. Cell Biol.*, 35:533-544, 1996.
Giancotti and Ruoslahti, *Science*, 285:1028-1032, 1999.
Gopal, *Mol. Cell Biol.*, 5:1188-1190, 1985.
Gotte et al., *Invest. Ophthal. Visual Sci.*, 43(4):1135-1141, 2002.
Gotte et al., *IOVS*, 43:1135-1141, 2002.
Graham and Van Der Eb, *Virology*, 52:456-467, 1973.
Granes et al., *Exp. Cell Res.*, 248:439-456, 1999.
Hall et al., *Exp. Eye Res.*, 77:281-286, 2003.
Hansen et al., *J. Cell Biol.*, 126:811-819, 1994.
Harland and Weintraub, *J. Cell Biol.*, 101:1094-1099, 1985.
Harlow and Lane, In: *Antibodies*, A Laboratory manual, Cold Spring Harbor Laboratory, 1988.
Hayashi et al., *J. Histochem. Cytochem.*, 35:1079-1088, 1987.
Hermonat and Muzycska, *Proc. Natl. Acad. Sci. USA*, 81:6466-6470, 1984.
Hirabayashi et al., *Tumour Biol.*, 19:454-463, 1998.
Hood et al., *J. Cell Biol.*, 162:933-943, 2003.
Horwich et al., *Virol.*, 64:642-650, 1990.
Humphries, *Curr. Opin. Cell Biol.*, 8:632-640, 1996.
Iba et al., *J. Cell Biol.*, 149:1143-1156, 2000.
The et al., *J. Cell Biol.*, 143:547-560, 1998.
Inki and Jalkanen, *Ann. Med.*, 28:63-67, 1996.
Inki et al., *Br. J. Cancer*, 70:319-323, 1994.
Inki et al., *J. Pathol.*, 172:349-355, 1994.
Izzard et al., *Exp. Cell Res.*, 165:320-336, 1986.
Johannesson et al., *J. Med. Chem.*, 42(22):4524-4537, 1999.
Johnson et al., In: *Biotech. Pharm.*, Pezzuto et al. (Eds.), Chapman and Hall, NY, 1993.
Jones et al., *J. Oral. Pathol. Med.*, 26:63-68, 1997.
Kaeppler et al., *Plant Cell Reports* 9: 415-418, 1990.
Kainulainen et al., *J. Biol. Chem.*, 271:18759-18766, 1996.
Kamphaus et al., *J. Biol. Chem.*, 275(2):1209-1215, 2000.
Kamphaus et al., *J. Biol. Chem.*, 278:1209-1215, 2000.
Kaneda et al., *Science*, 243:375-378, 1989.
Kato et al, *J. Biol. Chem.*, 266:3361-3364, 1991.
Kato et al., *Mol. Biol. Cell*, 6:559-576, 1995.
Khan et al., *J. Biol. Chem.*, 263:11314-113148, 1988.
Kim et al., *Mol. Biol. Cell*, 5:797-805, 1994.
Kim et al., *Oncogene*, 22:826-830, 2003.
Klass et al., *J. Cell Sci.*, 113:493-506, 2000.
Klatka, *Eur. Arch. Otorhinolaryngol.*, 259:115-118, 2002.
Kumar-Singh et al., *J. Pathol.*, 186:300-305, 1998.
Kyte and Doolittle, *J. Mol Biol.*, 157(1):105-32, 1982.
Lebakken and Rapraeger, *J. Cell Biol.*, 132:1209-1231, 1996.
Lebakken, and Rapraeger, *J. Cell Biol.*, 132:1209-1221, 1996.
Leppa et al. *Cell Regul.*, 2:1-11, 1991.
Leppa et al., *J. Cell Sci.*, 109:1393-1403, 1996.
Leppa et al., *Proc. Natl. Acad. Sci. USA*, 89:932-936, 1992.
Levy et al., *Br. J. Cancer*, 74:423-431, 1996.
Levy et al., *Bull. Cancer*, 84:235-237, 1997.
Liapis et al., *Diagn. Mol. Pathol.*, 5:127-35, 1996.
Liddington and Ginsberg, *J. Cell Biol.*, 158:833-839, 2002.
Lindberg et al., *J. Cell Biol.*, 134:1313-1322, 1996.
Liu et al., *J. Biol. Chem.*, 273:22825-22832, 1998.
Maeshima et al., *J. Biol. Chem.*, 275(28):21340-21348, 2000.
Maniatis, et al., In: *Molecular Cloning*, A Laboratory Manual, Cold Spring Harbor Press, NY, 1990.
Matsumoto et al., *Int. J. Cancer*, 74:482-491, 1997.
McFall and Rapraeger, *J. Biol. Chem.*, 272:12901-12904, 1997.
McFall and Rapraeger, *J. Biol. Chem.*, 273:28270-28276, 1998.
McFall and Rapraeger, *J. Biol. Chem.*, 273:28270-28276, 1998.
McLean et al., *J. Biol. Chem.*, 265:17126-17131, 1990.
McQuade and Rapraeger, *J. Biol. Chem.*, 278:46607-46615, 2003.
McQuade et al., *J. Cell Sci.*, Syndecan-1 regulates {alpha}v{beta}5 integrin activity in B82L fibroblasts, May, 2006 [Epub ahead of print].
Memmo and McKeown-Longo, *J. Cell Sci.*, 111(Pt 4):425-433, 1998.
Merrifield, *Science*, 232: 341-347, 1986.
Mertens et al., *J. Biol. Chem.*, 267(28):20435-20443, 1992.
Miranti and Brugge, *Nat. Cell Biol.*, 4:E83-90, 2002.
Mundhenke et al., *Am. J. Pathol.*, 160:185-194, 2002.
Myers et al., *Am. J. Pathology*, 161(6): 2099-2109, 2002.
Myers et al., *J. Cell Biol.*, 148(2): 343-351, 2000.
Nakaerts et al., *Int. J. Cancer*, 74:335-345, 1997.
Nakanishi et al., *Intl. J. Cancer*, 80:527-532, 1999.
Nicolau and Sene, *Biochim. Biophys. Acta*, 721:185-190, 1982.
Nicolau et al., *Methods Enzymol.*, 149:157-176, 1987.
Numa et al., *Int. J. Oncol.*, 20:39-43, 2002.
Oh et al., *J. Biol. Chem.*, 272:11805-11811, 1997b.
Oh et al., *J. Biol. Chem.*, 272:8133-8136, 1997a.
Oh et al., *J. Biol. Chem.*, 273:10624-10629, 1998.
Ohtake et al., *Br. J. Cancer*, 81:393-403, 1999.
O'Reilly et al., *Cell*, 79(2):315-328, 1994.

O'Reilly et al., *Cell*, 88(2):277-285, 1997.
Panetti et al., *J. Biol. Chem.*, 270:18593-18597, 1995.
Park et al., *J. Biol. Chem.*, 277:29730-29736, 2002.
Pasqualini et al., *J. Cell Sci.*, 105(Pt 1):101-11, 1993.
PCT Appln. WO 94/09699
PCT Appln. WO 95/06128
Pelletier et al., *J. Biol. Chem.*, 271:1364-1370, 1996.
Petitclerc et al., *Cancer Res.*, 59:2724-2730, 1999.
Pilch et al., *J. Biol. Chem.*, 277:21930-21938, 2002.
Plow et al., *J. Biol. Chem.*, 275:21785-21788, 2000.
Plow et al., *J. Biol. Chem.*, 275:21785-21788, 2000.
Potrykus et al., *Mol. Gen. Genet.*, 199:183-188, 1985.
Potter et al., *Proc. Natl. Acad. Sci. USA*, 81:7161-7165, 1984.
Pulkkinen et al., *Acta Otolaryngol.*, 117:312-315, 1997.
Rapraeger and Ott, *Curr. Opin. Cell Biol.*, 10:620-628, 1998.
Rapraeger et al., *J. Cell Biol.*, 103:2683-2696, 1986.
Rapraeger, *J. Cell Biol.*, 149:995-998, 2000.
Ratnikov et al., *J. Biol. Chem.*, 277:7377-7385, 2002.
Remington's Pharmaceutical Sciences, 15$^{th}$ ed., pages 1035-1038 and 1570-1580, Mack Publishing Company, Easton, Pa., 1980.
Reynolds et al., *Nature Med.*, 8:27-34, 2002.
Reynolds et al., *Nature Med.*, 8:27-34, 2002.
Ridgeway, In: *Vectors: A survey of molecular cloning vectors and their uses*. Rodriguez and Denhardt (Eds.), Stoneham, Butterworth, 467-492, 1988.
Rintala et al., *Gynecol. Onol.*, 75:372-378, 1999.
Rippe et al., *Mot. Cell Biol.*, 10:689-695, 1990.
Roskelley et al., *Curr. Opin. Cell Biol.*, 7:736-747, 1995.
Sambrook et al., In: *Molecular Cloning, A Laboratory Manual*, 3rd Ed., Cold Spring Harbor Press, NY, 2001.
Sambrook et al., In: *Molecular Cloning, A Laboratory Manual*, 3rd Ed., Cold Spring Harbor Press, NY, 2000.
Sanderson and Bernfield, *Proc. Natl. Acad. Sci. USA*, 85:9562-9566, 1988.
Sanderson and Borset, *Ann. Hematol.*, 81:125-35, 2002.
Sanderson, *Semin. Cell Dev. Biol.*, 12:89-98, 2001.
Saoncella et al., *Proc. Natl. Acad. Sci. USA*, 96:2805-2810, 1999.
Singer et al., *J. Cell Biol.*, 104:573-584, 1987.
Soldi et al., *Embo J.*, 18:882-892, 1999.
Soukka et al., *J. Oral Pathol. Med.*, 29:308-313, 2000.
Stanley et al., *Am. J. Clin. Pathol.*, 112:377-383, 1999.
Stewart and Young, In: *Solid Phase Peptide Synthesis*, 2d. Ed., Pierce Chemical Co. 1984.
Streeter and Rees, *J. Cell Biol.*, 105:507-515, 1987.
Stupack and Cheresh, *Oncogene*, 22:9022-9029, 2003.
Stupack et al., *J. Cell Biol.*, 155:459-470, 2001.
Sun et al., *Int. J. Dev. Biol.*, 42:733-736, 1998.
Tam et al., *J. Am. Chem. Soc.*, 105:6442, 1983.
Tkachenko and Simons, *J. Biol. Chem.*, 277:19946-19951, 2002.
Tonn et al., *Anticancer Res.*, 18:2599-2605, 1998.
Tumova et al., *J. Biol. Chem.*, 275:9410-9417, 2000.
Tur-Kaspa et al., *Mol. Cell Biol.*, 6:716-718, 1986.
Urbinati et al., *Atherosc., Thrombosis & Vasc. Biol.*, 25: 2315-2320, 2005
van der Flier and Sonnenberg, *Cell Tissue Res.*, 305:285-298, 2001.
Vita et al., *Biopolymers*, 47:93-100, 1998.
Weisshoff et al., *Eur. J. Biochem.*, 259(3):776-788, 1999.
Wiksten et al., *Int. J. Cancer*, 95:1-6, 2001.
Wong et al., *Gene*, 10:87-94, 1980.
Woods and Couchman, *Curr. Opin. Cell Biol.*, 13:578-583, 2001.
Woods and Couchman, *Mol. Biol. Cell*, 5:183-192, 1994.
Woods et al., *Embo J.*, 5:665-670, 1986.
Wu and Wu, *J. Biol. Chem.*, 262:4429-4432, 1987.
Wu and Wu, *Biochemistry*, 27:887-892, 1988.
Xiong et al., *Science*, 294:339-345, 2001.
Xue et al., *Cancer Res.*, 57:1682-1689, 1997.
Yamashita et al., *J. Immunol.*, 162:5940-5948, 1999.
Yan et al. *J. Biol. Chem.*, 275:7249-7260, 2000.

What is claimed is:

1. A method of treating a subject having a disease characterized by angiogenesis wherein the disease is not cancer, comprising contacting endothelial cells of the subject that express $\alpha_v\beta_3$ or $\alpha_v\beta_5$ integrin and are responsible for said angiogenesis with a peptide or polypeptide segment consisting of 32 to 100 amino acid residues and comprising SEQ ID NO:21, whereby the disease is treated.

2. The method of claim 1, wherein said peptide or polypeptide segment is 35, 40, 45, 49, 50, 55, 60, 65, 70, 75, 80, 85, 90, 95 or 100 amino acid residues in length.

3. The method of claim 1, wherein said peptide or polypeptide segment is 32 to 80 amino acid residues in length.

4. The method of claim 1, wherein said peptide or polypeptide segment is 32 to 50 amino acid residues in length.

5. The method of claim 1, wherein said peptide or polypeptide segment is 32 to 40 amino acid residues in length.

6. The method of claim 1, wherein said peptide segment consists of SEQ ID NO:10.

7. The method of claim 1, wherein said peptide segment comprises at least 35 contiguous amino acids from SEQ ID NO:10.

8. The method of claim 1, wherein said peptide segment consists of SEQ ID NO:28.

9. The method of claim 1, wherein said peptide segment consists of SEQ ID NO:21.

10. The method of claim 1, wherein said disease is selected from the group consisting of abnormalities of the vasculature, abnormalities of the eye, abnormalities of the skin, abnormalities of the uterus and ovary, abnormalities of the adipose tissue, abnormalities of the bones and joints, and AIDS-related pathologies resulting from TAT protein of the human immunodeficiency virus (HIV) activating the $\alpha_v\beta_3$ integrin on endothelial cells.

11. The method of claim 10, wherein said disease is selected from the group consisting of atherosclerosis, hemangiomas, diabetic retinopathy, retinopathy of prematurity, pyogenic granulomas, psoriasis, warts, scar keloids, allergic edema, ulcers, dysfunctional uterine bleeding, follicular cysts, endometriosis, pre-eclampsia, obesity, rheumatoid arthritis, and osteophyte formation.

12. The method of claim 1, wherein contacting comprises systemic administration of said peptide or polypeptide segment or administration of said peptide or polypeptide segment local to said endothelial cells.

13. The method of claim 1, wherein said peptide or polypeptide segment is active at 0.3 µM.

14. The method of claim 1, wherein said peptide or polypeptide segment is active at 0.1 µM.

15. The method of claim 1, further comprising contacting said endothelial cells with a second anti-angiogenic agent.

* * * * *